(12) United States Patent
Coburn et al.

(10) Patent No.: US 9,556,202 B2
(45) Date of Patent: Jan. 31, 2017

(54) SULFONAMIDE DERIVATIVES AND METHODS OF USE THEREOF FOR IMPROVING THE PHARMACOKINETICS OF A DRUG

(71) Applicant: MERCK SHARP & DOHME CORP., Rahway, NJ (US)

(72) Inventors: Craig A. Coburn, Royersford, PA (US); Milana Maletic, Summit, NJ (US); Richard Soll, Shanghai (CN); Chunsing Li, Shanghai (CN); Yunfu Luo, Shanghai (CN); Zhiqi Qi, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/410,846

(22) PCT Filed: Jun. 25, 2013

(86) PCT No.: PCT/US2013/047451
§ 371 (c)(1),
(2) Date: Dec. 23, 2014

(87) PCT Pub. No.: WO2014/004416
PCT Pub. Date: Jan. 3, 2014

(65) Prior Publication Data
US 2015/0197531 A1    Jul. 16, 2015

(30) Foreign Application Priority Data
Jun. 27, 2012    (WO) ................ PCT/CN2012/077611

(51) Int. Cl.
| | | |
|---|---|---|
| *C07D 498/04* | (2006.01) | |
| *C07D 417/10* | (2006.01) | |
| *C07D 417/12* | (2006.01) | |
| *C07D 417/14* | (2006.01) | |
| *C07D 487/04* | (2006.01) | |
| *C07D 401/14* | (2006.01) | |
| *A61K 31/496* | (2006.01) | |
| *A61K 31/4545* | (2006.01) | |
| *A61K 31/4985* | (2006.01) | |
| *A61K 31/4402* | (2006.01) | |
| *A61K 31/513* | (2006.01) | |
| *A61K 31/5377* | (2006.01) | |
| *A61K 31/5383* | (2006.01) | |
| *C07D 471/10* | (2006.01) | |
| *C07D 471/04* | (2006.01) | |
| *A61K 38/05* | (2006.01) | |
| *C07D 403/14* | (2006.01) | |

(Continued)

(52) U.S. Cl.
CPC ......... *C07D 498/04* (2013.01); *A61K 31/4402* (2013.01); *A61K 31/496* (2013.01); *A61K 31/4985* (2013.01); *A61K 31/513* (2013.01); *A61K 31/5377* (2013.01); *A61K 31/5383* (2013.01); *A61K 38/05* (2013.01); *A61K 45/06* (2013.01); *C07D 401/14* (2013.01); *C07D 403/14* (2013.01); *C07D 417/12* (2013.01); *C07D 417/14* (2013.01); *C07D 471/04* (2013.01); *C07D 471/10* (2013.01); *C07D 487/04* (2013.01); *C07D 491/04* (2013.01)

(58) Field of Classification Search
None
See application file for complete search history.

(56) References Cited

U.S. PATENT DOCUMENTS

| 7,919,488 B2 | 4/2011 | Planken et al. |
|---|---|---|
| 2007/0167497 A1 | 7/2007 | Nambu et al. |
| 2008/0021011 A1 | 1/2008 | Planken et al. |

(Continued)

FOREIGN PATENT DOCUMENTS

| WO | 03076422 A1 | 9/2003 |
|---|---|---|
| WO | 2006108879 A2 | 10/2006 |

(Continued)

OTHER PUBLICATIONS

Berge et al., "Pharmaceutical Salts", J. Pharm Sci., 1977, pp. 1-19, vol. 66(1).

(Continued)

*Primary Examiner* — Emily Bernhardt
(74) *Attorney, Agent, or Firm* — Jeffrey P. Bergman; Catherine D. Fitch

(57) ABSTRACT

The present invention relates to Sulfonamide Derivatives of Formula (I):

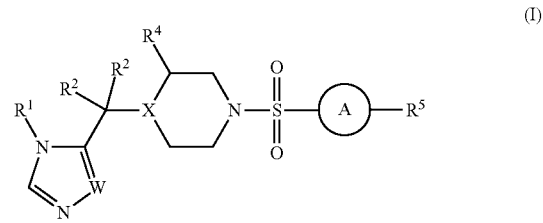

and pharmaceutically acceptable salts thereof, wherein A, W, X, $R^1$, $R^2$, $R^3$, $R^4$ and $R^5$ are as defined herein. The present invention also relates to compositions comprising at least one Sulfonamide Derivative, and methods of using the Sulfonamide Derivatives for improving the pharmacokinetics of a drug.

20 Claims, No Drawings

(51) Int. Cl.
*C07D 491/04* (2006.01)
*A61K 45/06* (2006.01)

(56) References Cited

U.S. PATENT DOCUMENTS

2009/0175820 A1 7/2009 Desai et al.
2014/0005103 A1* 1/2014 Coburn ............... C07D 401/14
514/4.1

FOREIGN PATENT DOCUMENTS

WO 2007034312 A2 3/2007
WO 2008010921 A2 1/2008

OTHER PUBLICATIONS

Bingham et al., "Over One Hundred Solvates of Sulfathiazole", Chem. Commun., 2001, pp. 603-604.
Bolm, C., et al, "a-Trialkylsily-Substituted a-Amino Acids", Angew. Chem. Int. Ed., 2000, pp. 2288-2290, vol. 39, No. 13.
Caira et al., "Preparation and Crystal Characterization of a Polymorph,a Monohydrate, and an Ethyl Acetate Solvate of the Antifungal Fluconazole", J. Pharmaceutical Sci., 2004, 601-611, vol. 93(3).
Giralt, E., et al, "Replacement of a Proline With Silaproline Causes a 20-Fold Increase in the Cellular Uptake of a Pro-Rich Peptide", J. Am. Chem. Soc., 2006, p. 8479-8483, vol. 128.
Gould, P.L., et al., "Salt Selection for Basic Drugs", Intl J. Pharmaceutics, 1986, 201-217, vol. 33.
Johansson, T., et al, "In Vitro Metabolism of Haloperidol and Sila-Haloperidol: new Metabolic Pathways Resulting From Carbon/Silicon Exchange", Drug Metabolism and Disposition, 2010, pp. 78-83, vol. 38, (1 page provided).
S-M Huang, et al, "Drug Interaction Studies: Study Design, Data Analysis, and Implications for Dosing and Labeling", Nature, Feb. 2007, pp. 298-305, vol. 81, No. 2, US.
T. Higuchi and V. Stella, Pro-drugs as NovelDelivery Systems (1987) 14 of the A.C.S. Symposium Series, (6 pages provided).
Van Tonder, et al, "Preparation and Physicochemical Characterization of 5 Niclosamide Solvates and 1 Hemisolvate", AAPS Pharmscitech, 2004, pp. 1-10, 5(1), US.

* cited by examiner

SULFONAMIDE DERIVATIVES AND METHODS OF USE THEREOF FOR IMPROVING THE PHARMACOKINETICS OF A DRUG

CROSS-REFERENCE TO RELATED APPLICATIONS

This application is the national stage application under 35 U.S.C. 371 of International Patent Application No. PCT/US2013/047451, filed Jun. 25, 2013, which claims priority to International Patent Application No. PCT/CN2012/077611, filed Jun. 27, 2012. Each of the aforementioned PCT applications is incorporated by reference in its entirety.

FIELD OF THE INVENTION

The present invention relates to Sulfonamide Derivatives, compositions comprising at least one Sulfonamide Derivative, and methods of using the Sulfonamide Derivatives for improving the pharmacokinetics of a drug.

BACKGROUND OF THE INVENTION

The cytochrome P450 enzyme system (CYP450) is responsible for the biotransformation of drugs from active substances to inactive metabolites that can be excreted from the body. In addition, the metabolism of certain drugs by CYP450 can alter their PK profile and result in sub-therapeutic plasma levels of those drugs over time. In the area of antiviral therapy, this can lead to resistance of the virus to the drug.

The virus causing acquired immunodeficiency syndrome (AIDS) is know by various names, including human immunodeficiency virus (HIV), of which two distinct families have been identified—HIV-1 and HIV-2. Many inhibitors of HIV, including HIV protease inhibitors, HIV integrase inhibitors and non-nucleoside reverse transcriptase inhibitors are metabolized by CYP450. This metabolic activity can lead to unfavorable pharmacokinetics, requiring administering more frequent and/or higher doses than are optimal.

Many drugs, including some HIV protease inhibitors, are now paired with other agents that improve exposure of the drug, with the drug-drug interaction being commonly referred to as "boosting." International Publication Nos. WO 2006/108879, WO 2007/034312 and WO 2008/010921; U.S. Patent Publication No. US 2009/0175820; and U.S. Pat. No. 7,919,488 describe compounds useful as pharmacokinetic enhancers.

Ritonavir, a common boosting agent, is widely used with HIV agents and is an HIV protease inhibitor itself that exerts its boosting effect through inhibition of Cytochrome P450 3A4 (CYP3A4) and p-glycoprotein drug transporters. Ritonavir, however, is associated with certain risks, including hepatotoxicity, hyperlipidemia and unfavorable gastrointestinal effects.

SUMMARY OF THE INVENTION

In one aspect, the present invention provides Compounds of Formula (I):

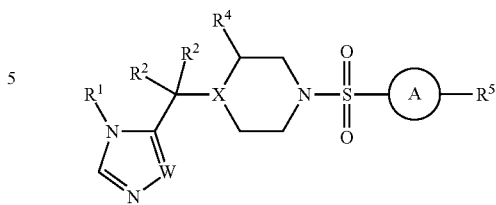

and pharmaceutically acceptable salts thereof,
wherein:
A is a 5 or 6-membered heteroarylene group;
W is N or —CH—;
X is N or —C(R$^3$)—;
R$^1$ is selected from —(C$_1$-C$_6$ alkylene)-aryl, —(C$_1$-C$_6$ alkylene)-(5 or 6-membered heteroaryl), —(C$_1$-C$_6$ alkylene)-O-aryl, —(C$_1$-C$_6$ alkylene)-O-(5 or 6-membered heteroaryl) and C$_3$-C$_6$ cycloalkyl, wherein any aryl, heteroaryl or C$_3$-C$_6$ cycloalkyl group can be optionally substituted with up to four R$^7$ groups, which can be the same or different, and wherein said C$_3$-C$_6$ cycloalkyl group can be fused to a benzene ring and said fused benzene ring can be optionally substituted with up to four R$^7$ groups, which can be the same or different;
each occurrence of R$^2$ is independently selected from H, C$_1$-C$_6$ alkyl, —OH, —O—(C$_1$-C$_6$ alkyl) and —(C$_1$-C$_6$ alkylene)-O—(C$_1$-C$_6$ alkyl);
R$^3$ is selected from H, C$_1$-C$_6$ alkyl, C$_1$-C$_6$ hydroxyalkyl and —CN, or R$^3$ and an R$^2$ group, together with the carbon atoms to which they are attached, can combine to form a cyclopropyl ring;
R$^4$ is H, or R$^4$ and an R$^2$ group, can join to form a group selected from —CH$_2$—CH$_2$—CH$_2$—, —C(O)—O—CH$_2$—, —CH$_2$—O—CH$_2$— and —CH$_2$—N(R$^8$)—CH$_2$—;
R$^5$ is —NH(R$^6$), 5 or 6-membered monocyclic heterocycloalkyl or 9 or 10-membered bicyclic heterocycloalkyl, wherein said 5 or 6-membered monocyclic heterocycloalkyl group can optionally form a spirocycle with a C$_3$-C$_6$ cycloalkyl group or another 5 or 6-membered monocyclic heterocycloalkyl group, and wherein said 5 or 6-membered monocyclic heterocycloalkyl group and said 9 or 10-membered bicyclic heterocycloalkyl group can be optionally substituted on one or more ring carbon atoms with up to four R$^7$ groups, which can be the same or different, and wherein a ring carbon atom of a 5 or 6-membered monocyclic heterocycloalkyl group may be functionalized as a carbonyl group
R$^6$ is C$_1$-C$_6$ alkyl or 5 or 6-membered heteroaryl, wherein said C$_1$-C$_6$ alkyl group is optionally substituted with 1 or 2 groups, each independently being NH$_2$ or halo, and wherein said 5 or 6-membered heteroaryl group can be optionally substituted with up to four R$^7$ groups;
each occurrence of R$^7$ is independently selected from C$_1$-C$_6$ alkyl, 5 or 6-membered heterocycloalkyl, C$_1$-C$_6$ hydroxyalkyl, C$_1$-C$_6$ haloalkyl, halo, —CN, —N(R$^8$)$_2$, —CH$_2$N(R$^8$)$_2$, —OR$^8$, —C(O)OR$^8$, —SR$^8$, —S(O)$_2$R$^8$ and —C(O)N(R$^8$)$_2$, wherein said 5 or 6-membered heterocycloalkyl group can be optionally substituted with a group selected from C$_1$-C$_6$ alkyl, halo, C$_1$-C$_6$ hydroxyalkyl, C$_1$-C$_6$ haloalkyl, halo, —CN, —N(R$^8$)$_2$ and —OR$^8$; and
each occurrence of R$^8$ is independently H or C$_1$-C$_6$ alkyl.

The Compounds of Formula (I) (also referred to herein as the "Sulfonamide Derivatives") and pharmaceutically acceptable salts thereof can inhibit CYP3A4, and are also believed to be useful, for example, for enhancing or improving the pharmacokinetics of a drug that is metabolized by CYP3A4. Without being bound by any specific theory, it is believed that the Sulfonamide Derivatives inhibit CYP3A4, and possibly other members of the CYP3A family.

Accordingly, the present invention provides methods for improving the pharmacokinetics of a therapeutic compound that is metabolized by CYP3A4, the methods comprising administering to a subject in need of such treatment an effective amount of a combination of said drug and a compound of Formula (I) or a pharmaceutically acceptable salt thereof.

The present invention also provides methods for inhibiting CYP3A4 in a subject, comprising administering to said subject a compound of Formula (I) or pharmaceutically acceptable salt thereof, in an amount that is effective to inhibit CYP3A4 in said subject.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to Sulfonamide Derivatives, compositions comprising at least one Sulfonamide Derivative, and methods of using the Sulfonamide Derivatives for inhibiting CYP3A4 or for improving the pharmacokinetics of a therapeutic compound that is metabolized by CYP3A4.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In still another embodiment, the subject is a dog, cat, horse, pig, hamster or other companion animal.

The term "effective amount" as used herein, refers to: (i) an amount administered of a Sulfonamide Derivative, or pharmaceutically acceptable salt thereof, that is effective for inhibiting CYP3A4 in a subject, (ii) the amounts administered of each of a combination of: (A) a Sulfonamide Derivative, or pharmaceutically acceptable salt thereof, and (B) a therapeutic compound metabolized by CYP3A4 wherein the amounts administered are together effective in producing the desired therapeutic, ameliorative, inhibitory or preventative effect when administered to a subject. In one embodiment the patient is suffering from HIV infection or AIDS and the therapeutic compound is an anti-HIV agent. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_3$-C$_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

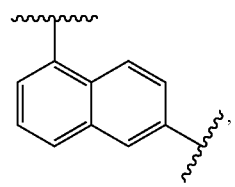 [SMILES: *c1ccc2c(*)cccc2c1]

is understood to represent both:

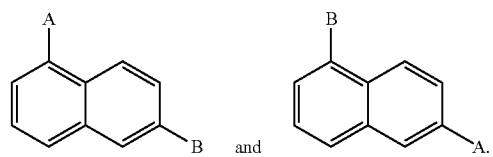

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

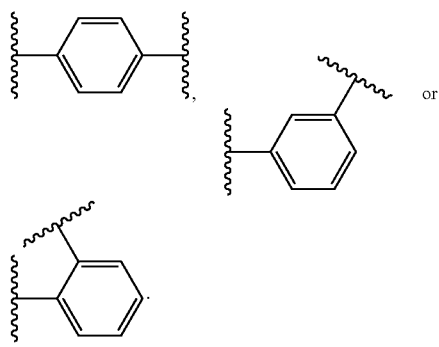

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

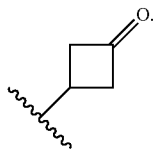 [SMILES: *C1CC(=O)C1]

The term "CYP3A," as used herein, refers to the all the known members of the 3A subfamily of the cytochrome P450 superfamily of genes. CYP3A includes, but is not limited to CYP3A4, CYP3A5, CYP3A7 and CYP3A43. In one embodiment, the CYP3A gene is CYP3A4.

The term "halo," as used herein, means —F, —Cl, —Br or —I. In one embodiment, the halo group is F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, the heterocycloalkyl group is bicyclic and has 9 or 10 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

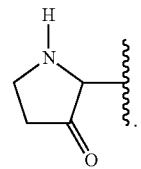

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heteroarylene," as used herein, refers to a bivalent group derived from a heteroaryl group, as defined above, by removal of a hydrogen atom from a ring carbon of a heteroaryl group. A heteroarylene group can be derived from a monocyclic or multicyclic ring system comprising from about 6 to about 14 carbon atoms. In one embodiment, a heteroarylene group contains from about 6 to about 10 carbon atoms. In another embodiment, a heteroarylene group is a naphthylene group. In another embodiment, a heteroarylene group is a phenylene group. A heteroarylene group can be optionally substituted with one or more "ring system substituents" which may be the same or different, and are as defined herein below. A heteroarylene group is divalent and either available bond on a heteroarylene group can connect to either group flanking the heteroarylene group. For example, the group "A-heteroarylene-B," wherein the arylene group is:

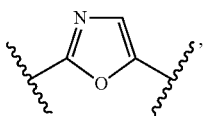 [SMILES: *c1cnc(*)o1]

is understood to represent both:

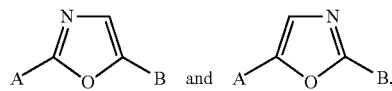

Non-limiting examples of heteroarylene groups include thiazolyl, pyridyl, pyranyl, tetrahydropyranyl, pyrmidinyl, indolyl, benzoquinolinyl, oxazolyl, benzisoxazolyl and pyrazinyl. In one embodiment, a heteroarylene group is unsubstituted. Unless otherwise indicated, a heteroarylene group is unsubstituted.

The term "HIV," as used herein, refers generically to all known species of the HIV virus, including, but not limited to, HIV-1 and HIV-2.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O— alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si (alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

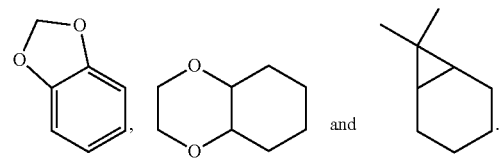

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., C$_1$-C$_6$ alkyl, R$^2$, R$^8$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Sulfonamide Derivative or a pharmaceutically acceptable salt of the compound. The transformation may occur by various mechanisms (e.g., by metabolic or chemical processes), such as, for example, through hydrolysis in blood.

For example, if a Sulfonamide Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like. Similarly, if a Sulfonamide Derivative contains an alcohol functional group, a prodrug can be formed by the replacement of one or more of the hydrogen atoms of the alcohol groups with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate) or a phosphate of structure $PO_3M_2$ where M is either sodium or potassium.

If a Sulfonamide Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$ alkyl; carboxy $(C_1-C_6)$alkyl; amino$(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N, N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Sulfonamide Derivatives can form salts which are also within the scope of this invention. Reference to a Sulfonamide Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Sulfonamide Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Sulfonamide Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Sulfonamide Derivatives may be atropisomers (e.g., substituted biaryls) and are considered as part of this invention. Enantiomers can also be directly separated using chiral chromatographic techniques.

It is also possible that the Sulfonamide Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Sulfonamide Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Sulfonamide Derivatives, and of the salts, solvates, hydrates, esters and prodrugs of the Sulfonamide Derivatives, are intended to be included in the present invention.

The following abbreviations are used below and have the following meanings: AcOH is acetic acid; Boc is tert-butyloxycarbonyl, (Boc)$_2$O or Boc$_2$O is Boc anhydride; n-BuLi is n-butyl lithium; t-BuNO$_2$ or t-BuONO is tert-butyl nitrite; Cbz is carboxybenzyl; DCM is dichloromethane; DIEA is N,N-diisopropylethylamine; DMF is dimethylformamide; DMSO is dimethylsulfoxide; EtOAc is ethyl acetate; EtOH is ethanol; Et$_a$ or TEA is triethylamine; HMPA is hexamethylphosphoramide; HOAc is acetic acid; HPLC is high-pressure liquid chromatography; KSCN is potassium thiocyanate; LCMS is liquid chromatography-mass spectrometry; LDA is lithium diisopropylamide; MeCN is acetonitrile; MeI is iodomethane; MeOH is methanol; MS is mass spectroscopy; NaBH(OAc)$_3$ is sodium triacetoxy borohydride; NMR is nuclear magnetic resonance spectroscopy; PCy$_3$ is tricyclohexylphosphine; Pd(OAc)$_2$ is palladium(II) acetate; Pd$_2$(dba)$_3$ is tris dibenzylideneacetone dipalladium; PE is petroleum ether; PG is protecting group; Pd/C is palladium on carbon; Prep is preparative; rt is room temperature; TBAF is n-tetrabutylammonium fluoride; TFA is trifluoroacetic acid; TLC is thin-layer chromatography; TMSCN is trimethylsilyl cyanide; Ts is 4-toluenesulfonyl; THF is tetrahydrofuran; wt % is percentage by weight; and X-phos is 2-dicyclohexylphosphino-2',4',6'-triisopropylbiphenyl.

The Compounds of Formula (I)

The present invention provides Sulfonamide Derivatives of Formula (I):

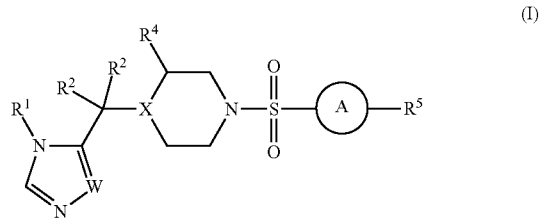

and pharmaceutically acceptable salts thereof, wherein A, W, $R^1$, $R^2$, $R^3$, $R^4$ and $R^5$ are defined above for the Compounds of Formula (I).

In one embodiment, A is 5-membered heteroarylene.
In another embodiment, A is 6-membered heteroarylene.
In another embodiment, A is thiazolyl.
In another embodiment, A is pyridyl.
In another embodiment, A is pyrazinyl.
In one embodiment, W is N.
In another embodiment, W is CH.
In one embodiment, X is N.
In another embodiment, X is —C($R^3$)—.
In another embodiment, X is —CH—.
In still another embodiment, X is —C($R^3$)— and $R^3$ and an $R^2$ group, together with the carbon atoms to which they are attached, combine to form a cyclopropyl ring.
In one embodiment, $R^1$ is —($C_1$-$C_6$ alkylene)-aryl, wherein said aryl moiety can be optionally substituted.
In another embodiment, $R^1$ is —CH($CH_3$)-phenyl, wherein said phenyl moiety can be optionally substituted with up to four $R^7$ groups, which can be the same or different.
In another embodiment, $R^1$ is selected from:

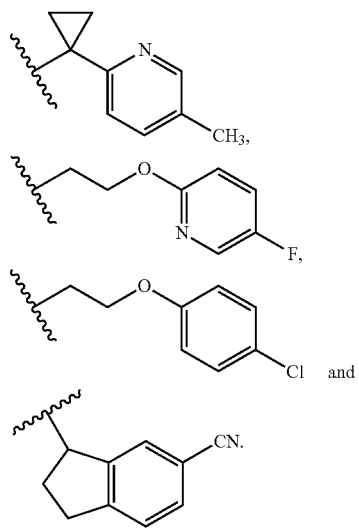

In another embodiment, $R^1$ is:

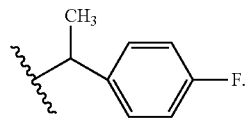

In still another embodiment, $R^1$ is —($C_1$-$C_6$ alkylene)-(5 or 6-membered heteroaryl), wherein said 5 or 6-membered heteroaryl moiety can be optionally substituted.
In another embodiment, $R^1$ is —($C_1$-$C_6$ alkylene)-O-aryl, wherein said aryl moiety can be optionally substituted.
In yet another embodiment, $R^1$ is —($C_1$-$C_6$ alkylene)-O-(5 or 6-membered heteroaryl), wherein said 5 or 6-membered heteroaryl moiety can be optionally substituted
In a further embodiment, $R^1$ is $C_3$-$C_6$ cycloalkyl, which can be optionally substituted.
In one embodiment, each occurrence of $R^2$ is H.

In another embodiment, one occurrence of $R^2$ is H and the other occurrence of $R^2$ is other than H.
In another embodiment, one occurrence of $R^2$ is H and the other occurrence of $R^2$ is —OH.
In still another embodiment, one occurrence of $R^2$ is H and the other occurrence of $R^2$ is —O—($C_1$-$C_6$ alkyl).
In another embodiment, one occurrence of $R^2$ is H and the other occurrence of $R^2$ is —($C_1$-$C_6$ alkylene)-O—($C_1$-$C_6$ alkyl).
In still another embodiment, one occurrence of $R^2$ is H and the other occurrence of $R^2$ is —$OCH_3$ or —$CH_2CH_2OCH_3$.
In one embodiment $R^3$ is H.
In another embodiment, $R^3$ is —$CH_2OH$ or —CN.
In one embodiment $R^4$ is H.
In another embodiment, $R^4$ and an $R^2$ group, join to form a group selected from —$CH_2$—$CH_2$—$CH_2$—, —C(O)—O—$CH_2$—, —$CH_2$—O—$CH_2$— and —$CH_2$—N($R^8$)—$CH_2$—;
In one embodiment $R^5$ is —NH($R^6$).
In another embodiment $R^5$ is —NH($R^6$), wherein $R^6$ is pyridyl, which can be optionally substituted.
In another embodiment $R^5$ is:

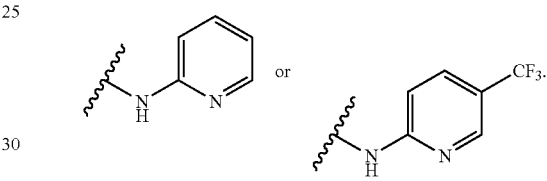

In still another embodiment, $R^5$ is 5 or 6-membered monocyclic heterocycloalkyl, which is optionally substituted.
In another embodiment, $R^5$ is 9 or 10 membered bicyclic heterocycloalkyl, which is optionally substituted.
In another embodiment, $R^5$ is 5 or 6-membered monocyclic heterocycloalkyl, which forms a spirocycle with a $C_3$-$C_6$ cycloalkyl group or another 5 or 6-membered monocyclic heterocycloalkyl group.
In yet another embodiment, $R^5$ is selected from:

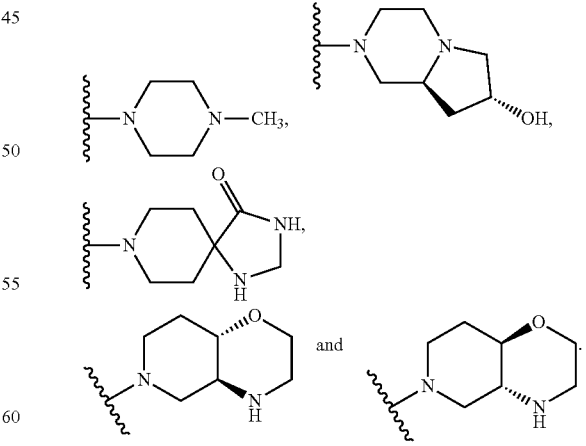

In one embodiment, X is N and each of $R^2$ is H.
In another embodiment, X is N, each of $R^2$ is H, and $R^4$ is H.
In another embodiment, W is CH, X is N, each of $R^2$ is H, and $R^4$ is H.

In one embodiment, $R^1$ is selected from:

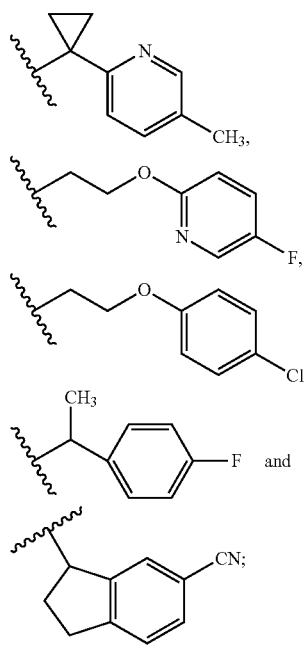

and $R^5$ is selected from:

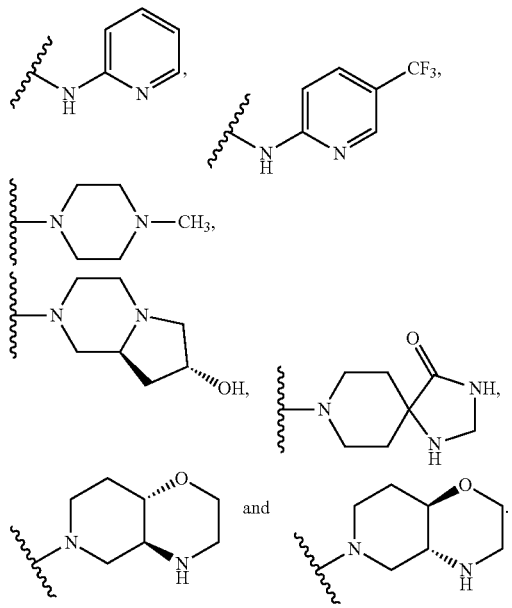

In one embodiment, the compounds of formula (I) have the formula (Ia):

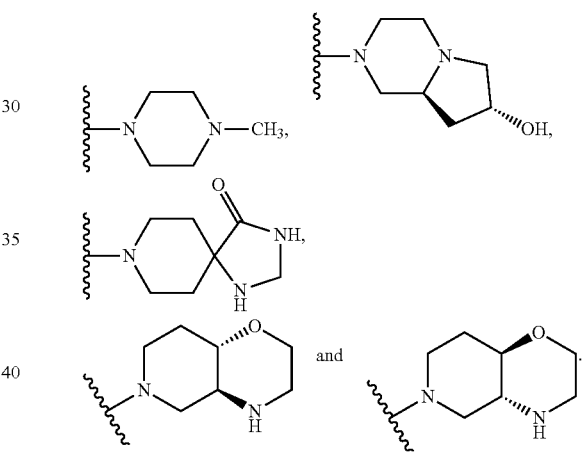

or a pharmaceutically acceptable salt thereof, wherein:

$R^5$ is 5 or 6-membered monocyclic heterocycloalkyl, 9 or 10-membered bicyclic heterocycloalkyl, wherein said 5 or 6-membered monocyclic heterocycloalkyl group can optionally form a spirocycle with a $C_3$-$C_6$ cycloalkyl group or another 5 or 6-membered monocyclic heterocycloalkyl group, and wherein said 5 or 6-membered monocyclic heterocycloalkyl group, said 9 or 10-membered bicyclic heterocycloalkyl and said spirocycle can be optionally substituted on one ring carbon atom with $C_1$-$C_6$ alkyl or halo; and each occurrence of $R^7$ is independently selected from H, $C_1$-$C_6$ alkyl or halo.

In one embodiment, for the compounds of Formula (Ia), $R^5$ is 5 or 6-membered monocyclic heterocycloalkyl, which is optionally as described above for the compounds of formula (Ia).

In another embodiment, for the compounds of Formula (Ia), $R^5$ is 9 or 10 membered bicyclic heterocycloalkyl, which is optionally substituted as described above for the compounds of formula (Ia).

In another embodiment, for the compounds of Formula (Ia), $R^5$ is 5 or 6-membered monocyclic heterocycloalkyl, which forms a spirocycle with a $C_3$-$C_6$ cycloalkyl group or another 5 or 6-membered monocyclic heterocycloalkyl group.

In yet another embodiment, for the compounds of Formula (Ia), $R^5$ is selected from:

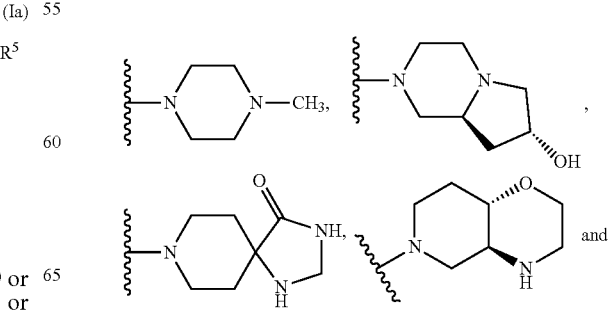

In one embodiment, for the compounds of Formula (Ia), $R^7$ is halo.

In another embodiment, for the compounds of Formula (Ia), $R^7$ is H.

In another embodiment, for the compounds of Formula (Ia), $R^7$ is $C_1$-$C_6$ alkyl.

In still another embodiment, for the compounds of Formula (Ia), $R^7$ is F.

In one embodiment, for the compounds of Formula (Ia), $R^5$ is selected from:

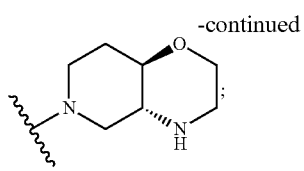

and
R⁷ is F.

In one embodiment, variables A, W, $R^1$, $R^2$, $R^3$, $R^4$ and $R^5$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising one or more therapeutic compounds that are metabolized by CYP3A4.

(c) The pharmaceutical composition of (b), wherein the therapeutic compound is an anti-HIV drug, preferably the anti-HIV drug(s) are selected from the group consisting of HIV protease inhibitors, HIV integrase inhibitors nucleoside reverse transcriptase inhibitors and non-nucleoside reverse-transcriptase inhibitors.

(d) A pharmaceutical combination that is (i) a Compound of Formula (I) and ii) a therapeutic compound metabolized by CYP3A4; wherein the Compound of Formula (I) and the therapeutic compound metabolized by CYP3A4 are each employed in an amount that renders the combination effective for inhibiting HIV replication, or for treating HIV infection and/or reducing the likelihood or severity of symptoms of HIV infection.

(e) The combination of (d), wherein the therapeutic compound metabolized by CYP3A4 is selected from the group consisting of HIV protease inhibitors, HIV integrase inhibitors, nucleoside reverse transcriptase inhibitors and non-nucleoside reverse-transcriptase inhibitors.

(f) A method of inhibiting HIV replication in a subject in need thereof which comprises administering to the subject: (i) a Compound of Formula (I) and (ii) one or more anti-HIV drugs, wherein the amounts of the Compound of Formula (I) and the anti-HIV drug(s) are together effective to inhibit HIV replication.

(g) A method of treating HIV infection and/or reducing the likelihood or severity of symptoms of HIV infection in a subject in need thereof which comprises administering to the subject (i) a Compound of Formula (I) and (ii) one or more anti-HIV drugs, wherein the amounts of the Compound of Formula (I) and the anti-HIV drug(s) are together effective to treat HIV infection.

(h) The method of (h), wherein the anti-HIV drug(s) are an selected from the group consisting of HIV protease inhibitors, HIV integrase inhibitors, nucleoside reverse transcriptase inhibitors and non-nucleoside reverse-transcriptase inhibitors.

(i) A method of inhibiting HIV replication in a subject in need thereof which comprises administering to the subject the pharmaceutical composition of (b) or (c) or the combination of (d) or (e).

(j) A method of treating HIV infection and/or reducing the likelihood or severity of symptoms of HIV infection in a subject in need thereof which comprises administering to the subject the pharmaceutical composition of (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention are employed in combination with one or more anti-HIV drugs.

Additional embodiments of the invention include the pharmaceutical compositions, combinations and methods set forth in (a)-(j) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (j) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-48 as set forth below, and pharmaceutically acceptable salts thereof.

Uses of the Sulfonamide Derivatives

The Sulfonamide Derivatives are useful in human and veterinary medicine for inhibiting CYP3A4. In addition, the Sulfonamide Derivatives are useful for improving the pharmacokinetics of a therapeutic compound that is metabolized by CYP3A4.

The present invention provides novel Sulfonamide Derivatives of Formula (I) that inhibit CYP3A. Uses of the compounds of Formula (I) described herein include inhibiting CYP3A, which may be useful for increasing the pharmacokinetics of compounds that are metabolized by CYP3A.

Inhibition of CYP3A4

The present invention provides methods for inhibiting CYP3A4 in a subject, said method comprising administering to said subject a Sulfonamide Derivative, or pharmaceutically acceptable salt thereof, in an amount that is effective to inhibit CYP3A4 in said subject.

The present invention also provides methods that may be, or are believed to be, useful for inhibiting other members of CYP3A in a subject, said method comprising administering to said subject a Sulfonamide Derivative, or pharmaceutically acceptable salt thereof, in an amount that is effective to inhibit CYP3A in said subject. In one embodiment, the CYP3A being inhibited is CYP3A5. In another embodiment, the CYP3A being inhibited is CYP3A7. In another embodiment, the CYP3A being inhibited is CYP3A743.

Improving the Pharmacokinetics of a Therapeutic Compound that is Metabolized by CYP3A4

The present invention provides methods for improving the pharmacokinetics of a therapeutic compound that is metabolized by CYP3A4, comprising administering to a subject in need of such treatment an effective amount of a combination of said therapeutic compound and a Sulfonamide Derivative or pharmaceutically acceptable salt thereof.

The present invention also provides methods that may be, or are believed to be, useful for improving the pharmacokinetics of a therapeutic compound that is metabolized by other members of CYP3A, comprising administering to a subject in need of such treatment an effective amount of a combination of said therapeutic compound and a Sulfonamide Derivative or pharmaceutically acceptable salt thereof. In one embodiment, the therapeutic compound is metabolized by CYP3A5. In another embodiment, the therapeutic compound is metabolized by CYP3A7. In another embodiment, the therapeutic compound is metabolized by CYP3A743.

In one embodiment, the therapeutic compound whose pharmacokinetics are being improved is an anti-HIV drug.

In another embodiment, the therapeutic compound whose pharmacokinetics are being improved is an HIV protease inhibitor.

In still another embodiment, th the therapeutic compound whose pharmacokinetics are being improved is an HIV integrase inhibitor.

In another embodiment, the therapeutic compound whose pharmacokinetics are being improved is a nucleoside reverse transcriptase inhibitor (nRTI).

In yet another embodiment, the therapeutic compound whose pharmacokinetics are being improved is a non-nucleoside reverse transcriptase inhibitor (nnRTI).

Treatment or Prevention of HIV Infection

The present invention provides methods for treating or preventing HIV infection in a subject comprising administering to the subject: (i) a Sulfonamide Derivative or a pharmaceutically acceptable salt thereof and (ii) one or more anti-HIV drugs, wherein the amounts administered are together effective to treat or prevent HIV infection in said subject. In one embodiment, the present invention also provides methods for treating AIDS in a subject comprising administering to the subject: (i) a Sulfonamide Derivative or a pharmaceutically acceptable salt thereof and (ii) one or more anti-HIV drugs, wherein the amounts administered are together effective to treat AIDS in said subject.

The compositions and combinations of the present invention can be useful for treating a subject suffering from infection related to any HIV genotype.

In one embodiment, the HIV infection being treated is HIV-1.

In another embodiment, the HIV infection being treated is HIV-2.

In another embodiment, the HIV infection being treated has transformed into AIDS.

Combination Therapy

When administering a combination of a Sulfonamide Derivative and one or more anti-HIV drugs to a subject, the Sulfonamide Derivative and anti-HIV drug may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Sulfonamide Derivative and the anti-HIV drug(s) may be present in fixed amounts (dosage amounts) in a single dosage unit (e.g., a capsule, a tablet, and the like).

In one embodiment, the Sulfonamide Derivative is administered during a time when the anti-HIV drug(s) exert their prophylactic or therapeutic effect, or vice versa.

In another embodiment, the Sulfonamide Derivative and the anti-HIV drug(s) are administered in doses commonly employed when such agents are used as monotherapy for treating a viral infection.

In another embodiment, when administered in combination with a Sulfonamide Derivative, the anti-HIV drug(s) are administered in doses lower than the doses commonly employed when such agents are used as monotherapy for treating HIV infection. A lower dosage or less frequent administration of the anti-HIV drug(s) may reduce the toxicity of therapy without reducing the efficacy of therapy.

In one embodiment, the at least one Sulfonamide Derivative and the anti-HIV drug(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In one embodiment, the administration of a Sulfonamide Derivative and the anti-HIV drug(s) may inhibit the resistance of the HIV infection to one or more of the agents being administered.

Anti-HIV Drugs

An "anti-HIV drug," as defined herein, is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV drug is effective in treating, preventing, or delaying the onset or progression of HIV infection or AIDS and/or diseases or conditions arising therefrom or associated therewith. For example, the Sulfonamide Derivatives of Formula (I) can be effectively administered, whether at periods of pre-exposure and/or post-exposure, in combination with effective amounts of one or more anti-HIV drugs selected from anti-HIV drugs, immunomodulators, antiinfectives, useful for treating HIV infection or AIDS. Suitable HIV antivirals for use in combination with the compounds of the present invention include, for example, those listed in Table A below.

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |

TABLE A-continued

| Name | Type |
| --- | --- |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, atazanavir, elvitegravir and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are atazanavir and raltegravir.

In still another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV drugs selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV drugs selected from raltegravir, lamivudine, abacavir, atazanavir, darunavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV drugs is not limited to the HIV antivirals listed in Table A, but includes in principle any combination with any drug or pharmaceutical composition useful for the treatment or prophylaxis of AIDS. The anti-HIV drugs and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Sulfonamide Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

Due to their activity, the Sulfonamide Derivatives are useful in veterinary and human medicine. As described above, the Sulfonamide Derivatives are useful for: inhibiting CYP3A4; improving the pharmacokinetics of a therapeutic compound that is metabolized by CYP3A4; and in combination with one or more anti-HIV agents for treating or preventing HIV infection in a subject in need thereof.

When administered to a subject, the Sulfonamide Derivatives can be administered as a component of a composition that comprises a pharmaceutically acceptable carrier or vehicle. The present invention provides pharmaceutical compositions comprising an effective amount of at least one Sulfonamide Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Sulfonamide Derivatives are administered orally.

In another embodiment, the Sulfonamide Derivatives are administered intravenously.

In one embodiment, the present invention provides compositions comprising a Compound of Formula (I) or a pharmaceutically acceptable salt thereof, and a pharmaceutically acceptable carrier.

In one embodiment, a pharmaceutical preparation comprising at least one Sulfonamide Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Sulfonamide Derivative(s) by weight or volume. In various embodiments, the present compositions can contain, in one embodiment, from about 1% to about 70% or from about 5% to about 60% of the Sulfonamide Derivative(s) by weight or volume.

The Sulfonamide Derivatives can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Sulfonamide Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) a Compound of Formula (I) or a pharmaceutically acceptable salt thereof; (ii) a therapeutic compound that is metabolized by CYP3A4; and (iii) a pharmaceutically acceptable carrier. In another embodiment, the present invention provides compositions comprising: (i) a Compound of Formula (I) or a pharmaceutically acceptable salt thereof; (ii) one or more anti-HIV drugs; and (iii) a pharmaceutically acceptable carrier, wherein the amounts in the composition are together effective to treat HIV infection.

In another embodiment, the present invention provides compositions comprising a Compound of Formula (I) or a pharmaceutically acceptable salt thereof, a pharmaceutically acceptable carrier, and one or more anti-HIV drugs, wherein said anti-HIV drugs are selected from raltegravir, lamivudine, abacavir, atazanavir, darunavir, lopinavir and ritonavir.

In still embodiment, the present invention provides compositions comprising a Compound of Formula (I) or a pharmaceutically acceptable salt thereof, a pharmaceutically acceptable carrier, and raltegravir.

Kits

In one aspect, the present invention provides a kit comprising a therapeutically effective amount of at least one Sulfonamide Derivative, or a pharmaceutically acceptable salt, solvate, ester or prodrug of said compound and a pharmaceutically acceptable carrier, vehicle or diluent.

In another aspect the present invention provides a kit comprising an amount of at least one Sulfonamide Derivative, or a pharmaceutically acceptable salt, solvate, ester or prodrug of said compound and a therapeutic compound that is metabolized by CYP3A4. In one embodiment, the Sulfonamide Derivatives and the therapeutic compound that is metabolized by CYP3A4 are provided in the same container. In one embodiment, the Sulfonamide Derivatives and the therapeutic compound that is metabolized by CYP3A4 are provided in separate containers.

In another aspect the present invention provides a kit comprising an amount of at least one Sulfonamide Derivative, or a pharmaceutically acceptable salt, solvate, ester or prodrug of said compound and an amount of at least one anti-HIV drug listed above, wherein the amounts of the two or more active ingredients result in a desired therapeutic effect. In one embodiment, the Sulfonamide Derivatives and the one or more anti-HIV drugs are provided in the same container. In one embodiment, the Sulfonamide Derivatives and the one or more anti-HIV drugs are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-L below. Alternative synthetic pathways and analogous structures will be apparent to those skilled in the art of organic synthesis.

Scheme A shows methods useful for making compounds of formula A6, which are useful intermediates for the synthesis of compounds of Formula (I), wherein Q is carbon.

Scheme A

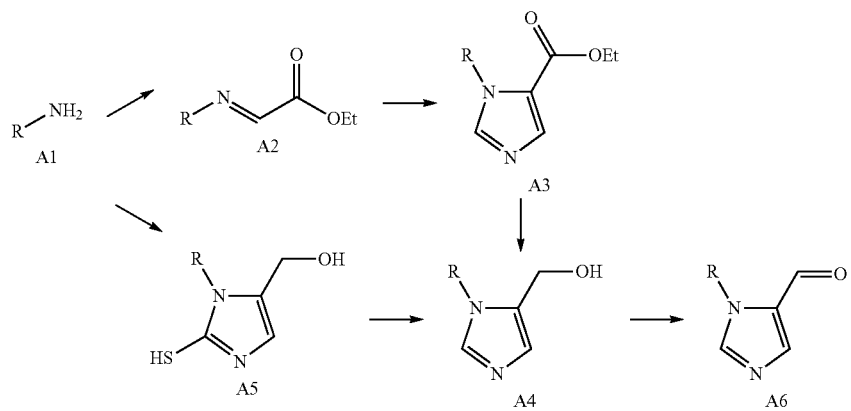

Amines of formula A1 can be condensed with an aldehyde to provide intermediates of formula A2 which can undergo a cyclization reaction with a reagent such as TosMIC to provide compounds f formula A3. Intermediate A3 can subsequently be reduced with a hydride reducing agent such as $LiBH_4$ to provide carbinols of formula A4. Compounds f formula A4 can alternatively be prepared in a two-step procedure involving the condensation of amine A1 with 1,3-dihydroxyacetone dimer and KSCN to provide the thioimidazole compounds of formula A5 which can then be oxidized with a reagent such as hydrogen peroxide to provide intermediate A4. Primary alcohols of formula A4 can then be oxidized with reagents such as $MnO_2$ to provide the key intermediates of formula A6.

Scheme B shows methods useful for making the compounds of formula B3, which are useful intermediates for the synthesis of compounds of Formula (I), wherein Q is nitrogen.

Scheme B

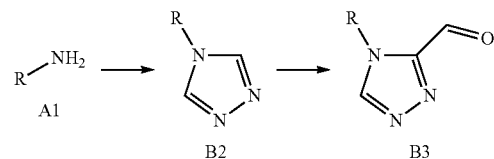

Amines of formula A1 can be cyclocondensed with 1,2-diformylhydrazine to provide 1,2,4-triazoles of formula B2 which can subsequently be converted to the aldehydes of formula B3 using standard formylation reagents, such as DMF and POCl₃.

Scheme C shows methods useful for making the compounds of formula C5, which correspond to the compounds of Formula (I), wherein Q is carbon and X is a substituted carbon.

Scheme C

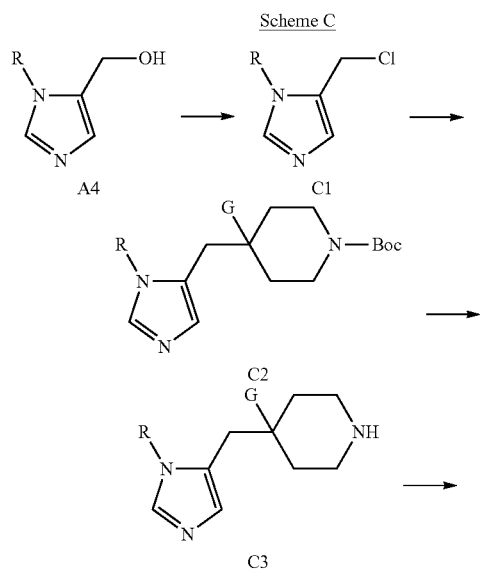

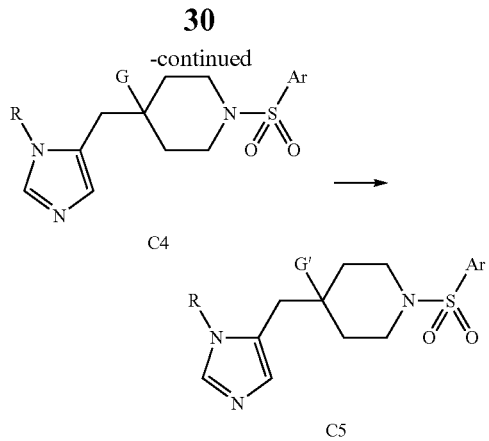

Carbinols of formula A4 can be activated for alkylation of a piperidine derivative by conversion to the chloride C1 which can then be added to the anion of a 4-substituted piperidine in which the G group is an anion stabilizing group such as nitrile or ester. Deprotection of the piperidine nitrogen can afford compounds of formula C3 which can be sulfonylated to provide compounds of formula C4. The G group may undergo further modification using standard functional group transforming reactions to provide analogs of formula C5.

Scheme D shows methods useful for making compounds of formulas D3, D6 and D9, which correspond to the compounds of Formula (I), wherein Q is carbon; X is hydroxy or ether; and Y is H, alkyl or trifluoromethyl.

Scheme D

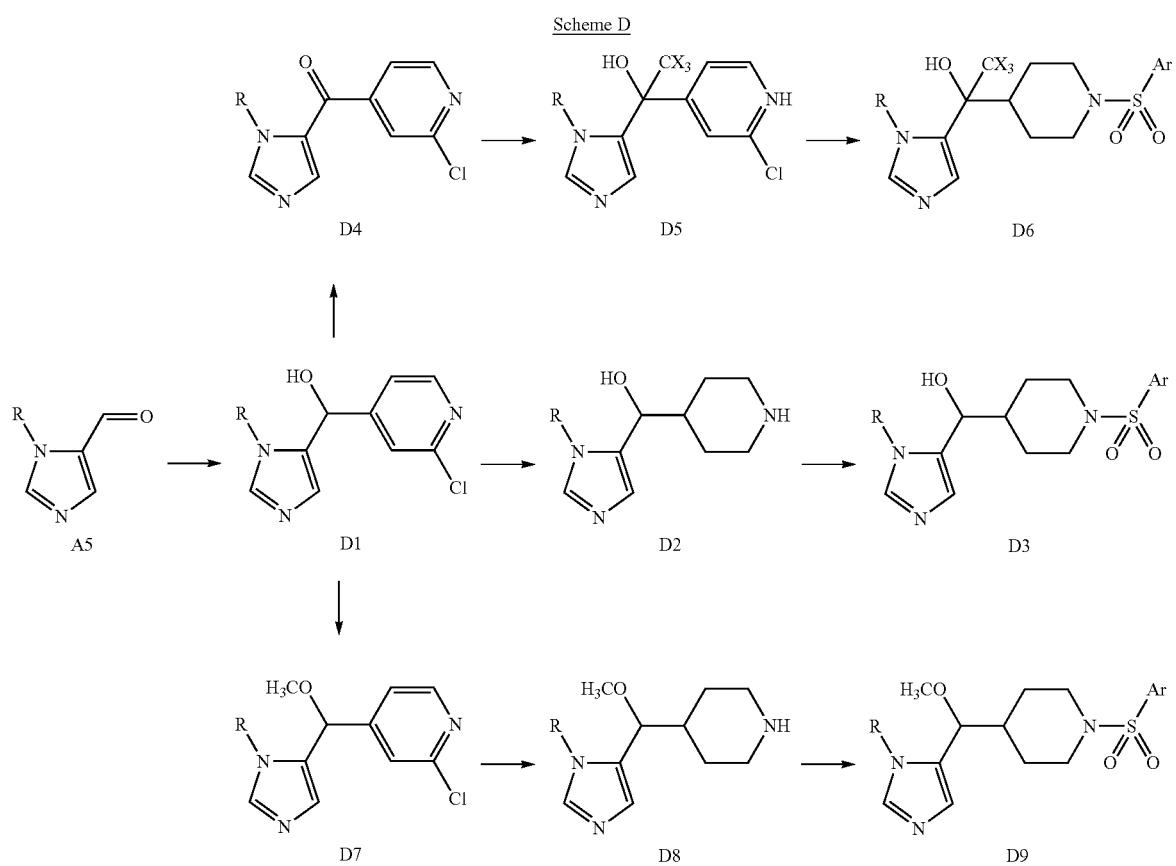

Aldehydes of formula A5 can be reacted with the anion of 2-chloro-4-methylpyridine to provide carbinol D1 which can be reduced using hydrogenating conditions and a catalyst such as PtO$_2$ to provide piperidine compounds of formula D2. A compound of formula D2 can then be sulfonylated with an appropriately substituted arylsulfonyl chloride and a base such as triethylamine to provide the compounds of formula D3. Additionally, carbinols of formula D1 can be oxidized with a reagent such as MnO$_2$ to the ketones of formula D4 which can then be treated with methyl (X=H) or trifluoromethyl (X=F) nucleophiles to provide D5 which can be hydrogenated and sulfonylated to provide compounds of formula D6. Alternatively, carbinols of formula D1 can be alkylated using a metal hydride base and electrophile, such as CH$_3$I to provide ethers D7 which can be converted to compounds of formula D9 using chemistry described for the synthesis of the compounds of formulas D3 and D6.

Scheme E shows methods useful for making compounds of formulas E3 and E6, which correspond to the compounds of Formula (I), wherein Q is carbon and X is carbon which can be linked to Z through a —CH$_2$— bridge.

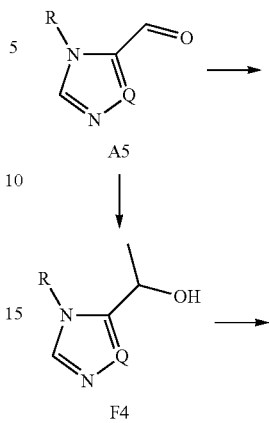

Scheme F

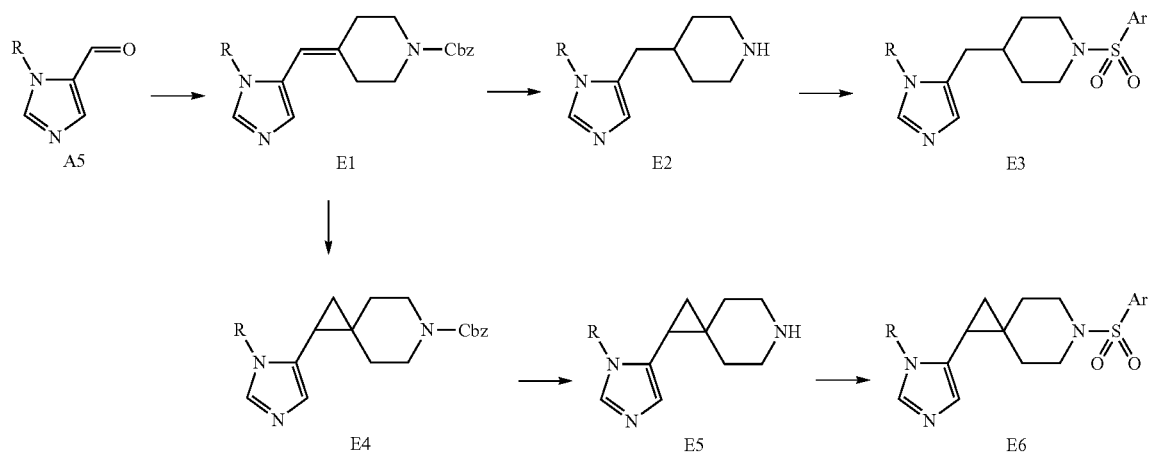

Scheme E

Aldehydes of formula A5 can undergo a McMurray coupling reaction with an appropriately substituted 4-piperidinone derivative using reagents such as zinc dust and titanium(IV)chloride to provide olefins of formula E1 which can be reduced and deprotected using hydrogenation conditions with a catalyst such as Pd(OH)$_2$ to provide piperidines of formula E2. Standard conditions for the sulfonylation of secondary amines (ArSO$_2$Cl, Et$_3$N) can be used to provide targets of formula E3. Alternatively, olefins of formula E1 can be cyclopropanated using well-known chemistry (such as (CH$_3$)$_3$S$^+$I$^-$ and NaH) to provide the spirocycles of formula E4 which can then be converted to the desired compounds of formula E6 using conditions similar to those described for the preparation of compounds of formula E3.

Scheme F shows methods useful for making compounds of formula F3 and F7, which correspond to the compounds of Formula (I), wherein Q is carbon or nitrogen; X is nitrogen; and Z is H or methyl.

-continued

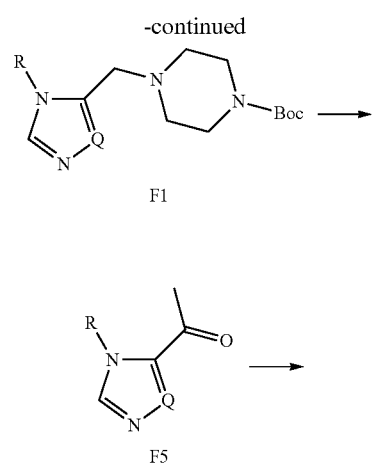

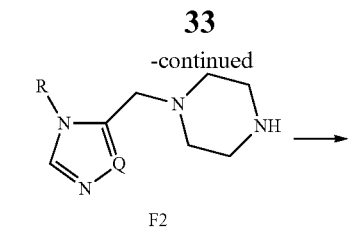

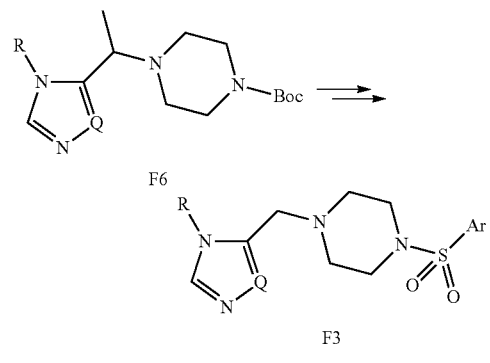

Aldehydes of formula A5 can be reductively aminated with a piperazine derivative using standard conditions using a dehydrating agent such as Ti(OiPr)$_4$ and a reducing agent such as NaBH(OAc)$_3$ to provide intermediates of formula E1 which can subsequently be deprotected and sulfonylated to provide targets of formula E3 using conditions described in the schemes above. Aldehyde A5 can also be converted to the secondary alcohols of formula E4 by reaction with a methyl nucleophile such as CH$_3$MgBr. Ketone E5 can be formed from oxidizing E4 with an oxidizing agent such as MnO$_2$ which can then undergo reductive amination, deprotection, and sulfonylation following chemistry described above to provide analogs of formula E7.

Scheme G shows methods useful for making compounds of formula G2, which correspond to the compounds of Formula (I), wherein B is carbon and Z is CN.

Scheme G

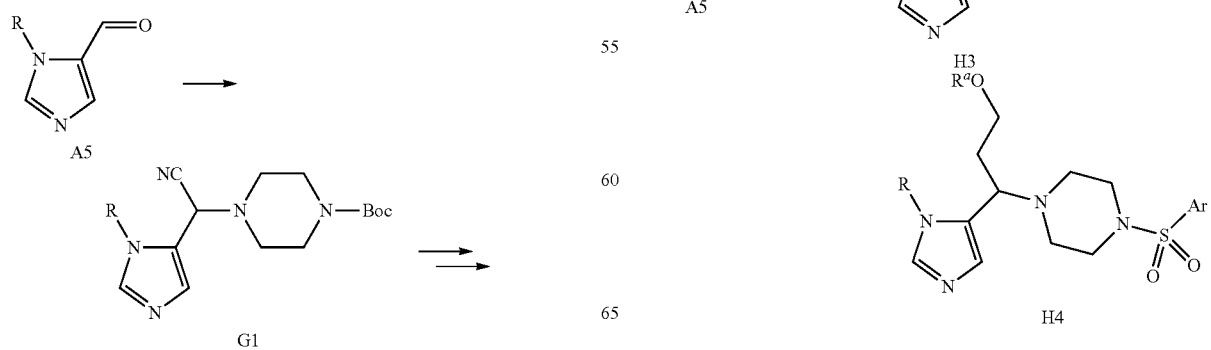

Aldehydes of formula A5 can be converted to the alpha-aminonitriles of formula G1 using a suitably protected piperazine and a cyanide source such as KCN. Compounds of formula G2 can be obtained after deprotection of the Boc group and sulfonylation of the resulting amine using standard conditions (such as ArSO$_2$Cl and Et$_3$N) to provide targets of formula G2.

Scheme H shows methods useful for making compounds of formula H2 and H4, which correspond to the compounds of Formula (I), wherein B is carbon; X is nitrogen; and Z is (CH$_2$)$_n$OR$^a$ wherein n is 1 or 2.

Scheme H

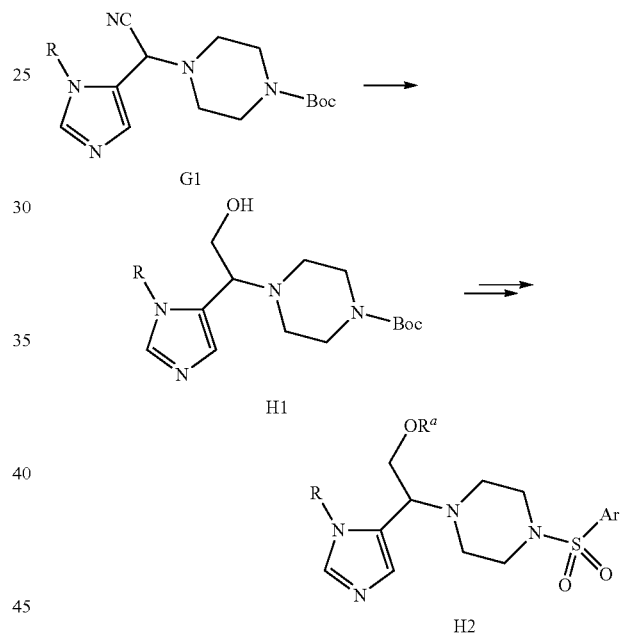

Nitriles of formula G1 can be converted to its carboxylic ester then reduced using standard conditions. The resulting alcohol can be alkylated to intermediates of formula H2 (R$^a$=alkyl) using standard conditions or converted to the compounds of formula H2 after deprotection of the Boc group and sulfonylation of the resulting amine using standard conditions such as ArSO$_2$Cl and a tertiary amine base. Alternatively, aldehydes of formula A5 can be olefinated using standard Horner-Emmons chemistry to provide the unsaturated esters of formula H3 which can then undergo a Michael addition with a suitably protected piperazine analog to provide a β-substituted ester which can subsequently be reduced using known conditions for the reduction of esters to primary alcohols such as LiBH$_4$. The resulting alcohol can be further functionalized to the compounds of formula H4 using methods described above.

Scheme I shows methods useful for making compounds of formula I5, which correspond to the compounds of Formula (I), wherein Q is carbon; X is nitrogen; and R$^1$ and Z are joined to form a —CH$_2$OCH$_2$— bridge.

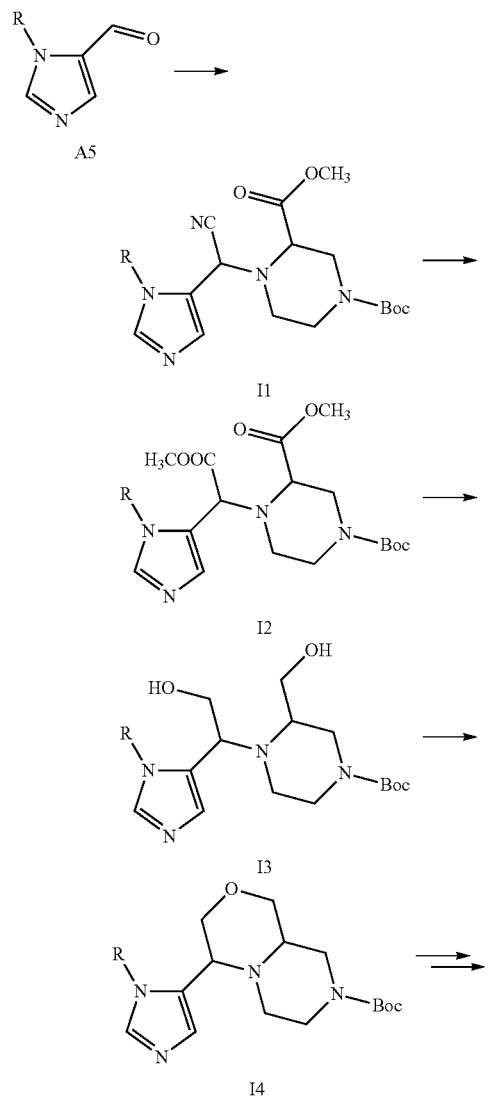

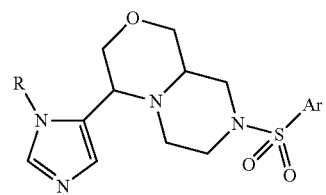

Aldehyde A5 can be converted to the nitrile ester I1 using chemistry described for the preparation of G1. Nitrile I1 can be transformed to the diester analog I2 under acidic conditions which can then be converted to diol I3 using a hydride reducing agent such as LiBH$_4$. Ring closure to provide compounds of formula I4 can be affected by activating one of the alcohol functional groups with a reagent such as toluene sulfonyl chloride followed by deprotonating the second alcohol with a metal hydride base such as NaH. Final targets of formula I5 can be obtained after deprotection of the Boc group and sulfonylation of the resulting piperazine amine using standard conditions such as ArSO$_2$Cl and a tertiary amine base.

Scheme J shows methods useful for making compounds of formula J5, which correspond to the compounds of Formula (I), wherein Q is carbon; X is nitrogen; and R$^1$ and Z are joined to form a —CH$_2$CH$_2$CH$_2$— bridge.

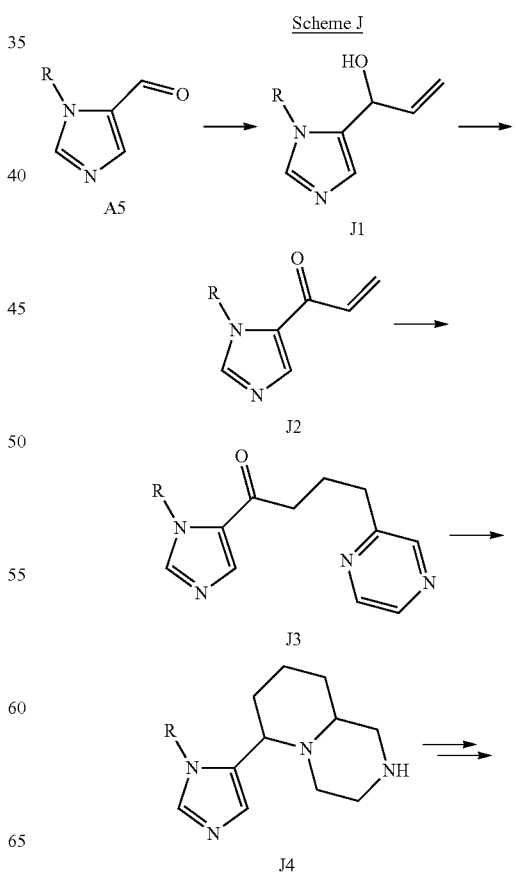

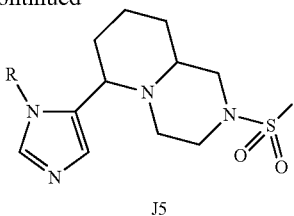

Aldehydes of formula A5 can be converted to the α,β-unsaturated ketones of formula J2 by a standard two-step procedure involving the addition of a vinyl Grignard reagent and oxidation of the resulting carbinol with a reagent such as MnO₂. Intermediates of formula J2 can undergo a Michael addition with the anion derived from metallating 2-methyl-1,4-pyrazine to form ketones of formula J3 which can then undergo reductive cyclization after treatment with a metal catalyst under a hydrogen atmosphere. Standard methodology for sulfonylating secondary amines can give targets of formula J5.

Scheme K shows methods useful for making compounds of formula K3, which correspond to the compounds of Formula (I), wherein Q is carbon; X is nitrogen; and R¹ and Z are joined to form a —CH₂OC(=O)— bridge.

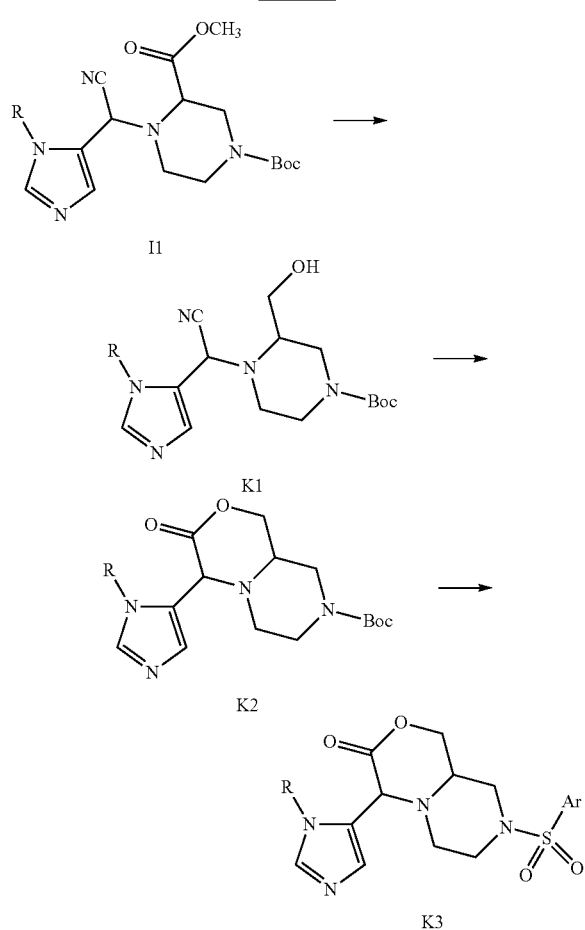

Carboxylic esters of formula I1 can be reduced to the corresponding primary alcohols of formula K2 with reagents such as LiBH₄ which can then undergo a lactonization reaction to provide intermediates of formula K2 upon treatment with a strong base such as KOH. Final targets K3 can be obtained after deprotection of the Boc group and sulfonylation of the resulting piperazine amino group using standard conditions (such as ArSO₂Cl and a tertiary amine base).

Scheme L shows methods useful for making the intermediates of formula L2 and L4, which correspond to the compounds of Formula (I), wherein Q is carbon; X is nitrogen; and R¹ and Z are joined to form a —C(=O)NRᵃCH₂— lactam bridge or a —CH₂N(CH₃)CH₂— amine bridge.

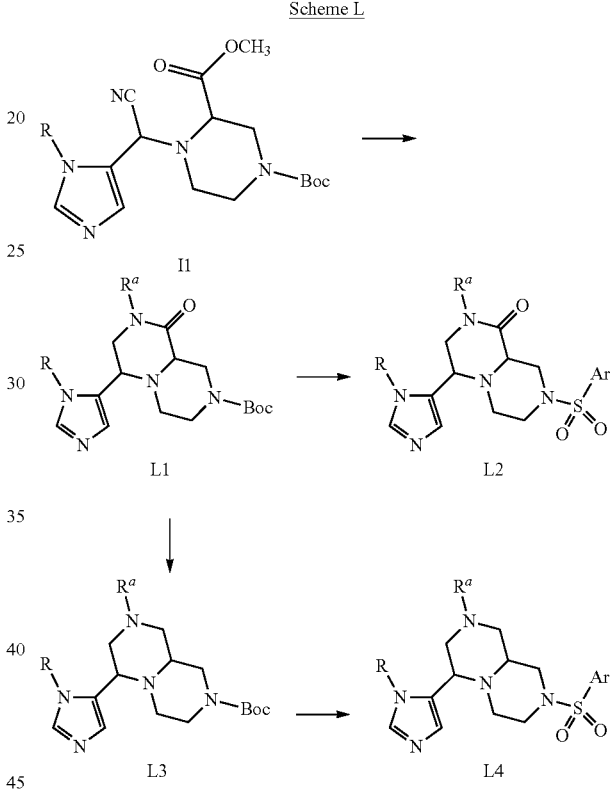

Nitriles of formula I1 can undergo reductive lactamization using known conditions for the conversion of a nitrile to a primary amine such as catalytic hydrogenation using a metal such as nickel as the catalyst. The resulting lactam NH can be alkylated to intermediates of formula L1 (Rᵃ=alkyl) using standard conditions or converted to the final targets of formula L2 (Rᵃ=H) using methods described above. Alternatively, intermediate lactams of formula L1 can be reduced to triamines of formula L3 using a metal hydride reagent such as LiAlH₄. Final targets of formula L4 can be obtained after deprotection of the Boc group and sulfonylation of the resulting amine using standard conditions (such as ArSO₂Cl and a tertiary amine base).

One skilled in the art of organic synthesis will recognize that the synthesis of the Compounds of Formula (I) may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

The preparation of some intermediates useful for making the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The Compounds Formula (I) may contain one or more silicon atoms. The compounds contemplated in this invention in general can be prepared using the carba-analog methodology unless otherwise noted. A recent review of the synthesis of silicon containing compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, *J. Am. Chem. Soc.*, 128:8479 (2006)) and reduced metabolic processing of silyl containing compounds have been described (Johansson et al., *Drug Metabolism & Disposition*, 38:73 (2009)).

The starting materials used and the intermediates prepared using the methods set forth in Schemes A-L may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound 1

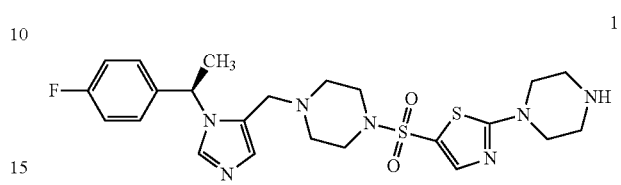

Step A—Preparation of Int 1-1

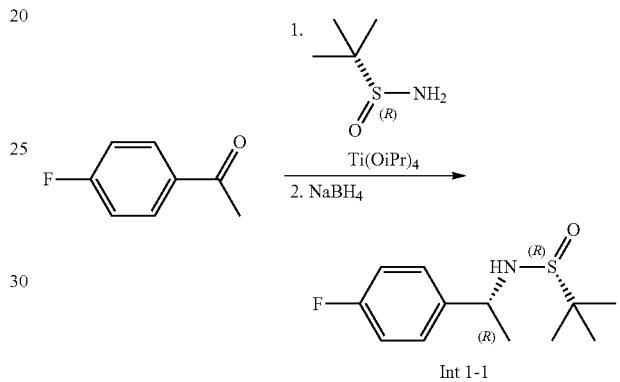

To a solution of 1-(4-fluoro-phenyl)-ethanone (400 g, 2.9 mol) and 2-methylpropane-2-sulfinic acid amide (350 g, 2.9 mol) in THF (4 L) was added Ti(OiPr)$_4$ (824 g, 2.9 mol). The reaction mixture was allowed to stir at 90° C. for 48 hours when TLC (PE:EA=10:1) showed the reaction was complete. The mixture was cooled to 0° C. and NaBH$_4$ (110 g, 209 mol) was added in portions. The reaction was allowed to stir at 0° C. until TLC (petroleum ether/EtOAc=1:1) showed the reaction was complete (~1 hour). The reaction mixture was poured into ice water and the formed precipitate was filtered and washed with ethyl acetate. The filtrate was concentrated in vacuo dissolved into water and the aqueous layer was extracted with ethyl acetate (800 mL×3), dried over anhydrous Na$_2$SO$_4$ and concentrated in vacuo to provide the resulting residue Int 1-1, which was purified using silica gel column. (350 g, 50 MS (ESI) m/z (M+1): 244.

Step B—Preparation of Int 1-2

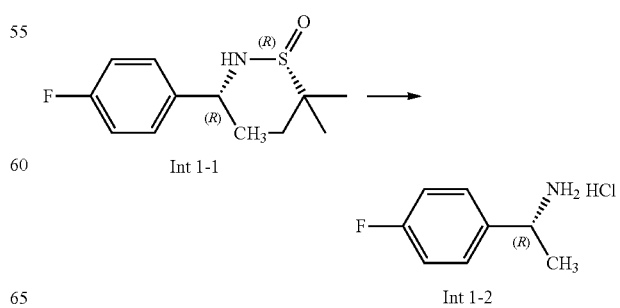

To a solution of compound Int 1-1 (350 g, 1.44 mol) in 500 mL of ethyl acetate was added HCl/EtOAc (700 mL, 4 M) in portions at 0° C. Within 30 minutes white solid was formed and TLC (petroleum ether:EtOAc=1:1) showed the reaction to be complete. The precipitate was filtered and washed with ethyl acetate. The filter cake was dried to provide 200 g (79%) of compound Int 1-2 as white powder. MS (ESI) m/z (M+1): 140.

Step C—Preparation of Int 1-4

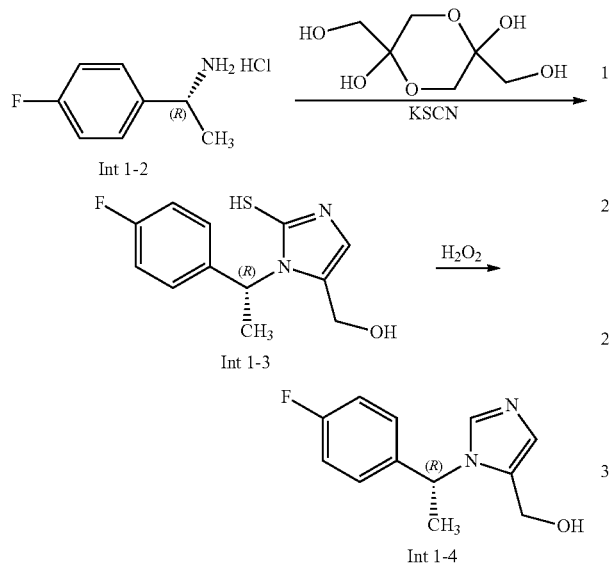

To a solution of compound Int 1-2 (200 g, 1.14 mol) in 2 L of 50% aqueous acetonitrile was added $K_2CO_3$ to adjust the solution to pH 8. Acetic acid (50 mL) was then added and the reaction was allowed to stir for 20 min before 1,3-dihydroxyacetone dimer (205 g, 1.14 mol) and KSCN (111 g, 1.14 mol) was added. The reaction mixture was allowed to stir at 9° C. for 5 hours when TLC (petroleum ether:EtOAc=1:2) showed the reaction to be complete. The reaction mixture was then cooled to 0° C. and $H_2O_2$ (388 mL, 30%, 3.42 mol) was added dropwise. The mixture was allowed to stir at 0° C. for 1 hour, then the reaction mixture was quenched with saturated $Na_2SO_3$ at 0° C. Solid $Na_2CO_3$ was added to the mixture to adjust to pH 8~10 and the solid was filtered off. The remained aqueous filtrate was extracted with ethyl acetate and the combined organic extracts were dried over $Na_2SO_4$, filtered and concentrated in vacuo to provide compound Int 1-4 (90 g), which was used in next step without further purification. MS (ESI) m/z (M−17): 203; (M+1): 221.

Step D—Preparation of Int 1-5

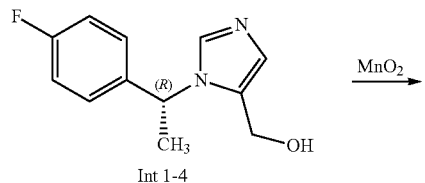

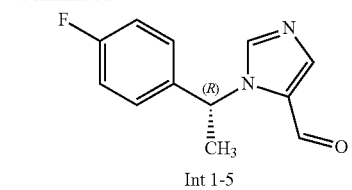

To a solution of compound Int 1-4 (90 g, 0.41 mmol) in dioxane (1 L) was added $MnO_2$ (107 g, 1.23 mol) and the mixture was allowed to stir at 80° C. for 5 hours. The reaction mixture was filtered through Celite and the filtrate was concentrated in vacuo. The resulting residue was purified using column chromatography (1:1 petroleum ether/EtOAc) to provide 70 g (79%) of compound Int-1 as yellow oil. MS (ESI) m/z (M+1): 219.

Step E—Preparation of Int 1-6

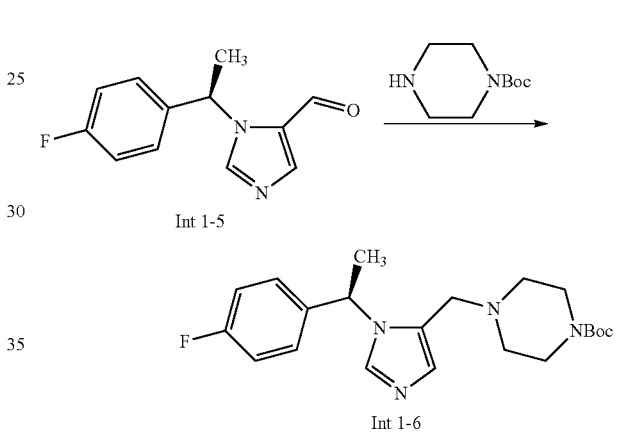

To a stirred solution of compound Int 1-5 (4.0 g, 18 mmol) in THF (40 mL) was added N-Boc piperazine (3.58 g, 19 mmol). The mixture was allowed to stir at room temperature for 1 hour. $NaBH(OAc)_3$ (11.3 g, 54 mmol) was added in portions and the reaction was allowed to stir at room temperature for about 15 hours. The reaction mixture was washed with water and extracted with ethyl acetate (3×20 mL). The combined organic extracts were washed with brine, dried over $Na_2SO_4$, filtered and concentrated in vacuo. The resulting yellow oily residue was purified using column chromatography on silica gel with $CH_2Cl_2$:MeOH=100:1 to provide 5.9 g of compound Int 1-6 as yellow solid. Yield: 85%. MS (ESI) m/z (M+1): 389.

Step F—Preparation of Int 1-7

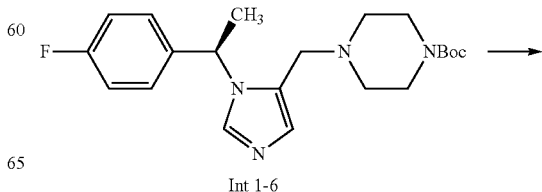

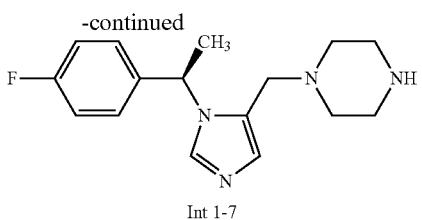

Int 1-7

A mixture of compound Int 1-6 (5.9 g, 15 mmol) in HCl/EtOAc (50 mL) was allowed to stir at room temperature for 2 hours then concentrated in vacuo and used in the next step without further purification. MS-ESI (m/z): 289 (M+1)+

Step G—Preparation of Int 1-8

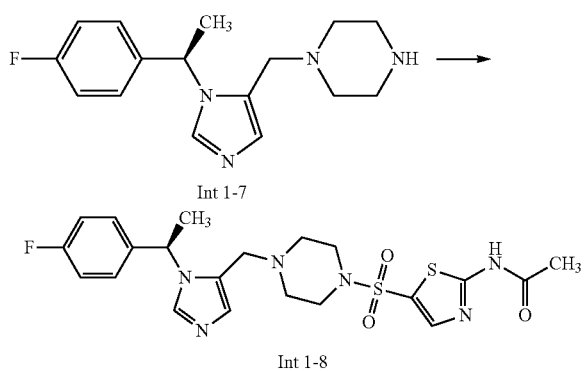

To a stirred solution of compound Int 1-7 (5.0 g, 0.015 mol) in 50 mL of $CH_2Cl_2$ was added triethylamine (6.25 mL, 0.045 mol) was added N-acetyl-2-aminothiazole-5-sulfonyl chloride (4.8 g, 0.02 mol) at room temperature. The reaction was allowed to stir for 2 hours then the reaction mixture was concentrated in vacuo. The resulting residue was purified using column chromatography on silica gel with $CH_2Cl_2$: MeOH=50:1 to provide 3.9 g of compound Int 1-8 as yellow solid. Yield: 45%. MS (ESI) m/z (M+1): 492.

Step H—Preparation of Int 1-9

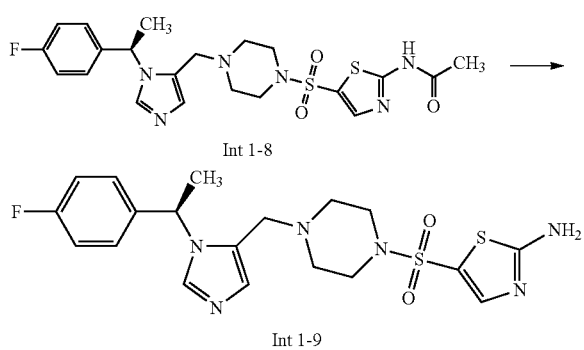

To a stirred solution of compound Int 1-8 (3.9 g, 7.9 mmol) in 40 mL of ethanol was added 6M HCl (40 mL). The mixture was heated to 80° C. and allowed to stir at this temperature for 12 hours. The reaction mixture was concentrated in vacuo and the resulting residue was covered with saturated aqueous $NaHCO_3$, extracted with EtOAc, dried over sodium sulfate, filtered and in vacuo. The resulting residue was used in the next step without further purification. $^1$H NMR δ 9.22 (s, 1H), 7.55 (s, 1H), 7.40 (s, 1H), 7.23~7.20 (m, 2H), 7.06~7.01 (m, 2H), 5.91 (t, J=6.8 Hz, 1H), 3.62 (d, J=14.4 Hz, 1H), 3.40 (d, J=14.4 Hz, 1H), 2.92 (m, 2H), 2.82 (m, 2H), 2.50 (m, 2H), 2.42 (m, 2H), 1.86 (d, J=6.8 Hz, 3H). MS-ESI (ESI) m/z (M+1): 451

Step I—Preparation of Int 1-10

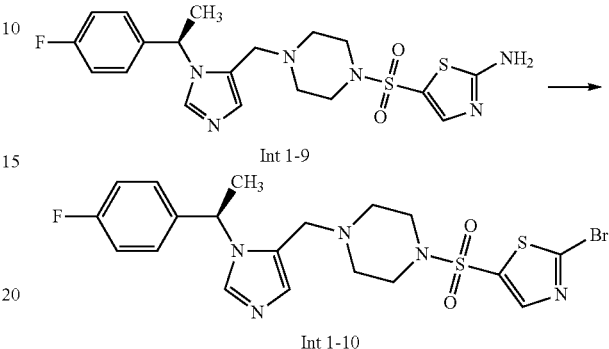

To a stirred mixture of CuBr (1.2 g, 8.35 mmol) and t-BuNO$_2$ (0.89 mL, 6.68 mmol) in 4 mL of $CH_3CN$ was added compound Int 1-9 (1.5 g, 3.34 mmol) in 50 mL of $CH_3CN$ in portions. The mixture was heated to 60° C. and allowed to stir at this temperature for 17 hours then cooled to room temperature and concentrated in vacuo. The resulting residue was purified using column chromatography with 1:2 EtOAc/hexanes to provide 0.6 g (35%) of compound Int 1-10 as a brown solid. MS (ESI) m/z (M+1): 513

Step J—Preparation of Compound 1

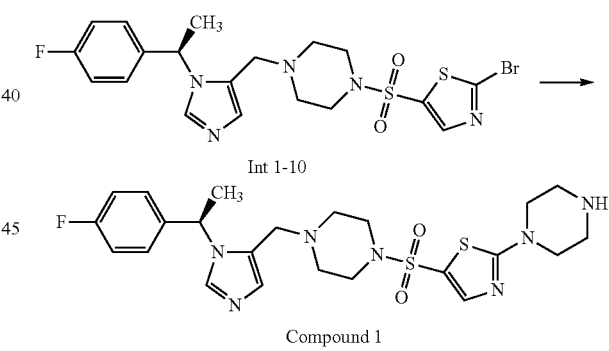

To a stirred solution of compound Int 1-10 (200 mg, 0.39 mmol) in 4 mL of DMA was added $K_2CO_3$ (161 mg, 1.17 mmol) followed by piperazine (40 mg, 0.47 mmol). The mixture was allowed to stir at 120° C. for 3 hours. The reaction mixture was then concentrated in vacuo and the resulting residue was purified using HPLC to provide 10 mg (26%) of Compound 1 as a white solid. $^1$H NMR (CD$_3$OD) δ 9.26 (s, 1H), 7.59 (s, 1H), 7.55 (s, 1H), 7.18~7.16 (m, 2H), 7.01~6.97 (m, 2H), 5.87 (t, J=6.8 Hz, 1H), 3.87~3.85 (m, 4H), 3.67 (d, J=14.4 Hz, 1H), 3.40~3.37 (m, 4H), 3.35 (d, J=14.4 Hz, 1H), 2.85 (m, 2H), 2.70 (m, 2H), 2.47 (m, 2H), 2.37 (m, 2H), 1.86 (d, J=6.8 Hz, 3H). MS-ESI (ESI) m/z (M+1): 520

The following compounds were prepared as described in step J above starting from Int 1-10.

| No. | Structure | M + 1 | ¹H NMR |
|---|---|---|---|
| 2 | 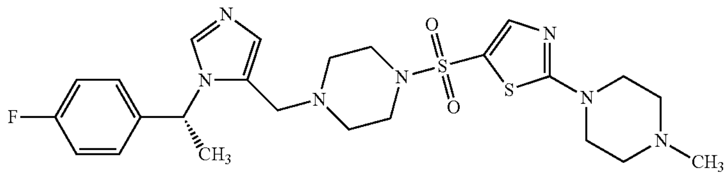 [SMILES: C[C@H](c1ccc(F)cc1)n1cncc1CN1CCN(S(=O)(=O)c2cnc(N3CCN(C)CC3)s2)CC1] | 534 | (CD$_3$OD) δ 7.92 (s, 1H), 7.51 (s, 1H), 7.11~7.05 (m, 1H), 6.93~6.87 (m, 3H), 5.61 (q, J = 6.8 Hz, 1H), 3.61 (m, 4H), 3.53~3.50 (m, 1H), 3.25~3.22 (m, 1H), 2.82 (s, 1H), 2.68 (s, 2H), 2.58-2.57 (m, 4H), 2.39~2.34 (m, 7H), 1.78 (d, J = 6.8 Hz, 3H). |
| 3 | 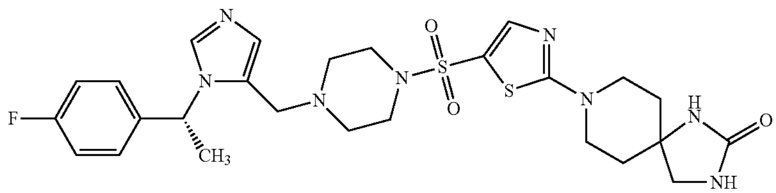 [SMILES: C[C@H](c1ccc(F)cc1)n1cncc1CN1CCN(S(=O)(=O)c2cnc(N3CCC4(CC3)CNC(=O)N4)s2)CC1] | 590 | (CD3OD) δ: 9.25 (s, 1H), 7.56-7.54 (m, 2H), 7.20-7.17 (m, 2H), 7.02-6.98 (m, 2H), 5.88 (q, J = 6.8 Hz, 1H), 4.68 (d, J = 6.8 Hz, 2H), 4.01 (d, J = 5.2 Hz, 2H), 3.74 (d, J = 3.6 Hz, 2H), 3.67 (d, J = 14.4 Hz, 1H), 3.38 (d, J = 14.4 Hz, 1H), 2.88 (bs, 2H), 2.75 (bs, 2H), 2.49 (bs, 2H), 2.40 (bs, 2H), 2.21 (bs, 2H), 2.06 (bs, 2H), 1.86 (d, J = 6.8 Hz, 3H) |
| 4 | 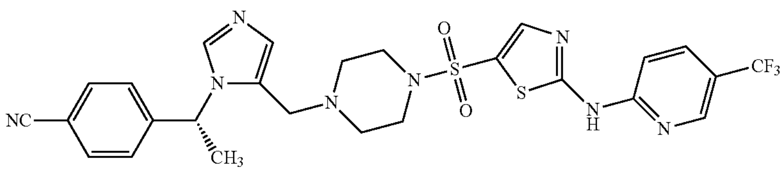 [SMILES: C[C@H](c1ccc(C#N)cc1)n1cncc1CN1CCN(S(=O)(=O)c2cnc(Nc3ccc(C(F)(F)F)cn3)s2)CC1] | 603 | (CD$_3$OD) δ 9.26 (s, 1H), 8.69 (s, 1H), 8.00 (d, J = 6.4 Hz, 1H), 7.80 (s, 1H), 7.56 (d, J = 8.4 Hz, 3H), 7.30 (d, J = 8.4 Hz, 2H), 7.20 (d, J = 8.4 Hz, 2H), 5.96 (q, J = 6.8 Hz, 1H), 3.65 (d, J = 14.4 Hz, 1H), 3.34 (d, J = 14.4 Hz, 1H), 2.94 (m, 2H), 2.81 (m, 2H), 2.53 (m, 2H), 2.44~2.42 (m, 2H), 1.84 (d, J = 6.8 Hz, 3H). |
| 6 | 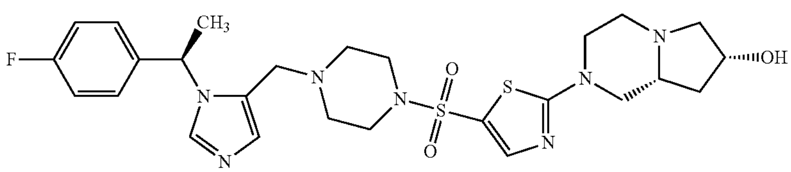 [SMILES: C[C@H](c1ccc(F)cc1)n1cncc1CN1CCN(S(=O)(=O)c2cnc(N3CCN4C[C@H](O)C[C@@H]4C3)s2)CC1] | 576 | (CD$_3$OD) δ 7.98 (s, 1H), 7.52 (s, 1H), 7.10-7.07 (m, 2H), 6.95-6.90 (m, 3H), 5.66-5.60 (q, J = 7.2, 1H), 4.38-4.34 (m, 1H), 4.14-4.10 (d, J = 13.6, 1H), 3.99-3.95 (d, J = 13.6, 1H), 3.55-3.52 (m, 1H), 3.39-3.35 (m, 1H), 3.27-3.24 (m, 1H), 3.13-3.11 (m, 1H), 3.09-3.01 (m, 2H), 2.84-2.83 (m, 2H), 2.70-2.69 (m, 2H), 2.43-2.27 (m, 7H), 2.19-2.15 (m, 1H), 1.80-1.78 (d, J = 7.6, 3H), 1.50-1.40 (m, 1H). |
| 7 | 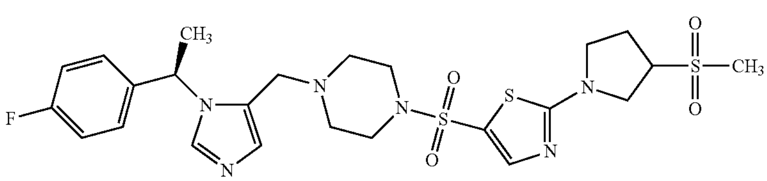 [SMILES: C[C@H](c1ccc(F)cc1)n1cncc1CN1CCN(S(=O)(=O)c2cnc(N3CCC(S(C)(=O)=O)C3)s2)CC1] | 583 | (CDCl3) δ 7.94-7.80 (m, 1H), 7.60 (s, 1H), 6.96-6.91 (m, 5H), 5.54-5.53 (q, J = 7.2, 1H), 4.09-4.06 (m, 1H), 4.05-3.96 (m, 1H), 3.94-3.87 (m, 1H), 3.85-3.76 (m, 1H), 3.65-3.59 (m, 1H), 3.34-3.31 (m, 1H), 3.23-3.20 (m, 1H), 2.99-2.88 (m, 7H), 2.75-2.68 (m, 1H), 2.58-2.53 (m, 1H), 2.43-2.37 (m, 4H), 1.81-1.80 (m, 3H). |
| 8 | 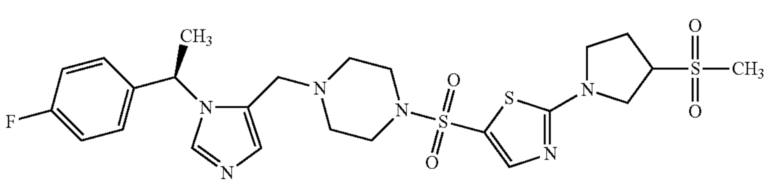 [SMILES: C[C@H](c1ccc(F)cc1)n1cncc1CN1CCN(S(=O)(=O)c2cnc(N3CCC(S(C)(=O)=O)C3)s2)CC1] | 583 | (CDCl3) δ 7.95-7.86 (m, 1H), 7.54 (s, 1H), 7.19 (s, 1H), 6.96-6.88 (m, 5H), 5.51-5.47 (q, J = 7.2 , 1H), 4.07-4.03 (m, 1H), 3.93-3.88 (m, 1H), 3.82-3.79 (m, 1H), 3.73-3.67 (m, 1H), 3.57-3.53 (m, 1H), 3.26-3.12 (m, 2H), 2.93-2.83 (m, 7H), 2.69-2.64 (m, 1H), 2.55-2.48 (m, 1H), 2.37-2.30 (m, 4H), 1.76-1.74 (d, J = 7.2, 3H). |

| No. | Structure | M + 1 | ¹H NMR |
|---|---|---|---|
| 9 | 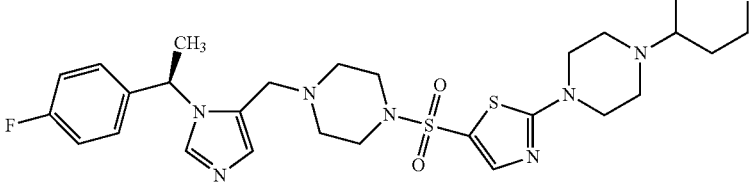 | 617 | (CD3OD δ 7.92 (s, 1H), 7.51 (s, 1H), 7.06-7.10 (m, 2H), 6.88-6.94 (m, 2H), 5.61 (q, J = 6.8 Hz, 1H), 3.58-3.61 (m, 4H), 3.53 (d, J = 14 Hz, 1H), 3.24 (d, J = 14 Hz, 1H), 2.83-2.95 (M, 4H), 2.72-2.74 (m, 6H), 2.34-2.39 (m, 5H). 2.33 (s, 3H), 2.05 (t, J = 14.4 Hz, 2H), 1.63-1.90 (m, 2H). 1.78 (d, J = 7.2 Hz, 3H). 1.54-1.59 (m, 2H) |
| 10 | 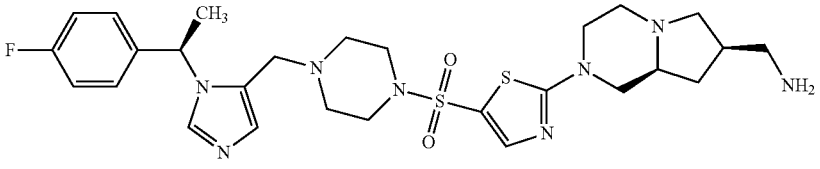 [SMILES: C[C@H](c1ccc(F)cc1)n1cncc1CN1CCN(S(=O)(=O)c2cnc(N3CCN4C[C@@H](CN)C[C@H]4C3)s2)CC1] | 589 | CD3OD δ 7.92 (s, 1H), 7.51 (s, 1H), 7.10~7.06 (m, 2H), 6.92 (t, J = 8.4 Hz, 2H), 6.87 (s, 1H), 5.62 (q, J = 7.2 Hz, 1H), 4.16~4.13 (m, 1H), 3.98~3.94 (m, 1H), 3.55~3.51 (m, 1H), 3.33 (s, 1H), 3.26~2.23 (m, 1H), 3.26~3.23 (m, 1H), 3.12~3.09 (m, 1H), 2.97~2.92 (m, 2H), 2.83 (m, 2H), 2.69~2.63 (m, 4H), 2.41~2.21 (m, 8H), 2.16~2.09 (m, 1H), 1.78 (d, J = 7.2 Hz, 3H), 1.19~1.12 (m, 1H). |
| 11 | 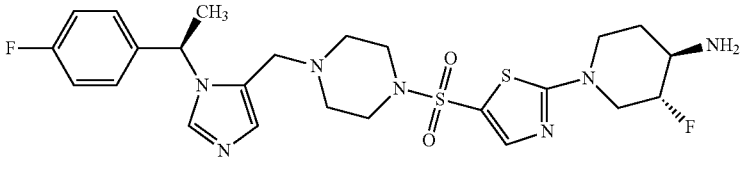 [SMILES: C[C@H](c1ccc(F)cc1)n1cncc1CN1CCN(S(=O)(=O)c2cnc(N3CC[C@@H](N)[C@H](F)C3)s2)CC1] | 552 | (CDCl3) δ 7.68 (s, 1H), 7.53 (s, 1H), 6.96~6.87 (m, 5H), 5.50 (q, J = 7.2 Hz, 1H), 5.07 (br, 1.5H), 4.36~4.21 (m, 2H), 3.87~3.84 (m, 1H), 3.46~3.12 (m, 5H), 2.91 (br, 2H), 2.83 (br, 2H), 2.41~2.35 (m, 4H), 2.10~2.05 (m, 1H), 1.78 (d, J = 7.2 Hz, 3H), 1.61~1.51 (m, 1H). |
| 12 | 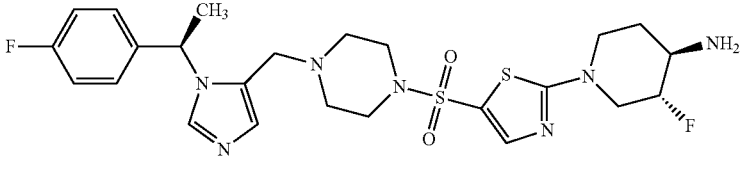 | 552 | (CDCl3) δ 7.68 (s, 1H), 7.54 (s, 1H), 6.97~6.88 (m, 5H), 5.50 (q, J = 7.2 Hz, 1H), 4.76 (br, 1.5H), 4.36~4.22 (m, 2H), 3.89~3.86 (m, 1H), 3.34~3.12 (m, 5H), 2.92 (br, 2H), 2.85 (br, 2H), 2.43~2.36 (m, 4H), 2.10~2.05 (m, 1H), 1.78 (d, J = 7.2 Hz, 3H), 1.62~1.53 (m, 1H). |
| 13 | 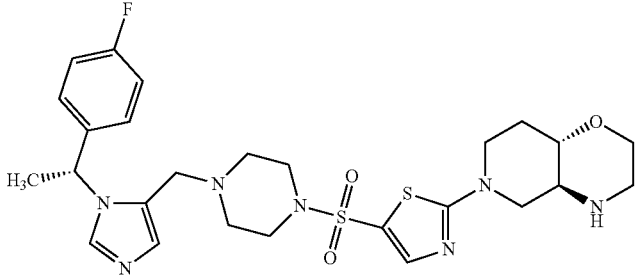 [SMILES: C[C@H](c1ccc(F)cc1)n1cncc1CN1CCN(S(=O)(=O)c2cnc(N3CC[C@@H]4OCCN[C@H]4C3)s2)CC1] | 576 | (CDCl3) δ 7.65 (s, 1H), 7.51 (s, 1H), 6.92~6.88 (m, 5H), 5.48 (q, J = 6.8 Hz, 1H), 4.02~3.99 (m, 2H), 3.90~3.86 (m, 1H), 3.72~3.66 (m, 1H), 3.31~3.17 (m, 4H), 3.07~3.00 (m, 1H), 2.93~2.84 (m, 6H), 2.67~2.61 (s, 1H), 2.40~2.33 (m, 4H), 2.01~1.91 (m, 1H), 1.79~1.72 (m, 4H). |

| No. | Structure | M + 1 | ¹H NMR |
|---|---|---|---|
| 14 | *(structure)* | 576 | (CDCl3) δ 7.68 (s, 1H), 7.52 (s, 1H), 6.96~6.88 (m, 5H), 5.49 (q, J = 6.8 Hz, 1H), 4.07~3.98 (m, 2H), 3.92~3.88 (m, 1H), 3.75~3.69 (m, 1H), 3.34~3.18 (m, 4H), 3.09~3.03 (m, 1H), 2.96~2.84 (m, 6H), 2.71~2.65 (s, 1H), 2.41~2.35 (m, 4H), 1.99 (s, 1H), 1.79~1.67 (m, 4H). |
| 15 | *(structure)* | 576 | (CDCl3) δ 7.68 (s, 1H), 7.54 (s, 1H), 6.97~6.88 (m, 5H), 5.50 (q, J = 6.8 Hz, 1H), 4.12~4.02 (m, 2H), 3.92~3.88 (m, 1H), 3.70~3.64 (m, 1H), 3.33~3.30 (m, 1H), 3.24~3.00 (m, 5H), 2.97~2.85 (m, 5H), 2.67~2.63 (m, 1H), 2.43~2.35 (m, 4H), 1.82 (m, 1H), 1.79 (d, J = 6.8 Hz, 3H), 1.63~1.58 (m, 1H). |
| 16 | *(structure)* | 590 | (DMSO-d6) δ: 7.9 (s, 1H), 7.6 (s, 1H), 7.10~7.07 (m, 2H), 6.96 (t, J = 8.0 Hz, 2H), 6.77 (s, 1H), 5.49 (q, J = 8.0 Hz, 1H), 5.12 (d, J = 2 Hz, 1H), 4.38~4.20 (m, 3H), 4.07~3.97 (m, 1H), 3.87 (d, J = 16.0 Hz, 1H), 3.59 (dd, J-1 = 12.0 Hz, J2 = 4 Hz, 1H), 3.48 (d, J = 14.0 Hz, 1H), 3.25~3.18 (m, 3H), 2.74~2.48 (m, 4H), 2.25~2.24 (m, 4H), 2.05~2.01 (m, 1H), 1.77~1.66 (m, 4H). |
| 17 | *(structure)* | 526 | (CD3OD) δ 7.90 (s, 1H), 7.42 (s, 1H), 7.10-7.06 (m, 2H), 6.93 (t, J = 8.6 Hz, 2H), 6.86 (s, 1H), 5.62 (q, J = 7.0 Hz, 1H), 4.72 (d, J = 47.12 Hz, 1H), 3.75-3.57 (m, 2H), 3.48 (d, J = 13.92 Hz, 1H), 3.24 (d, J = 13.92 Hz, 1H), 2.92-2.72 (m, 6H), 2.41-2.32 (m, 4H), 1.77 (d, J = 7.16 Hz, 3H) |
| 18 | *(structure)* | 590 | (DMSO-d6) δ: 7.98 (s, 1H), 7.88 (s, 1H), 7.06-7.02 (m, 2H), 6.85-6.81 (m, 2H), 6.73 (s, 1H), 5.46 (q, J = 6.8 Hz, 1H), 4.91 (d, J = 4.4 Hz, 1H), 4.22-4.13 (m, 3H), 3.76-3.72 (n, 1H), 3.47 (d, J = 12.8 Hz, 1H), 3.14-3.11 (m, 4H), 3.05-2.98 (m, 1H), 2.73-2.70 (m, 2H), 2.62-2.58 (m, 1H), 2.46-2.22 (m, 5H), 2.17-2.15 (m, 1H), 2.13-1.97 (m, 1H), 1.65 (d, J = 6.8 Hz, 3H). |

-continued

| No. | Structure | M + 1 | ¹H NMR |
|---|---|---|---|
| 19 | 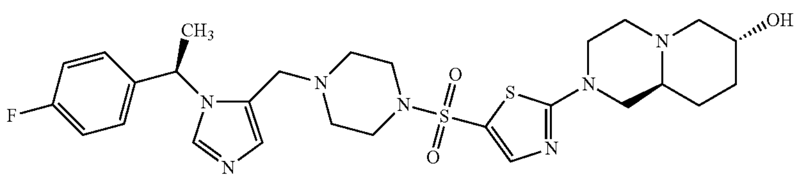 [SMILES: C[C@H](c1ccc(F)cc1)n1cncc1CN1CCN(S(=O)(=O)c2cnc(N3CCN4C[C@H](O)CC[C@H]4C3)s2)CC1] | 590 | (CDCl3) δ 7.67 (s, 1H), 7.49 (s, 1H), 6.91-6.83 (m, 5H), 5.44 (q, J = 7.2 Hz, 1H), 3.82-3.73 (m, 3H), 3.28-3.21 (m, 2H), 3.15 (d, J = 14.0 Hz, 1H), 3.01 (dd, J1 = 10.4 Hz, J2 = 3.2 Hz, 1H), 2.87-2.77 (m, 6H), 2.36-2.30 (m, 5H), 2.05-2.03 (m, 1H), 1.97-1.87 (m, 2H), 1.73 (d, J = 7.2 Hz, 3H), 1.67-1.57 (m, 2H), 1.31-1.19 (m, 2H) |
| 20 | 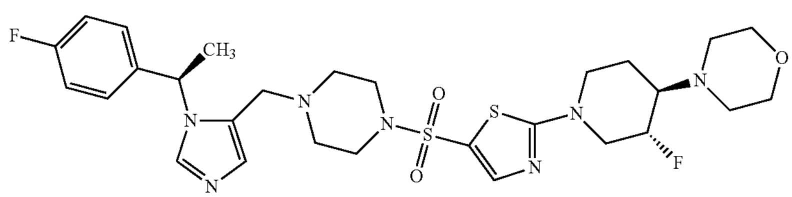 [SMILES: C[C@H](c1ccc(F)cc1)n1cncc1CN1CCN(S(=O)(=O)c2cnc(N3CC[C@@H](N4CCOCC4)[C@H](F)C3)s2)CC1] | 622 | (CD3OD) δ 7.69 (s, 1H), 7.48 (s, 1H), 6.95-6.80 (m, 5H), 5.47 (q, J = 6.8 Hz, 1H), 5.05 (d, J = 48.4 Hz, 1H), 4.38 (t, J = 12.4 Hz, 1H), 4.05 (d, J = 12.8 Hz, 1H), 3.81-3.60 (m, 4H), 3.30-3.09 (m, 4H), 2.99-2.70 (m, 4H), 2.69-2.53 (m, 4H), 2.52-2.21 (m, 5H), 2.11~2.01 (m, 1H), 1.85-1.78 (m, 1H), 1.73 (d, J = 6.8 Hz, 3H) |
| 21 | 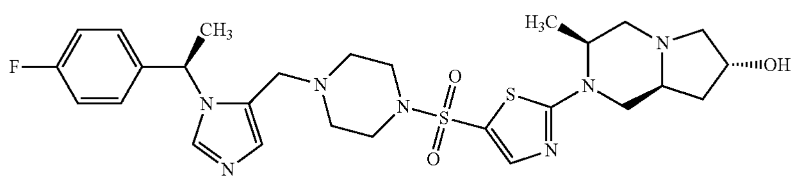 [SMILES: C[C@H](c1ccc(F)cc1)n1cncc1CN1CCN(S(=O)(=O)c2cnc(N3C[C@@H]4C[C@@H](O)CN4C[C@@H]3C)s2)CC1] | 590 | (CDCl3) δ 7.67 (s, 1H), 7.56 (s, 1H), 6.96~6.86 (m, 5H), 5.50 (q, J = 6.8 Hz, 1H), 4.45 (m, 1H), 4.11~4.08 (m, 1H), 3.75~3.65 (m, 2H), 3.47~3.45 (m, 1H), 3.35~3.30 (m, 1H), 3.29~3.23 (m, 1H), 3.04~3.03 (m, 2H), 2.98~2.95 (m, 3H), 2.94~2.88 (m, 3H), 2.42~2.36 (m, 4H), 2.09~2.06 (m, 1H), 1.82 (d, J = 6.8 Hz, 3H), 1.48 (m, 3H). |
| 22 | 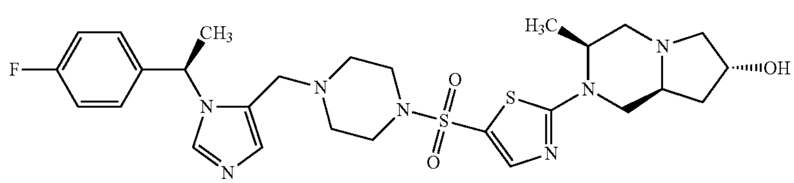 [SMILES: C[C@H](c1ccc(F)cc1)n1cncc1CN1CCN(S(=O)(=O)c2cnc(N3C[C@@H]4C[C@@H](O)CN4C[C@@H]3C)s2)CC1] | 590 | (CDCl3) δ 7.67 (s, 1H), 7.56 (s, 1H), 6.96~6.86 (m, 5H), 5.50 (q, J = 6.8 Hz, 1H), 4.45 (m, 1H), 4.11~4.08 (m, 1H), 3.75~3.65 (m, 2H), 3.47~3.45 (m, 1H), 3.35~3.30 (m, 1H), 3.29~3.23 (m, 1H), 3.04~3.03 (m, 2H), 2.98~2.95 (m, 3H), 2.94~2.88 (m, 3H), 2.42~2.36 (m, 4H), 2.09~2.06 (m, 1H), 1.82 (d, J = 6.8 Hz, 3H), 1.48 (m, 3H). |
| 23 | 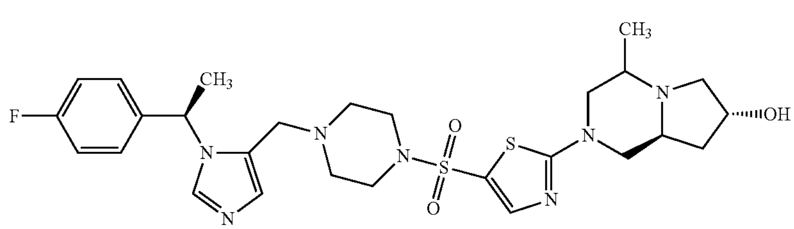 | 590 | (CD3OD) δ: 7.93 (s, 1H), 7.51 (s, 1H), 7.09-7.05 (m, 2H), 6.94-6.87 (m, 3H), 5.61 (q, J = 7.2 Hz, 1H), 4.39-4.35 (m, 1H), 4.13 (d, J = 11.2 Hz, 1H), 3.89 (d, J = 11.2 Hz, 1H), 3.64-6.61 (m, 1H), 3.51 (d, J = 14.0 Hz, 1H), 3.26-3.22 (m, 1H), 2.91-2.81 (m, 4H), 2.71-2.55 (m, 3H), 2.53-2.49 (m, 1H), 2.47-2.29 (m, 4H), 2.01-2.11 (m, 1H), 1.71-1.88 (m, 5H), 1.14 (d, J = 6.8 Hz, 3H) |

-continued

| No. | Structure | M + 1 | ¹H NMR |
|---|---|---|---|
| 24 | 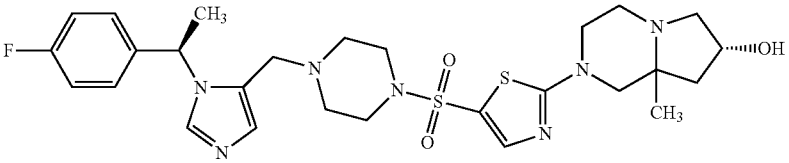 [SMILES: C[C@H](c1ccc(F)cc1)n1cncc1CN1CCN(S(=O)(=O)c2cnc(N3CCN4C[C@H](O)CC4(C)C3)s2)CC1] | 590 | (CDCl3) δ 7.61 (s, 1H), 7.48 (s, 1H), 6.89~6.85 (m, 5H), 5.43 (q, J = 6.8 Hz, 1H), 4.73 (m, 2H), 4.44~4.34 (m, 1H), 3.61~3.54 (m, 1H), 3.35~3.31 (m, 3H), 3.23~3.21 (m, 2H), 3.07~3.01 (m, 1H), 2.91~2.82 (m, 6H), 2.32~2.31 (m, 4H), 2.01~1.98 (m, 2H), 1.95 (d, J = 6.8 Hz, 3H), 1.71 (s, 3H). |
| 25 | 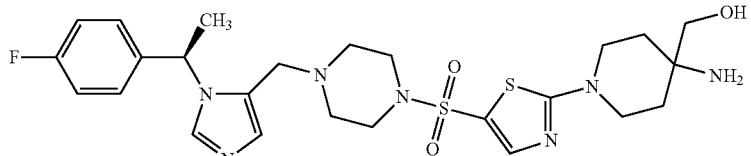 | | (CD3OD) δ 7.93 (s, 1H), 7.52 (s, 1H), 7.12-7.03 (m, 2H), 6.94 (t, J = 8.8, 2H), 6.88 (s, 1H), 5.62 (q, J = 7.2, 1H), 3.98-3.64 (m, 4H), 3.65 (s, 2H), 3.25 (d, J = 14.0, 2H), 2.92-2.62 (m, 4H), 2.48-2.26 (m, 4H), 1.92-1.82 (m, 2H), 1.82 (d, J = 6.8 Hz, 3H), 1.68-1.60 (m, 2H) |
| 26 | 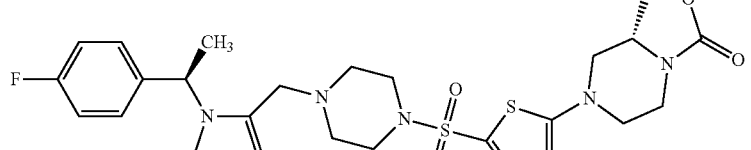 | 576 | (CD3OD) δ: 7.92 (s, 1H), 7.53 (s, 1H), 7.09-7.05 (m, 2H), 6.95-6.86 (m, 3H) 5.61-5.57 (q, J = 7.2Hz, 1H), 4.52-4.48 (t, J = 8.8, 1H), 4.34 (d, J = 8.8 Hz, 1H), 4.12-4.05 (m, 3H), 3.85-3.82 (m, 1H), 3.51 (d, J = 14 Hz, 1H), 3.23-3.11 (m, 4H), 2.83 (bs, 2H), 2.69 (bs, 2H), 2.39 (bs, 2H), 2.32 (bs, 2H), 1.77 (d, J = 6.8 Hz, 3H) |
| 27 | 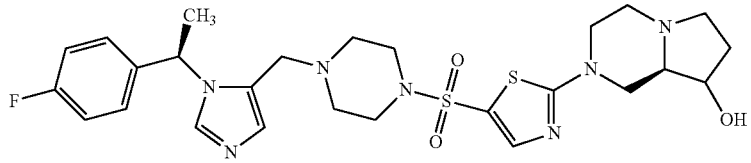 [SMILES: C[C@H](c1ccc(F)cc1)n1cncc1CN1CCN(S(=O)(=O)c2cnc(N3CCN4CCC(O)[C@H]4C3)s2)CC1] | 576 | (CD3OD) δ 7.93 (s, 1H), 7.52 (s, 1H), 7.09~7.05 (m, 2H), 6.94~6.90 (m, 2H), 6.89~6.87 (m, 1H), 5.60 (q, J = 6.8 Hz, 1H), 4.24~4.23 (m, 1H), 3.97~3.93 (m, 2H), 3.54~3.51 (m, 1H), 3.26~3.21 (m, 2H), 3.06~3.01 (m, 3H), 2.86~2.83 (m, 2H), 2.46~2.23 (m, 7H), 2.07~2.06 (m, 1H), 1.79 (d, J = 6.8 Hz, 3H), 1.62~1.60 (m, 1H) |

Example 2

Preparation of Compound 28

Step A Preparation of Int 2-1

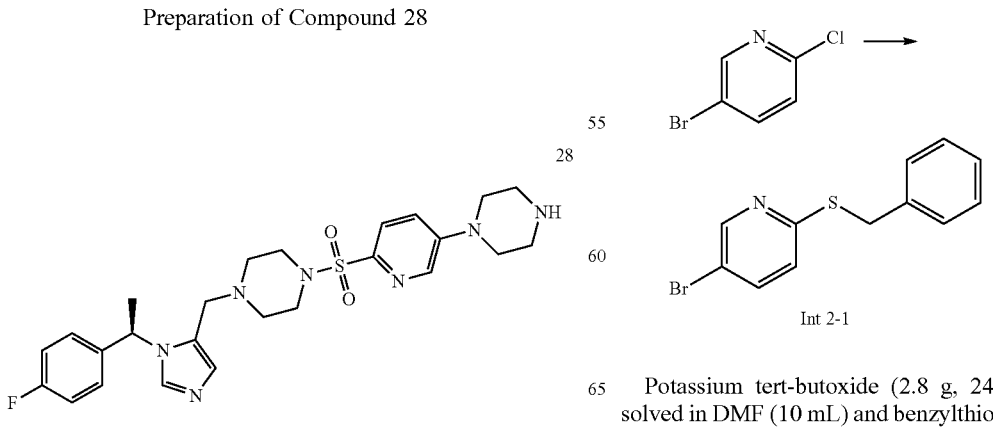

Potassium tert-butoxide (2.8 g, 24.84 mmol) was dissolved in DMF (10 mL) and benzylthiol (2.6 g, 20.70 mmol) was added dropwise at 0° C. The mixture was allowed to stir at room temperature for 15 minutes and then cooled to 0° C., a solution of 5-bromo-2-chloropyridine (4.0 g, 20.70 mmol) in DMF (4 mL) was added dropwise at 0° C. and the mixture was heated at 80° C. for 1.5 hours. The mixture was poured into water (100 mL) and extracted with ethyl estate (3×100 mL). The combined organic phases were washed with brine (100 mL), water (100 mL) and dried (Na$_2$SO$_4$). Concentrated in vacuo to provide the residue, which was purified with column chromatography (petroleum ether:EtOAc=10:1) to provide Int 2-1 (4.0 g, 69%). MS (ESI): m/z (M+H)$^+$ 280.

Step B Preparation of Int 2-2

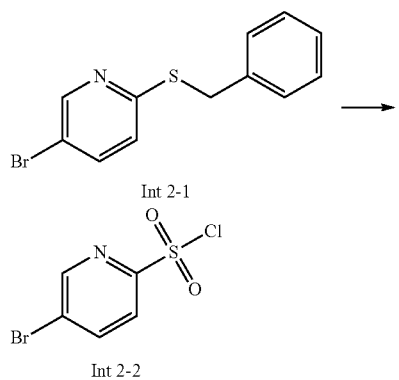

To a solution of Int 2-1 (1.5 g, 5.40 mmol) in DCM (100 mL) was added water (100 mL) and HCOOH (100 mL). The heterogeneous mixture was cooled to 0° C. and Cl$_2$ gas was bubbled for 30 minutes until the mixture turned to deep yellow. The organic phase was separated, extracted with DCM (3×100 mL) and the combined organic phase was washed with 1M NaOH (100 mL) followed by brine (100 mL), concentration to provide a residue (1.1 g) of Int 2-2 which was used for the next step without purification.

Step C Preparation of Int 2-3

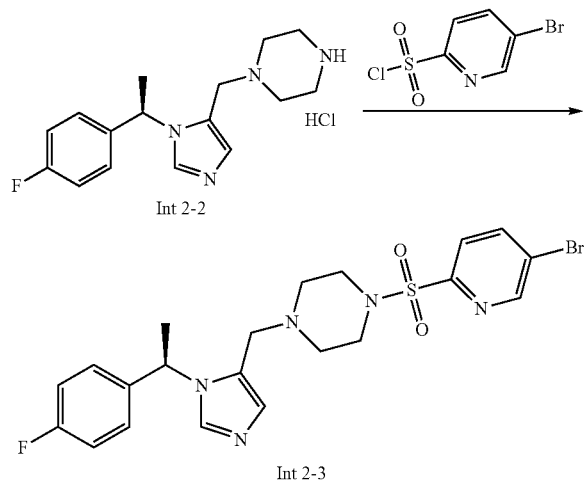

To the suspension of Int 1-7 (474 mg, 1.85 mmol) in DCM (15 mL) was added Et$_3$N (476 mg, 4.62 mmol) and compound Int 2-2 (500 mg, 1.54 mmol) at 0° C. The mixture was allowed to stir at 0° C. for 1 hour. The mixture was poured into water (20 mL) and extracted with DCM (3×15 mL). The combined organic phases were washed with brine (20 mL), water (20 mL) and dried (Na$_2$SO$_4$). Concentrated in vacuo to provide the residue, which was purified with column chromatography (CH$_2$Cl$_2$:MeOH=20:1) to provide Int 2-3 (350 mg, 45%). MS (ESI): m/z (M+H)$^+$ 508.

Step C Preparation of Compound 28

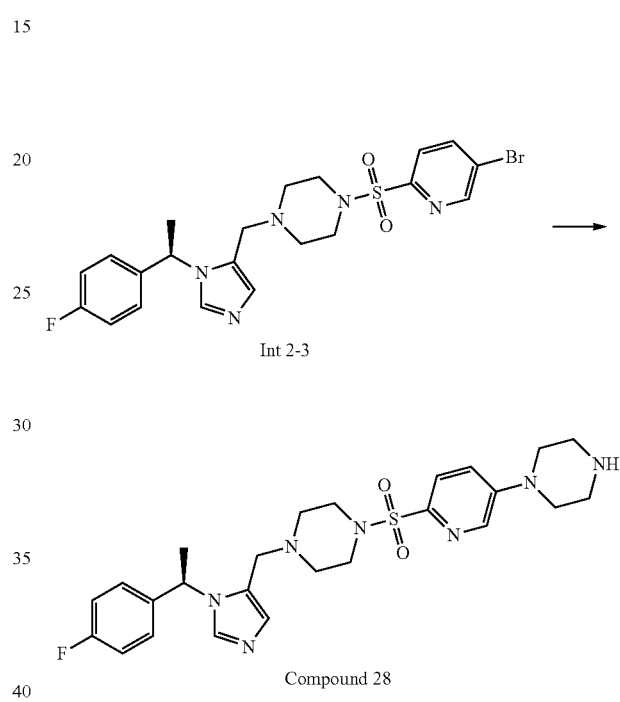

A mixture of compound Int 2-3 (80 mg, 0.16 mmol), Boc piperazine (32 mg, 0.24 mmol), Pd$_2$(dba)$_3$ (15 mg, 0.016 mmol), X-phos (11 mg, 0.032 mmol) and Cs$_2$CO$_3$ (104 mg, 0.32 mmol) in DMF (3 mL) was heated to 80° C. for about 15 hours under nitrogen. The mixture was filtered and the filtrate was concentrated in vacuo, the resulting residue was purified using HPLC to provide (100 mg, 0.16 mmol) of the Boc piperazine adduct which was dissolved in HCl/EtOAc (15 mL) and stirred at room temperature for 1 hour before the solvent was concentrated in vacuo. The resulting residue was purified using HPLC to provide compound 28 (59 mg, 70%). $^1$H NMR (CD$_3$OD): δ 8.36 (d, J=2.8 Hz, 1H), 7.91 (s, 1H), 7.70 (d, J=8.8 Hz, 1H), 7.43-7.46 (m, 1H), 7.02-7.06 (m, 2H), 6.85-6.89 (m, 3H), 5.57-5.62 (m, 1H), 3.47-3.50 (m, 5H), 3.21-3.25 (m, 1H), 3.09 (s, 4H), 2.94-2.96 (m, 2H), 2.79-2.81 (m, 2H), 2.28-2.36 (m, 4H), 1.76 (d, J=7.2 Hz, 3H). MS (ESI): m/z (M+H)$^+$ 514.

The following compounds were prepared as described in Example 2 using from Int 2-2 and the appropriately substituted sulfonylchloride.

| Cmpd | Structure | M + 1 | ¹H NMR |
|---|---|---|---|
| 29 | 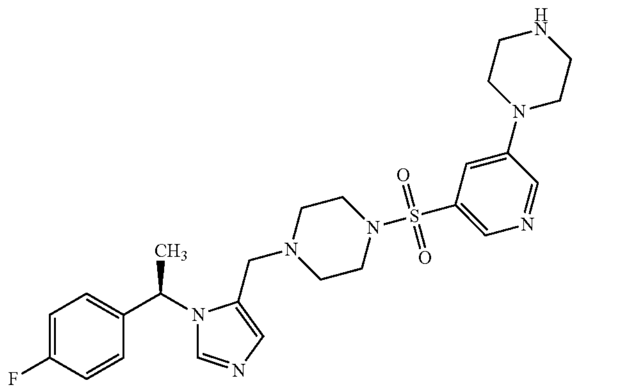 [SMILES: C[C@H](c1ccc(F)cc1)n1cncc1CN1CCN(S(=O)(=O)c2cncc(N3CCNCC3)c2)CC1] | 514 | (CD3OD) δ 8.50 (s, 1H), 8.17 (s, 1H), 7.87 (s, 1H), 7.44 (s, 1H), 6.99-7.03 (m, 2H), 6.82 (t, J = 8.0 Hz, 3H), 5.52-5.58 (m, 1H), 3.43-3.47 (m, 1H), 3.29-3.31 (m, 4H), 3.19-3.22 (m, 1H), 2.98 (t, J = 5.0 Hz, 4H), 2.70-2.82 (m, 4H), 2.30-2.73 (m, 4H), 1.72 (d, J = 7.2 Hz, 3H). |
| 30 | 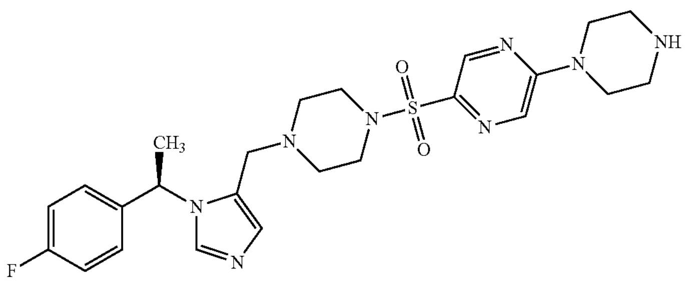 [SMILES: C[C@H](c1ccc(F)cc1)n1cncc1CN1CCN(S(=O)(=O)c2cnc(N3CCNCC3)cn2)CC1] | 515 | (CDCl3): δ 8.52 (s, 1H), 8.01 (s, 1H), 7.66 (s, 1H), 6.87~6.96 (m, 5H), 5.46~5.51 (m, 1H), 3.73~7.75 (t, 4H), 3.33 (d, J = 14.0 Hz, 1H) 3.20 (d, J = 14.0 Hz, 1H), 2.99~3.06 (m, 8H), 2.33~2.39 (m, 4H), 1.77 (d, J = 4.8 Hz, 3H). |

Example 3

Preparation of Compound 31

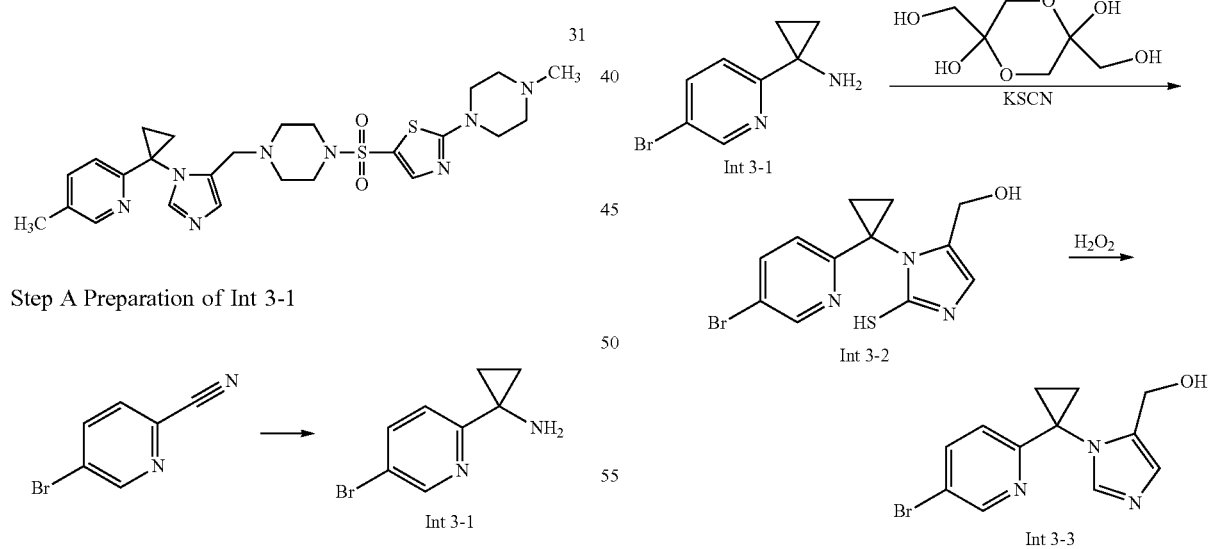

Step A Preparation of Int 3-1

To a stirred solution of 5-bromo-2-cyanopyridine (30.0 g, 0.165 mol) and Ti(O-iPr)₄ (51.5 g, 0.181 mol) in 900 mL THF was added EtMgBr (330 mL, 0.045 mmol) under nitrogen at 0° C. The reaction mixture was allowed to stir at room temperature for 5 hours. The reaction was quenched by water and extracted by EtOAc, filtrated and the organic layers were dried over Na₂SO₄, filtrated and concentrated in vacuo. The resulting residue was purified using flash column chromatography on silica gel eluted with petroleum ether: EtAOc=30:1 to provide product (7.2 g, 21%). MS-ESI (m/z): 213, 215 (M+H)⁺

Step B Preparation of Int 3-3

To a solution of compound Int 3-1 (7.1 g, 0.033 mol) in the 80 mL of mixed solvent (MeCN/H₂O=1:1) was added 2,5-bis(hydroxymethyl)-1,4-dioxane-2,5-diol (7.81 g, 0.043 mol), KSCN (4.18 g, 0.043 mol) and acetic acid (4 mL). The mixture was allowed to stir at 90° C. for 6 hrs. then cooled to 0° C. and treated dropwise with H₂O₂ (2.7 g). The ice bath was removed and the mixture was allowed to stir at room temperature for 1 hr. The mixture was quenched by adding NaHSO$_3$ and basified by adding ammonium hydroxide until pH>8. The mixture was extracted with EtOAc and the organic layer was washed with brine, dried over Na$_2$SO$_4$ and concentrated in vacuo. The resulting residue of compound Int 3-3 was used without purification (9.67 g, 100%) MS-ESI (m/z): 294, 296 (M+H)$^+$.

Step C Preparation of Int 3-4

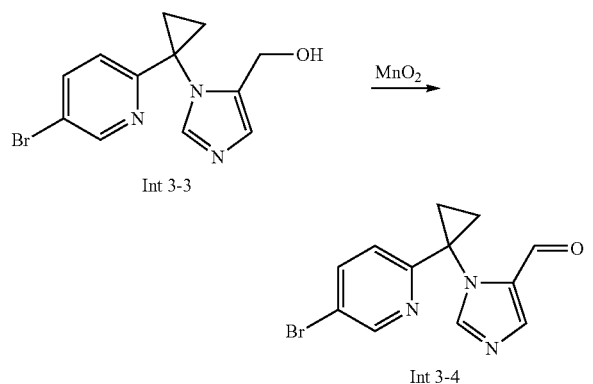

To a solution of compound Int 3-3 (9.67 g, 0.033 mol) in dioxane (100 mL) was added MnO$_2$ (14.2 g, 0.165 mol) in one portion. The mixture was refluxed for about 15 hours, cooled and the mixture was filtered through Celite and concentrated in vacuo. The resulting residue was purified using flash column chromatography on silica gel eluting with dichloromethane:methanol=50:1 to provide compound Int 3-4 (0.45 g, Yield: 12%) as brown oil. MS-ESI (m/z): 292, 294 (M+H)$^+$.

Step D Preparation of Int 3-5

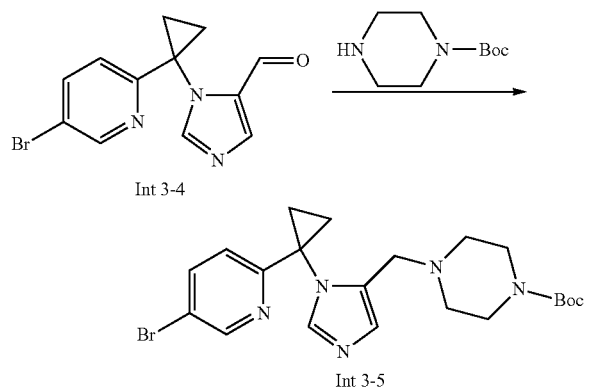

To a solution of compound Int 3-4 (0.5 g, 1.72 mmol) in 1,2-dichloroethane (15 mL) was added N-Boc-piperazine (320 mg, 1.72 mmol). The reaction mixture was allowed to stir at room temperature for 1 hour and followed by the addition of NaBH(OAc)$_3$ (1.1 g, 5.15 mmol). Then the mixture was allowed to stir at room temperature for about 15 hours. The reaction mixture was quenched with ice cooled water and extracted with dichloromethane (3×30 mL). The combined organic extracts were washed with brine, dried over Na$_2$SO$_4$ and concentrated in vacuo to provide crude desired product as yellow oil. The resulting residue of compound Int 3-5 (0.74 g, 97%) was used without purification. MS-ESI (m/z): 462, 464 (M+H)$^+$.

Step E Preparation of Int 3-6

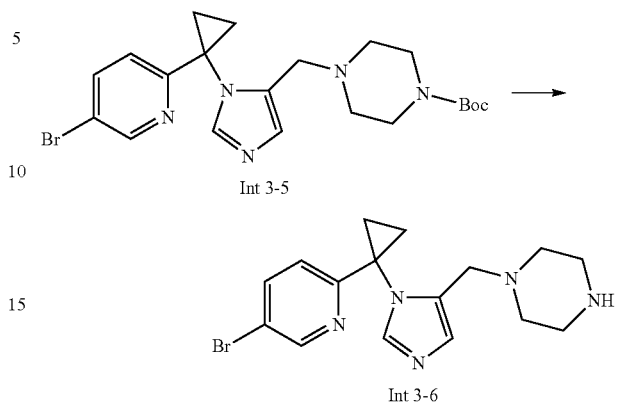

A mixture of compound Int 3-5 (774 mg, 1.68 mmol) in HCl/EtOAc (20 mL) was allowed to stir at room temperature for 1 hours, then concentrated in vacuo and used in the next step without further purification. MS-ESI (m/z): 362, 364 (M+H)$^+$ Step F Preparation of Int 3-7

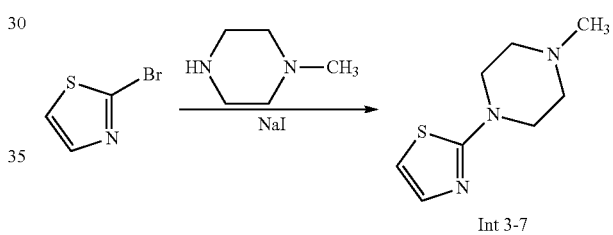

A solution of 2-bromothiazole (36.46 g, 0.22 mol) in N-methylpiperazine (109.75 g, 1.10 mol) was added NaI (0.33 g, 2.2 mmol) with stirring under N$_2$. The reaction mixture was allowed to stir at 120° C. for 16 hrs. The reaction mixture was cooled to 25° C. and diluted with 1000 mL of EtOAc. The mixture was washed with a solution of 5% citric acid (100 mL×3) and saturated solution of Na$_2$CO$_3$ (100 mL×2). The organic layer was dried over Na$_2$SO$_4$, filtered and concentrated in vacuo to provide compound Int 3-7 as red oil (25.7 g, 64%). $^1$H NMR (CDCl$_3$) δ: 7.14 (d, J=3.6 Hz, 1H), 6.52 (d, J=3.6 Hz, 1H), 3.46 (t, J=5.2 Hz, 4H), 2.47 (t, J=5.2 Hz, 4H), 2.31 (s, 3H). MS-ESI (m/z): 184 (M+1)$^+$ R$_f$:0.2 (petroleum ether:EtOAc=1:2)

Step G Preparation of Int 3-8

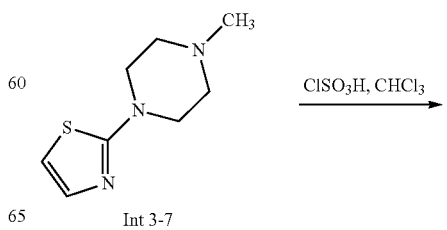

-continued

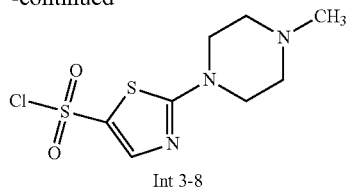

Int 3-8

A solution of Int 3-7 (10 g, 54 mmol) in CHCl$_3$ (100 mL) was treated drop wise with 20 mL of HSO$_3$Cl with stirring at 0° C. The reaction mixture was allowed to stir at 100° C. for 2 hrs, cooled and concentrated in vacuo to remove the CHCl$_3$. 20 mL of SOCl$_2$ was added and the reaction mixture was allowed to stir at 100° C. for another 16 hrs. Then the reaction mixture was cooled and concentrated in vacuo to remove the excess SOCl$_2$. The resulting residue was carefully poured onto water-ice and filtered. The filter cake was dried under vacuum to provide compound Int 3-8 as yellow solid (6.75 g, 44%). $^1$H NMR (CDCl$_3$) δ: 7.94 (s, 1H), 4.23 (d, J=14.8 Hz, 2H), 3.65~3.54 (m, 5H), 3.22~3.16 (m, 1H), 2.89 (s, 3H). MS-ESI (m/z): 282 (M+1)$^+$ Step H Preparation of Int 3-9

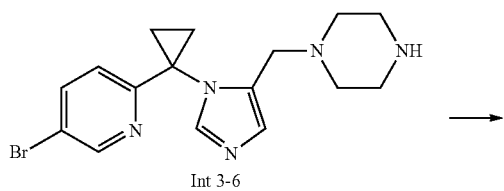

Int 3-6

-continued

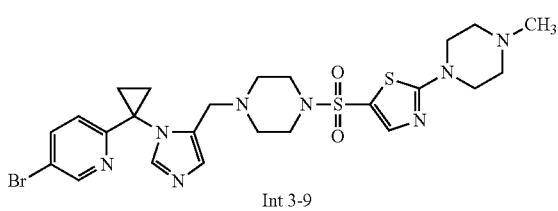

Int 3-9

To a stirred solution of compound Int 3-6 (610 mg HCl salt, 1.415 mmol) in DCM (10 mL) was added Et$_3$N (0.3 mL). The mixture was allowed to stir at room temperature for 0.5 hours before 437 mg (1.4 mmol) of Int 3-8 was added in portions at 0° C. The mixture was allowed to stir at room temperature for 2 hours, the reaction mixture was filtered, and the filtrate was added to water (30 mL) and EtOAc (60 mL). The separated organic layer was washed with water (3×20 mL) again. The combined organic layer was dried with MgSO$_4$, concentrated in vacuo to provide resulting residue. The resulting residue was purified using pre-TLC to provide 350 mg of compound Int 3-7 as a brown solid. MS-ESI (m/z): 607, 609 (M+H)$^+$ Step I Preparation of Compound 31

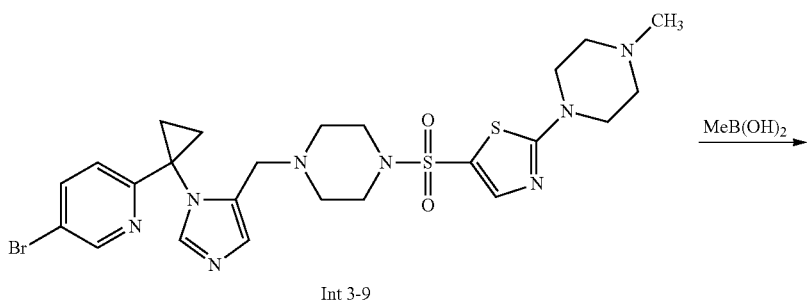

Int 3-9

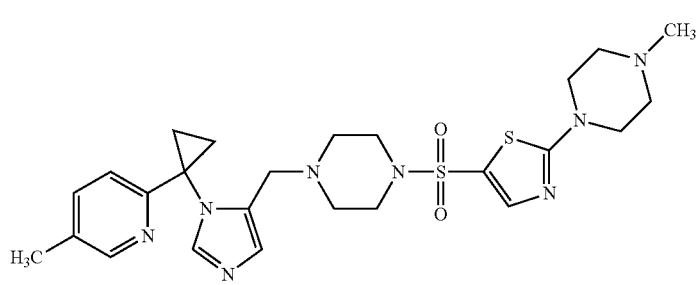

Compound 31

To a stirred solution of compound Int 3-7 (200 mg, 0.33 mmol) and MeB(OH)$_2$ (50 mg, 0.066 mmol) in 8 mL dioxane was added Pd(OAc)$_2$ (10 mg, 0.045 mmol), PCy$_3$ (25 mg, 0.09 mmol) and K$_3$PO$_4$ (210 mg, 0.99 mmol). The mixture was degassed with nitrogen and stirred at 120° C. for about 15 hours. The reaction was concentrated in vacuo and the resulting residue was purified using preparatory HPLC to provide 30 mg of Compound 31 as a white solid. $^1$H NMR (CD3OD) δ 8.12 (s, 1H), 7.85 (s, 1H), 7.46 (s, 1H), 7.34~7.32 (d, J=8.0 Hz, 1H), 6.93 (s, 1H), 6.27~6.25 (d, J=8.0 Hz, 1H), 3.62~3.59 (m, 4H), 3.43 (s, 2H), 2.63~2.56 (m, 8H), 2.59~2.57 (m, 7H), 2.17 (s, 3H), 1.75 (m, 2H), 1.65 (m, 2H). MS-ESI-ESI (m/z): 543 (M+H)$^+$ The following compounds were prepared as described in Example 3 above using the appropriately substituted amine as Int 3-1.

Example 4

Preparation of Compound 35

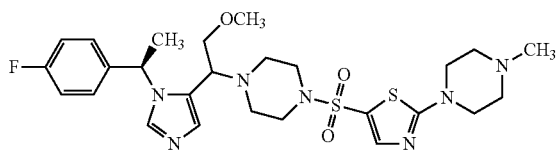

| No. | Structure | MS (M + 1) | $^1$H NMR |
|---|---|---|---|
| 32 | 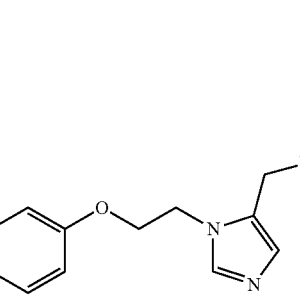 | 566 | (CD3OD) δ 7.71 (s, 1H), 7.56 (s, 1H), 7.19 (t, J = 8.8, 2H), 6.85 (s, 1H), 6.79 (t, J = 9.2, 2H), 4.42 (t, J = 10.0, 2H), 4.24 (t, J = 10.0, 2H), 3.62-3.58 (m, 6H), 3.02 (br, 4H), 2.58-2.48 (m, 8H), 2.33 (s, 3H). |
| 33 | 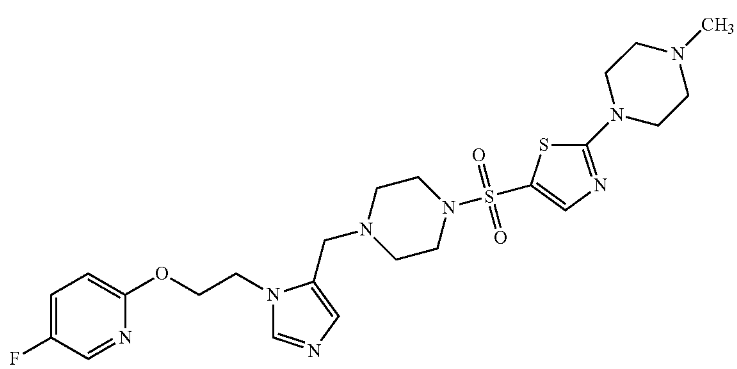 [SMILES: CN1CCN(c2ncc(S(=O)(=O)N3CCN(Cc4cncn4CCOc4ccc(F)cn4)CC3)s2)CC1] | 551 | (CDCl3) δ 7.87 (s, 1H), 7.56 (s, 1H), 7.52 (s, 1H), 7.36-7.30 (m, 1H), 6.88 (s, 1H), 6.67 (dd, J1 = 9.2, J2 = 3.6, 1H), 4.49 (t, J = 10.4, 2H), 4.32 (t, J = 10.8, 2H), 3.55 (t, J = 10.0, 4H), 3.50 (s, 2H), 3.08 (br, 4H), 2.54-2.48, (m, 8H) 2.33 (s, 3H). |
| 34 | 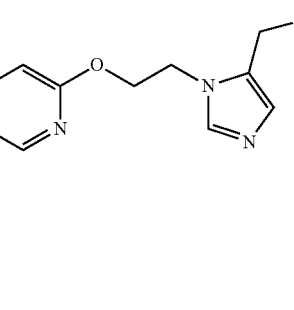 | 581 | (CD3OD) δ 7.60 (d, J = 8.0 Hz, 1H), 7.54 (s, 1H), 7.49 (t, J = 8 Hz, 2H), 7.31 (s, 1H), 6.93 (s, 1H), 5.98 (t, J = 7.6 Hz, 1H), 3.64-3.52 (m, 6H), 3.29-3.18 (m, 1H), 3.09-3.00 (m, 5H), 2.82-2.57 (m, 1H), 2.57-2.52 (m, 8H), 2.35 (s, 3H), 2.31-2.26 (m, 1H). |

Step A Preparation of Int 4-1

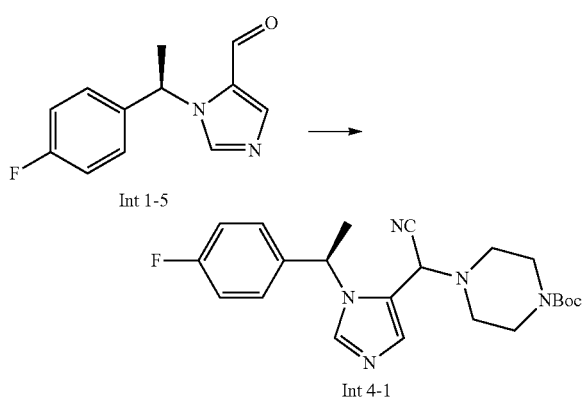

To a solution of Int 1-5 from Example 1, Step D above (2.0 g, 9.17 mmol) in Et$_2$O (50 mL) was added TMSCN (1.12 g, 10.09 mmol) and ZnI$_2$ (0.86 g, 2.76 mmol). The mixture was allowed to stir at 0° C. for 10 minutes, piperazine-1-carboxylic acid tert-butyl ester (1.9 g, 10.09 mmol) in MeOH (50 mL) was added at 0° C. Then Et$_3$N (1.4 g, 13.73 mmol) was added and the mixture was heated at 60° C. for 24 hours. The mixture was poured into H$_2$O (20 mL) and extracted with EtOAc (20 mL×3), the combined organic layer was washed with brine (20 mL), dried over sodium sulfate and concentrated in vacuo. The crude mixture was and purified with column chromatography (PE:EtOAc=3:1) to provide Int 4-1 (3.0 g, 79%). MS (ESI): m/z (M+H)$^+$ 414.

Step B Preparation of Int 4-2

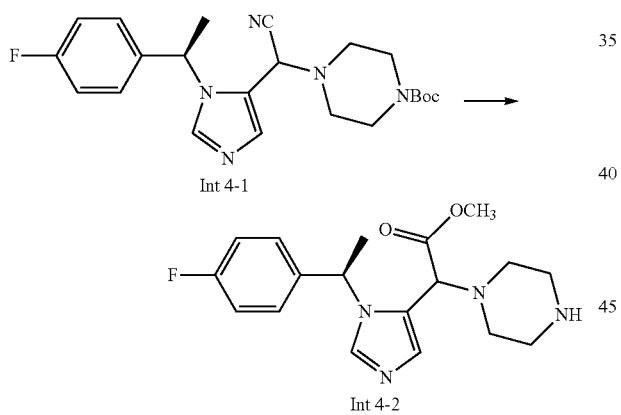

The solution of Int 4-1 (3.0 g, 7.26 mmol) in HCl/MeOH (100 mL) was allowed to stir at 70° C. for about 15 hours. The reaction mixture was cooled and concentrated in vacuo to provide crude Int 4-2 (2.5 g) as the HCl salt. MS (ESI): m/z (M+H)$^+$ 347.

Step C Preparation of Int 4-3

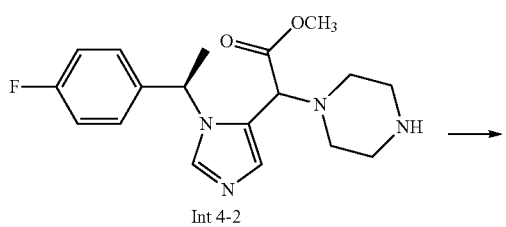

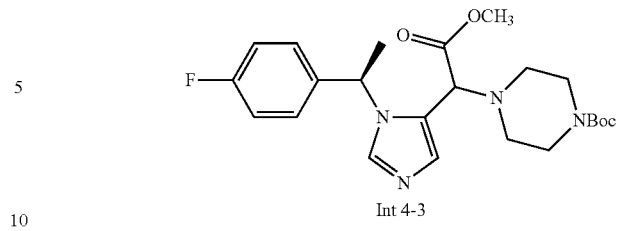

To a solution of Int 4-2 (2.5 g, 7.26 mmol) in DCM (50 mL) and H$_2$O (30 mL) was added NaOH (1.5 g, 36.30 mmol) at 0° C., then (Boc)$_2$O (2.4 g, 10.89 mmol) was added at 0° C. The reaction mixture was allowed to warm to room temperature and stirred for 5 hours. The reaction mixture was poured into H$_2$O (20 mL), extracted with DCM (20 mL×3), the combined organic layer was washed with brine (20 mL), dried over sodium sulfate and concentrated in vacuo. The crude mixture was and purified with column chromatography (petroleum ether/EtOAc=3:1) to provide Int 4-3 (2.5 g, 78%). MS (ESI): m/z (M+H)$^+$ 447.

Step D Preparation of Int 4-4

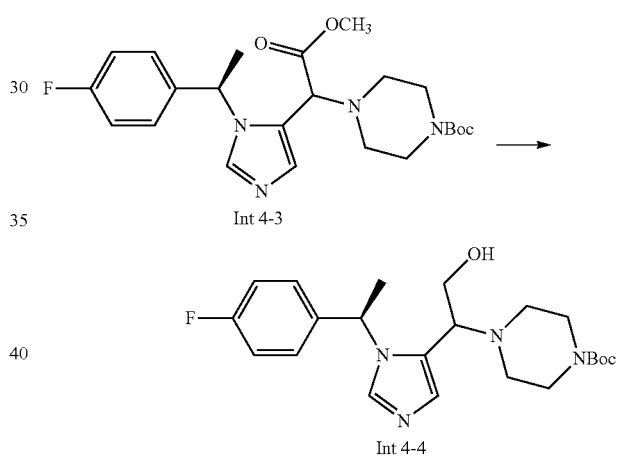

To a solution of Int 4-3 (1.0 g, 2.24 mmol) in THF (20 mL) was added LiAlH$_4$ (255 mg, 6.73 mmol) at 0° C. and the whole mixture was allowed to stir at 0° C. for 4 hours. The mixture was poured into H$_2$O (20 mL) and extracted with EtOAc (20 mL×3), the combined organic layer was washed with brine (20 mL), dried over sodium sulfate and concentrated in vacuo to provide Int 4-4 (650 mg, 69%). MS (ESI): m/z (M+H)$^+$ 419.

Step E Preparation of Int 4-5

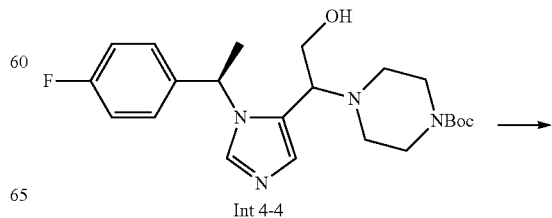

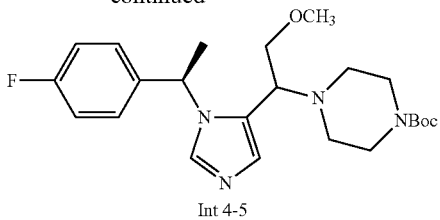

Int 4-5

To a solution of Int 4-4 (200 mg, 0.48 mmol) in THF (10 mL) was added NaH (58 mg, 1.44 mmol) at 0° C. The mixture was allowed to stir at 0° C. for 10 minutes before MeI (68 mg, 0.48 mmol) was added and the mixture was allowed to warm to room temperature and stirred for about 15 hours. The mixture was poured into H$_2$O (10 mL) and extracted with EtOAc (10 mL×3), the combined organic layer was washed with brine (10 mL), dried over sodium sulfate and concentrated in vacuo to provide Int 4-5 (200 mg, 97%) MS (ESI): m/z (M+H)$^+$ 433.

Step F Preparation of Int 4-6

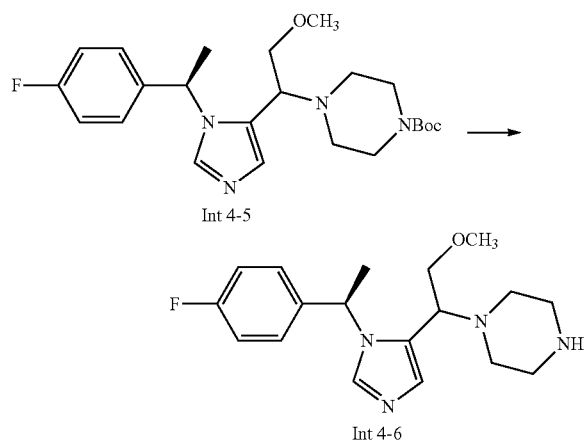

Int 4-5

Int 4-6

The solution of Int 4-5 (200 mg, 0.46 mmol) in HCl/EtOAc (10 mL) was allowed to stir at 0° C. for 1 hour. The reaction mixture was concentrated in vacuo to provide crude Int 4-6 (150 mg) which was used into the next step without further purification. MS (ESI): m/z (M+H)$^+$ 333.

Step G Preparation of Compound 35

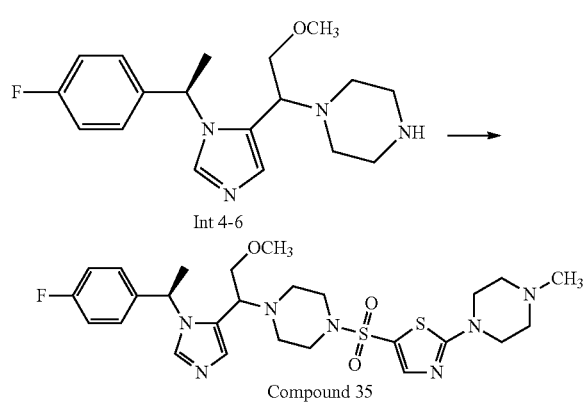

Int 4-6

Compound 35

To a solution of Int 4-6 (150 mg, 0.45 mmol) in DMF (10 mL) was added Et$_3$N (227 mg, 2.25 mmol) at 0° C. for 10 minutes then 4-(4-methyl-piperazin-1-yl)-thiazole-2-sulfonyl chloride (252 mg, 0.90 mmol) was added, the mixture was allowed to stir at 0° C. for 30 minutes, filtered and the filtrate was purified using preparative HPLC to provide Compound 35

Diastereomer A: (8 mg, 3%). $^1$H NMR (CD$_3$OD): δ 7.80 (s, 1H), 7.45 (s, 1H), 7.03-7.07 (m, 2H), 6.85-6.91 (m, 3H), 5.56 (q, J=7.2 Hz, 1H), 4.04 (t, J=6.0 Hz, 1H), 3.87-3.91 (m, 1H), 3.70-3.74 (m, 1H), 3.60 (s, 4H), 3.34 (s, 3H), 2.49-2.68 (m, 10H), 2.47-2.48 (m, 2H), 2.34 (s, 3H), 1.76 (d, J=6.8 Hz, 3H). MS (ESI): m/z (M+H)$^+$ 578.

Diastereomer B: (25 mg, 10%). $^1$H NMR (CD$_3$OD): δ 7.97 (s, 1H), 7.55 (s, 1H), 6.99-7.01 (m, 4H), 6.93 (s, 1H), 5.77 (q, J=7.2 Hz, 1H), 3.52-3.73 (m, 7H), 3.30 (s, 1H), 2.95 (s, 4H), 2.72-2.75 (m, 2H), 2.56-2.60 (m, 6H), 2.36 (s, 3H), 1.79 (d, J=7.2 Hz, 3H). MS (ESI): m/z (M+H)$^+$ 578.

Example 5

Preparation of Compound 36

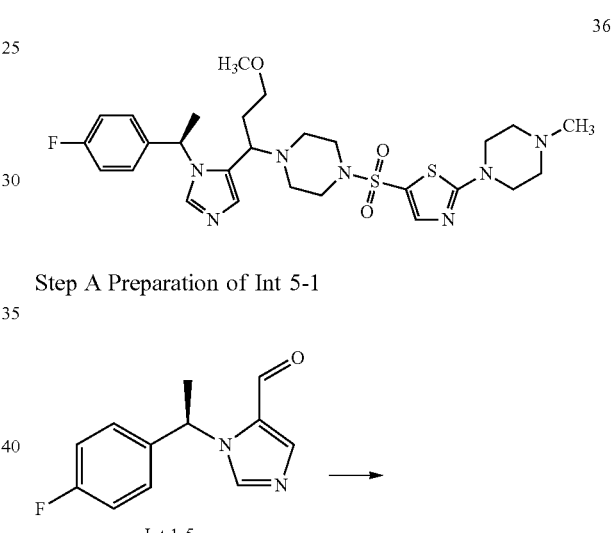

36

Step A Preparation of Int 5-1

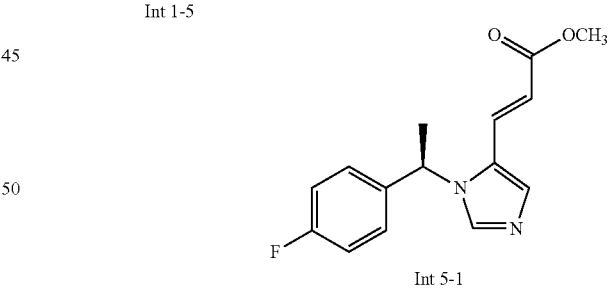

Int 1-5

Int 5-1

To a solution of methyl 2-(hydroxy(methoxy)phosphoryl) acetate (3.34 g, 18.3 mmol) in THF (40 mL) was added NaH (1.1 g, 27.5 mmol) at 0° C. After stirring at 0° C. for 1 hour, a solution of Int 1-5 (4 g, 18.3 mmol) in THF (4 mL) was added dropwise. The mixture was allowed to stir at room temperature for about 15 hours. The reaction mixture was quenched with aqueous NH$_4$Cl (10 mL) then extracted with EtOAc (30 mL×4). The combined organic layer was dried over Na$_2$SO$_4$ and concentrated in vacuo. The resulting residue was purified using column chromatography (petroleum ether/EtOAc=5:1) to provide Int 5-1 (4 g, 80%). $^1$H NMR (400 MHz, CD$_3$OD): δ 8.03 (s, 1H), 7.55 (s, 1H), 7.40-7.45 (m, 1H), 7.16-7.19 (m, 2H), 7.04-7.08 (m, 2H), 6.25-6.31 (m, 1H), 5.63-5.69 (m, 1H), 3.69 (s, 3H). MS (ESI): m/z (M+H)+ 275.

Step B Preparation of Int 5-2

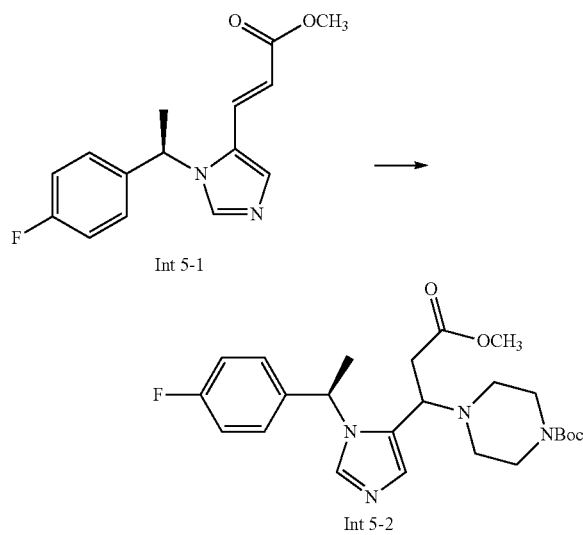

To a mixture of compound Int 5-1 (1 g, 3.65 mmol) and piperazine-1-carboxylic acid tert-butyl ester (6.7 g, 36.5 mmol) was added ZrCl$_4$ (500 mg) and the mixture was allowed to stir at 130° C. for 8 hours. The mixture was filtered and the filtrated was concentrated in vacuo. The resulting residue was purified using preparative HPLC to provide Int 5-2 (0.5 g, 30%). $^1$H NMR (CD$_3$OD): δ 9.11 (s, 1H), 7.64 (s, 1H), 7.33-7.36 (m, 2H), 7.16-7.19 (m, 2H), 5.99-6.05 (m, 1H), 4.53-4.56 (m, 1H), 3.64 (s, 3H), 2.99-3.10 (m, 6H), 2.35-2.38 (m, 4H), 1.93 (d, J=7.2 Hz, 3H), 1.40 (s, 9H). MS (ESI): m/z (M+H)+ 331.

Step C Preparation of Int 5-3

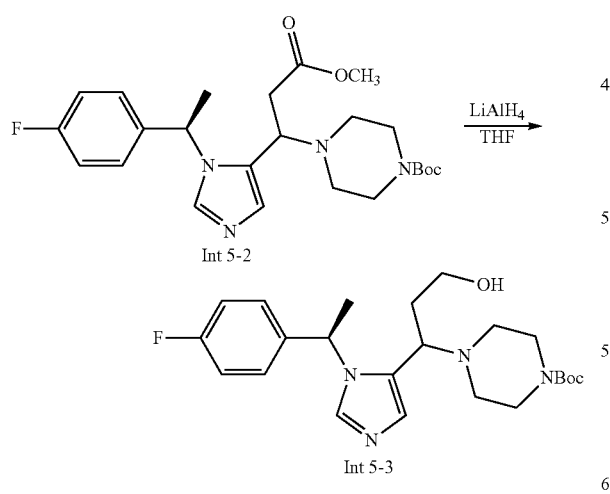

To a solution of compound Int 5-2 (300 mg, 0.652 mmol) in THF (30 mL) was added LiAlH$_4$ (49 mg, 1.3 mmol) at 0° C., and the reaction mixture was allowed to stir at room temperature for 2 hours before water (0.3 mL) was added to quench the reaction. The mixture was extracted with EtOAc (3×10 mL) and the combined organic layer was dried over Na$_2$SO$_4$ and concentrated in vacuo to provide Int 5-3 (240 mg, 85%). $^1$H NMR (CD$_3$OD): δ 7.81 (s, 1H), 7.19-7.23 (m, 2H), 7.05-7.10 (m, 2H), 6.91 (s, 1H), 5.65-5.71 (m, 1H), 3.98-3.99 (m, 1H), 3.61-3.64 (m, 1H), 3.35-3.41 (m, 1H), 2.94-3.06 (m, 4H), 2.30-2.33 (m, 4H), 1.81 (d, J=7.2 Hz, 3H), 1.40 (s, 9H). MS (ESI): m/z (M+H)+ 433.

Step D Preparation of Int 5-4

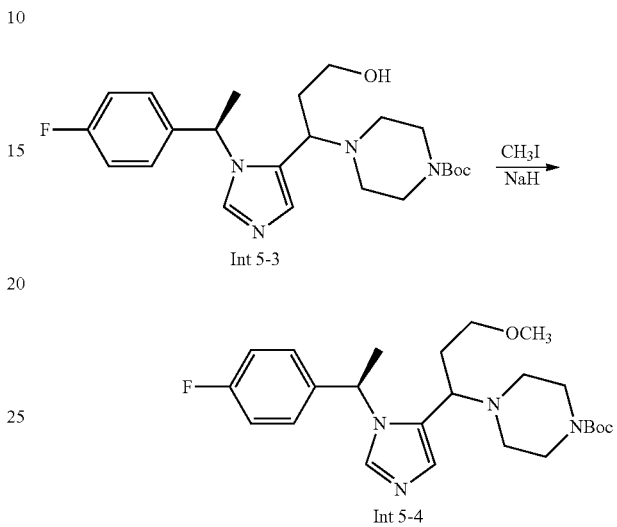

To a solution of Int 5-3 (130 mg, 0.3 mmol) in THF (5 mL) was added NaH (12 mg, 0.3 mmol) at −10° C. Stirring was continued for 30 min before CH$_3$I (42.7 mg, 0.3 mmol) was added. The mixture was allowed to stir at −10° C. for 2 h, quenched with water (4 mL) and extracted with EtOAc (4×5 mL). The organic layer was dried over Na$_2$SO$_4$ and concentrated in vacuo to provide the resulting residue Int 5-4 (130 mg, 97%) which was used in next step without further purification. MS (ESI): m/z (M+H)+ 447.

Step E Preparation of Int 5-5

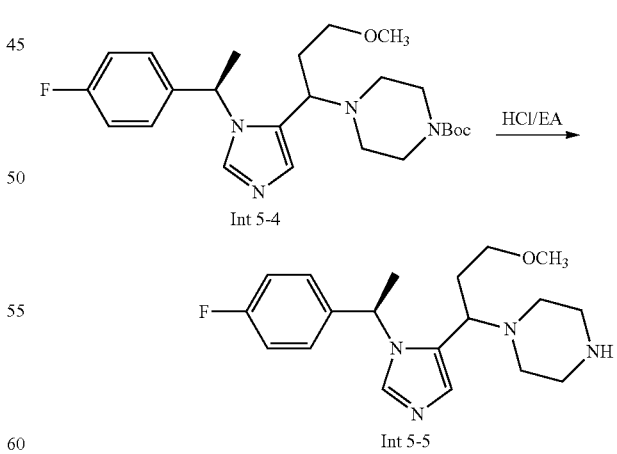

The solution of Int 5-4 (200 mg, 0.4 mmol) in HCl/EtOAc (10 mL) was allowed to stir at 0° C. for 1 hour. The reaction mixture was concentrated in vacuo to provide crude Int 5-5 which was used in the next step without further purification. MS (ESI): m/z (M+H)+ 347.

Step F Preparation of Compound 36

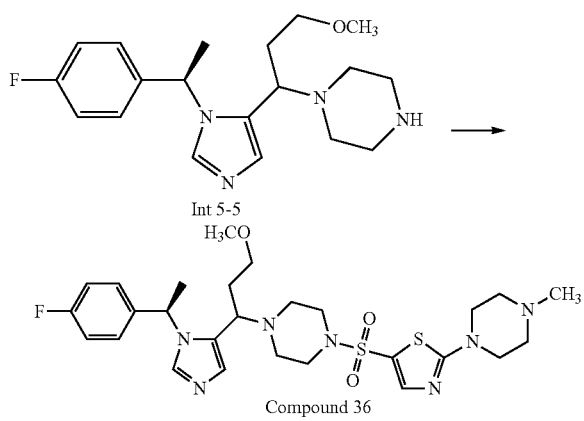

To a solution of Int 5-5 (150 mg, 0.43 mmol) in DMF (10 mL) was added Et₃N (227 mg, 2.25 mmol) at 0° C. After stirring for 10 minutes, 4-(4-methyl-piperazin-1-yl)-thiazole-2-sulfonyl chloride (252 mg, 0.90 mmol) was added and the mixture was allowed to stir at 0° C. for 30 minutes. The reaction mixture was filtered and the filtrate was purified using preparative HPLC to provide Compound 36.

Diastereomer A (22 mg, 17%). ¹H NMR (CD₃OD): δ 7.81 (s, 1H), 7.46 (s, 1H), 7.06-7.09 (m, 2H), 6.86-6.91 (m, 3H), 5.51-5.57 (m, 1H), 3.98-4.01 (m, 1H), 3.41-3.60 (m, 5H), 3.21-3.25 (m, 4H), 2.49-2.68 (m, 12H), 2.34 (s, 3H), 2.12-2.18 (m, 1H), 1.86-1.98 (m, 1H), 1.76 (d, J=7.2 Hz, 3H). MS (ESI): m/z (M+H)⁺ 592.

Diastereomer B (30 mg, 22%). ¹H NMR (CD₃OD): δ 7.96 (s, 1H), 7.54 (s, 1H), 7.01-7.04 (m, 4H), 6.92 (s, 1H), 5.59-5.65 (m, 1H), 3.56-3.76 (m, 5H), 3.19-3.23 (m, 1H), 2.87-2.97 (m, 8H), 2.46-2.63 (m, 8H), 2.34 (s, 3H), 1.98-2.01 (m, 1H), 1.86-1.92 (m, 1H), 1.79 (d, J=7.2 Hz, 3H). MS (ESI): m/z (M+H)⁺ 592.

Example 6

Preparation of Compound 37

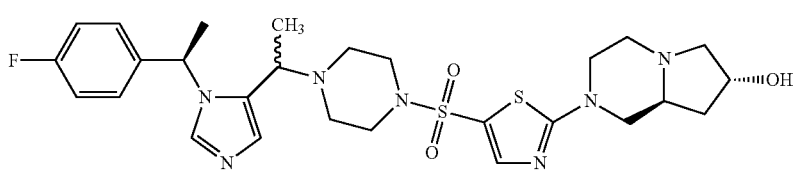

37

Step A Preparation of Int 6-1

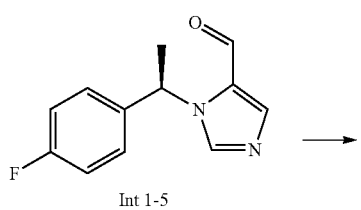

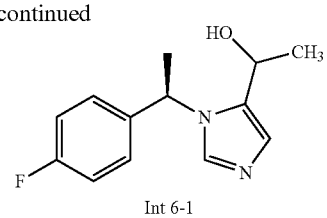

Int 6-1

CH₃MgBr (5 mL, 15 mmol) was added drop wise to a mixture of compound Int 1-5 (1.09 g, 5 mmol) in anhydrous THF (70 mL) at 0° C. The mixture was allowed to stir at 0° C. for 1 hour, quenched with sat NH₄Cl and extracted with ethyl acetate (3×50 mL). The organic washings were washed with brine, dried, concentrated in vacuo to provide 1.05 g (90%) of compound Int 6-1 as a yellow oil. MS-ESI (m/z): 235 (M+H)⁺.

Step B—Synthesis of Int 6-2

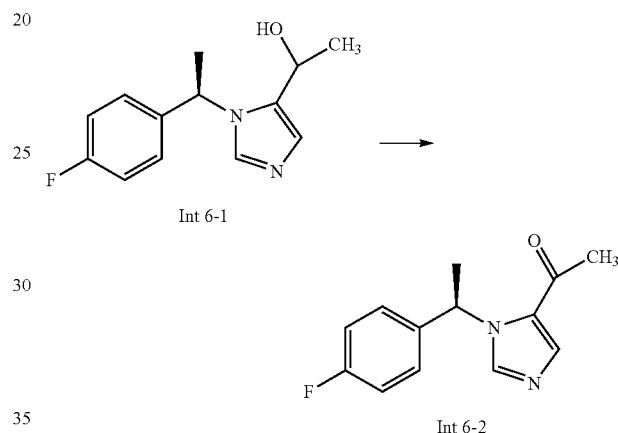

To a solution of compound Int 6-1 (1.05 g, 4.5 mmol) in dioxane (10 mL) was added MnO₂ (1.95 g, 22.5 mmol) and the mixture was allowed to stir at 80° C. for 4 hours. The reaction mixture was filtered through Celite and concentrated in vacuo. The resulting residue was purified using column chromatography to provide 1.02 g (98%) of compound Int 6-2 as yellow oil (yield: 98%). MS-ESI (m/z): 233 (M+H)⁺.

Step C—Synthesis of Int 6-3

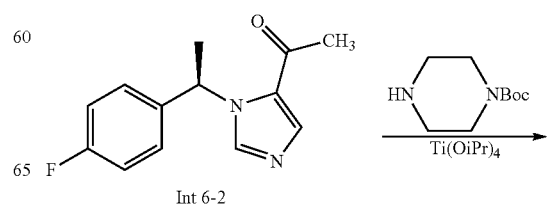

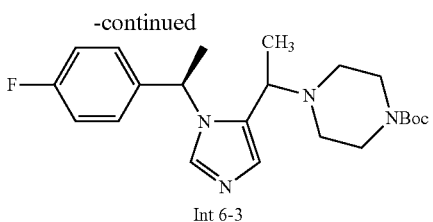

Int 6-3

A mixture of compound Int 6-2 (1.02 g, 4.37 mmol), Boc-piperazine (0.82 g, 4.4 mmol) and Ti(OiPr)$_4$ (1 mL) in anhydrous THF (1 mL) was allowed to stir at 90° C. for about 15 hours under N$_2$. The reaction mixture was cooled and THF (10 mL) and NaBH(OAc)3 (4.6 g, 21.8 mmol) were added and the mixture was allowed to stir at 80° C. for 1 hour. The mixture was cooled then quenched with water and extracted with ethyl acetate (3×50 mL). The organic washings were washed with brine, dried over sodium sulfate, filtered and concentrated in vacuo to provide the resulting residue which was purified using column chromatography to provide 0.76 g (43%) of compound Int 6-3 as yellow oil. MS-ESI (m/z): 403 (M+H)$^+$.

Step D—Synthesis of Int 6-4

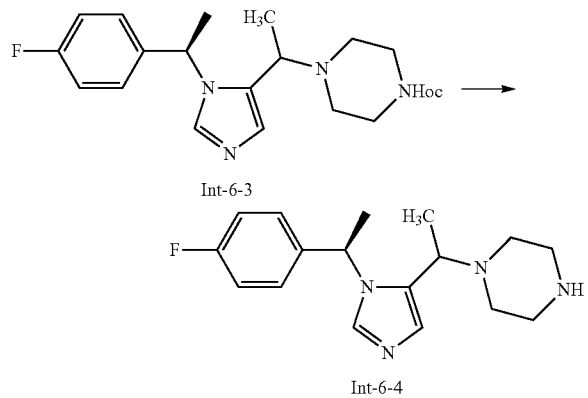

A mixture of compound Int 6-4 (0.76 g, 1.89 mmol) in HCl/EtOAc (10 mL) was allowed to stir at room temperature for 30 minutes then concentrated in vacuo and used in the next step without further purification. MS-ESI (m/z): 303 (M+H)$^+$.

Step E—Synthesis of Int 6-5

To a mixture of compound Int 6-4 (570 mg, 1.89 mmol) and triethylamine (606 mg, 6 mmol) in DMF (3 mL) was added in portions N-acetyl-2-aminothiazole-5-sulfonyl chloride (480 mg, 2 mmol). The mixture was allowed to stir at room temperature for 30 min, and then extracted with ethyl acetate (3×50 mL). The organic layer was washed with brine, dried over sodium sulfate, filtered and concentrated in vacuo to provide the resulting residue which was purified using column chromatography to provide 0.77 g (82%) of compound Int 6-5 as yellow solid. MS-ESI (m/z): 507 (M+H)$^+$.

Step F—Synthesis of Int 6-6

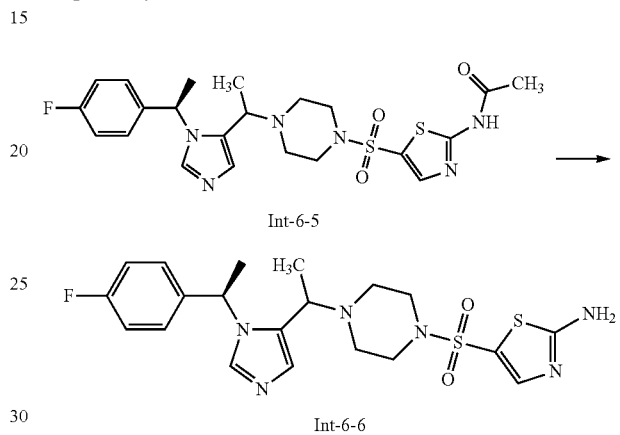

A mixture of compound Int 6-5 (770 mg, 1.52 mmol) in EtOH/6N HCl (10/10 mL) was allowed to stir at 80° C. for 1 hour, cooled and concentrated in vacuo. The resulting residue was diluted with EtOAc (20 mL), basified with saturated NaHCO$_3$ solution then extracted with ethyl acetate (3×30 mL). The organic layer was washed with brine, dried over sodium sulfate, filtered and in vacuo to provide the resulting residue which was purified using column chromatography to provide 0.58 g (82%) of compound Int 6-6 as yellow solid. MS-ESI (m/z): 465 (M+H)$^+$.

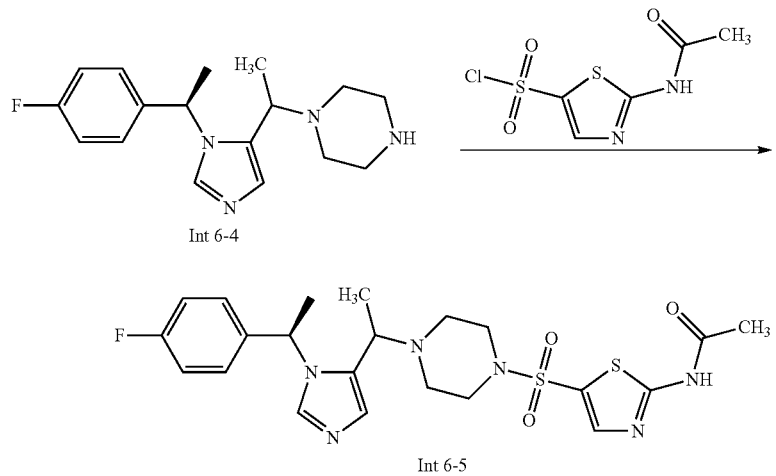 [SMILES: CC(c1cncn1[C@H](C)c1ccc(F)cc1)N1CCNCC1 ; CC(=O)Nc1ncc(S(=O)(=O)Cl)s1 ; CC(=O)Nc1ncc(S(=O)(=O)N2CCN(C(C)c3cncn3[C@H](C)c3ccc(F)cc3)CC2)s1]

Step G—Synthesis of Int 6-7

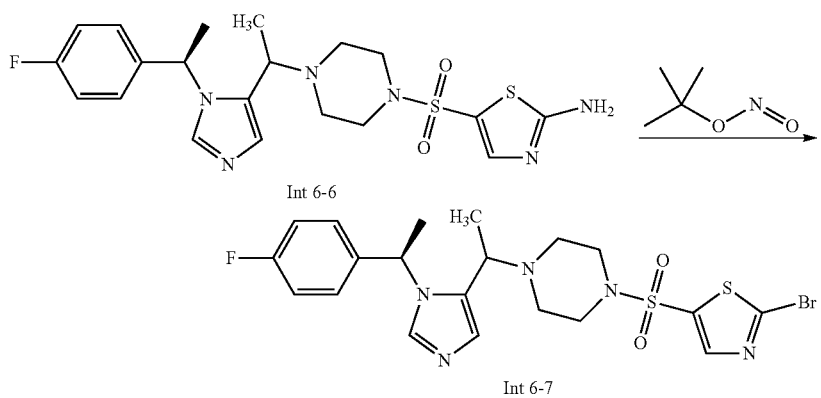

Int 6-6

Int 6-7

To a mixture of tert-butylnitrite (466 mg, 4.52 mmol) in DMF (5 mL) was added compound Int 6-6 (0.52 g, 1.15 mmol). The mixture was allowed to stir at 60° C. for 2 hours then diluted with EtOAc (20 mL) and washed with concentrated in vacuo NH$_4$OH. The organic washings were dried over sodium sulfate, filtered and in vacuo to provide the resulting residue which was purified using column chromatography to provide 0.32 g (52%) of compound Int 6-7 as yellow solid. MS-ESI (m/z): 528, 530 (M+H)$^+$.

Step H—Synthesis of Compounds 37a and 37b

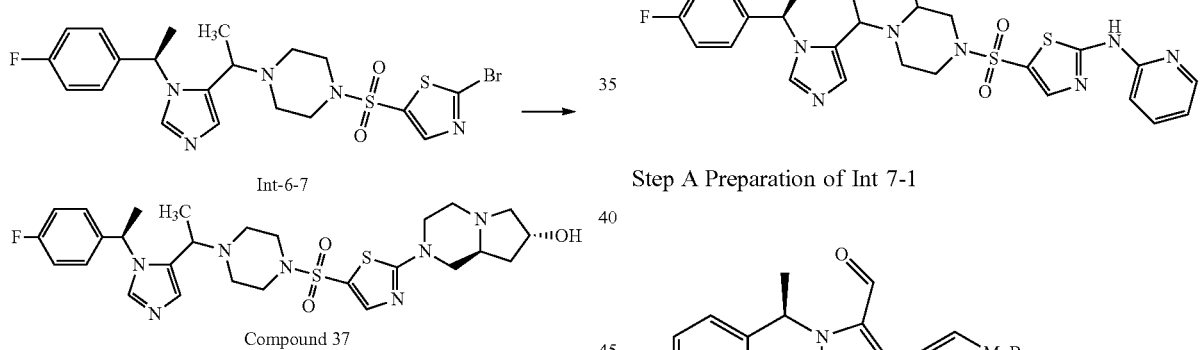

Int-6-7

Compound 37

A mixture of compound Int 6-7 (300 mg, 0.56 mmol), (7R,8aS)-octahydropyrrolo[1,2-a]piperazin-7-ol (0.62 mmol) and K$_2$CO$_3$ (207 mg, 1.5 mmol) in CH$_3$CN (5 mL) was allowed to stir at 80° C. for about 15 hours. The mixture was cooled and extracted with EtOAc/H$_2$O. The organic extracts were washed with brine, dried, concentrated in vacuo and purified using HPLC to provide 80 mg (~25%) of each diastereomer 37a and 37b.

Compound 37a: $^1$H NMR (CD3OD) δ: 7.83 (s, 1H), 7.44 (s, 1H), 7.05-7.01 (m, 2H), 6.88-6.82 (m, 3H), 5.60 (q, J=6.8 Hz, 1H), 4.43-4.38 (m, 1H), 4.16 (d, J=12.8 Hz, 1H), 4.08-4.03 (m, 1H), 3.95 (d, J=12.8 Hz, 1H), 3.50-3.46 (m, 1H), 3.11-3.09 (m, 1H), 2.92-2.86 (m, 1H), 2.68 (br, 2H), 2.55-2.42 (m, 8H), 2.40-2.39 (m, 1H), 2.18-2.14 (m, 5H), 1.81-1.73 (m, 4H). MS-ESI (m/z): 590 (M+H)$^+$.

Compound 37b $^1$H NMR (CD3OD) δ: 7.91 (s, 1H), 7.55 (s, 1H), 7.07-7.01 (m, 4H), 6.88 (s, 1H), 5.81 (q, J=6.8 Hz, 1H), 4.41-4.38 (m, 1H), 4.12 (d, J=12.8 Hz, 1H), 3.95 (d, J=12.8 Hz, 1H), 3.62-3.58 (m, 1H), 3.49-3.45 (m, 1H), 3.32-3.28 (m, 1H), 3.24-3.00 (m, 5H), 2.90-2.84 (m, 1H), 2.59-2.36 (m, 6H), 2.16-2.12 (m, 1H), 1.79-1.75 (m, 5H), 1.21 (d, J=6.8 Hz, 3H). MS-ESI (m/z): 590 (M+H)$^+$.

Example 7

Preparation of Compound 38

38

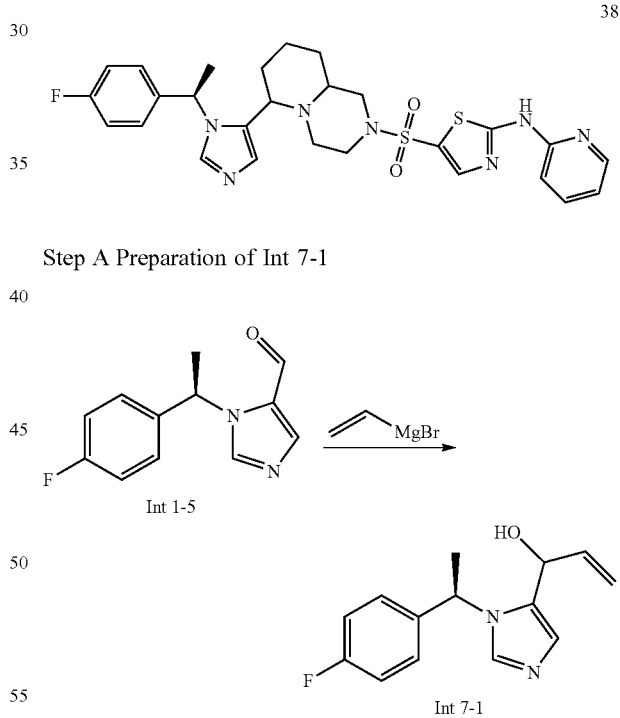

Step A Preparation of Int 7-1

Int 1-5

Int 7-1

To a solution of Int 1-4 (5.0 g, 22.9 mmol) in THF (80 mL) was added ethyl magnesium bromide (25 mL, 25 mmol) at 0° C. The mixture was allowed to stir at room temperature for about 15 hours then quenched with saturated NH$_4$Cl solution (20 mL) and extracted with EtOAc (3×30 mL). The combined organic layer was dried over sodium sulfate, filtered and in vacuo and the resulting residue was purified using column chromatography (EtOAc/petroleum ether=1/3) to provide Int 7-1 (4.5 g, 80%). MS (ESI): m/z (M+H)$^+$ 247.

Step B—Synthesis of Int 7-2

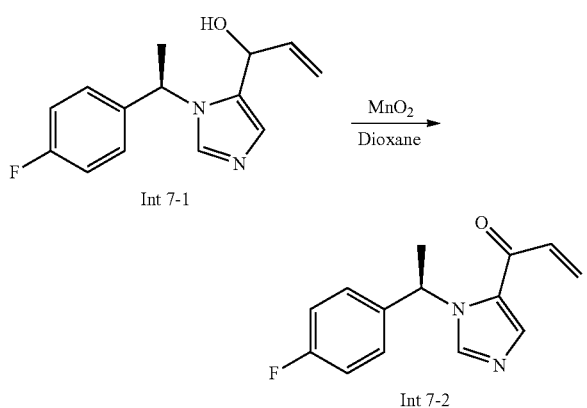

A mixture of Int 7-1 (700 mg, 2.8 mmol) and MnO$_2$ (3.7 g, 42.7 mmol) in dioxane (20 mL) was heated to 60° C. for 17 hours. The reaction mixture was cooled and filtered through Celite and the filtrate was concentrated in vacuo to provide Int 7-2 which was used into the next step without further purification (500 mg, 78%). $^1$H NMR (CDCl3) δ 7.87 (s, 1H), 7.78 (s, 1H), 7.17-7.25 (m, 2H), 6.90-7.03 (m, 3H), 6.50 (d, J=3.2 Hz, 1H), 6.39 (q, J=1.2 Hz, 1H), 5.80 (d, J=1.2 Hz, 1H), 3.78 (s, 1H), 3.69 (s, 1H), 1.83 (d, J=7.2 Hz, 3H). MS (ESI): m/z (M+H)$^+$ 245.

Step C—Synthesis of Int 7-3

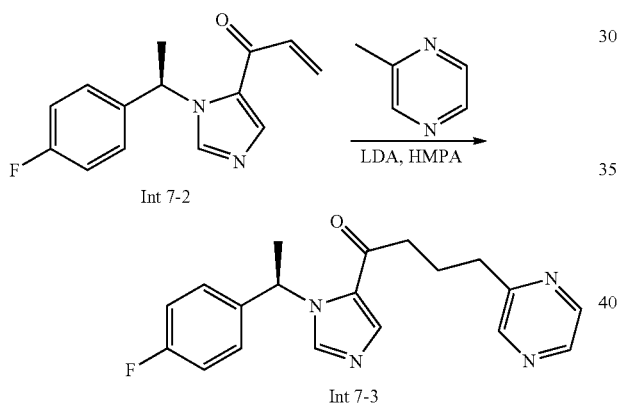

To a solution of 2-methylpyrazine (272 mg, 2.9 mmol) and HMPA (520 mg, 2.9 mmol) in THF (2.5 mL) was added LDA (1.6 mL, 3 mmol) at −78° C. dropwise. The mixture was allowed to stir at −78° C. for 30 minutes before a solution of Int 7-2 (600 mg, 2.45 mmol) in 2 mL of THF was added. The mixture was allowed to warm to room temperature for 3 hours before it was quenched with 10 mL of saturated NH$_4$Cl solution. The resulting mixture was extracted with EtOAc (3×10 mL) and the combined organic washings were dried over sodium sulfate, filtered and in vacuo. The resulting residue was purified using column chromatography (25% EtOAc/petroleum ether) to provide Int 7-3 (100 mg, 12%). MS (ESI): m/z (M+H)$^+$ 339.

Step D—Synthesis of Int 7-4

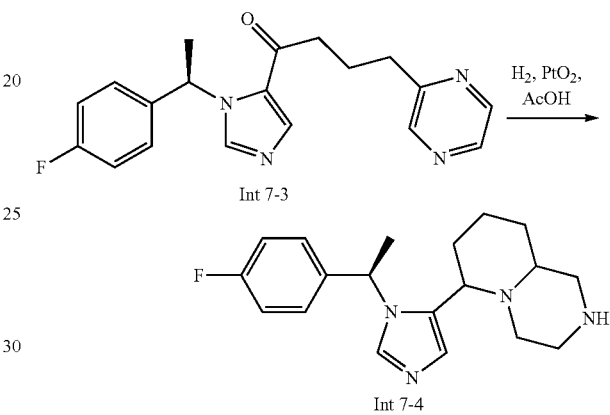

A mixture of Int 7-3 (400 mg, 1.03 mmol) and PtO$_2$ (50 mg) in AcOH (10 mL) was hydrogenated under 1 atmosphere of H$_2$ pressure for about 15 hours. The reaction was filtered and the filtrate was concentrated in vacuo to leave a residue that was purified using HPLC to provide Int 7-4 (200 mg, 59%). MS (ESI): m/z (M+H)$^+$ 329.

Step E—Synthesis of Compound 38

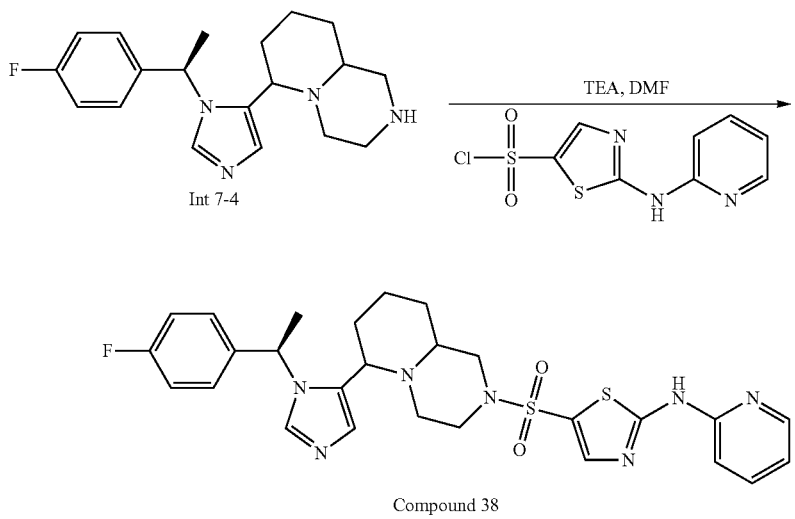

To a solution of Int 7-4 (100 mg, 0.3 mmol) and TEA (101 mg, 1.0 mmol) in DMF (4 mL) was added the sulfonyl chloride (65 mg, 0.3 mmol) at 0° C. and the reaction mixture was allowed to stir at room temperature for 2 hours. The reaction mixture was purified using HPLC to provide Compound 38 (80 mg) as three diastereomers.

Diastereomer A: $^1$H NMR (CD$_3$OD) δ 8.39 (d, J=6.0 Hz, 1H), 7.87 (s, 1H), 7.71-7.77 (m, 2H), 7.00-7.07 (m, 5H), 6.94 (s, 2H), 5.46 (t, J=9.2 Hz, 1H), 4.02 (s, 1H), 3.05-3.09 (m, 1H), 2.80 (d, J=10.4 Hz, 2H), 2.40 (s, 2H), 1.90-1.95 (m, 2H), 1.77 (d, J=6.8 Hz, 4H), 1.63 (d, J=8.0 Hz, 3H), 1.38-1.53 (m, 2H). MS (ESI): m/z (M+H)$^+$ 568.

Diastereomer B: $^1$H NMR (CD$_3$OD) δ 8.38 (d, J=4.4 Hz, 1H), 7.91 (s, 1H), 7.72-7.78 (m, 2H), 7.12 (s, 2H), 7.00-7.06 (m, 4H), 6.89 (s, 1H), 5.72-5.88 (m, 1H), 3.48 (d, J=8.0 Hz, 1H), 2.61 (d, J=12.0 Hz, 1H), 2.50 (s, 1H), 2.32 (t, J=10.4 Hz, 1H), 2.21 (d, J=10.8 Hz, 1H), 1.59-1.77 (m, 7H), 1.44 (d, J=9.2 Hz, 3H), 1.25 (d, J=14.4 Hz, 2H). MS (ESI): m/z (M+H)$^+$ 568.

Diastereomer C: $^1$H NMR (CD$_3$OD) δ 8.41 (d, J=4.8 Hz, 1H), 7.94 (d, J=5.6 Hz, 1H), 7.71-7.78 (m, 2H), 7.01-7.08 (m, 4H), 6.86 (s, 3H), 3.47 (d, J=6.8 Hz, 1H), 3.24 (t, J=2.0 Hz, 1H), 2.68-2.74 (m, 1H), 2.20 (s, 2H), 1.92-2.01 (m, 2H), 1.77-1.78 (m, 5H), 1.61-1.64 (m, 2H), 1.33 (s, 3H). MS (ESI): m/z (M+H)$^+$ 568.

Example 8

Preparation of Compound 39

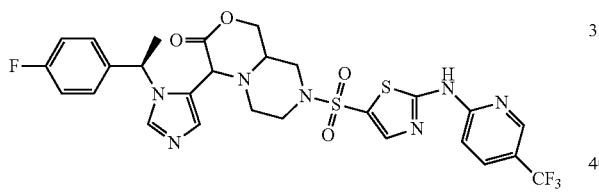

Step A Preparation of Int 8-1

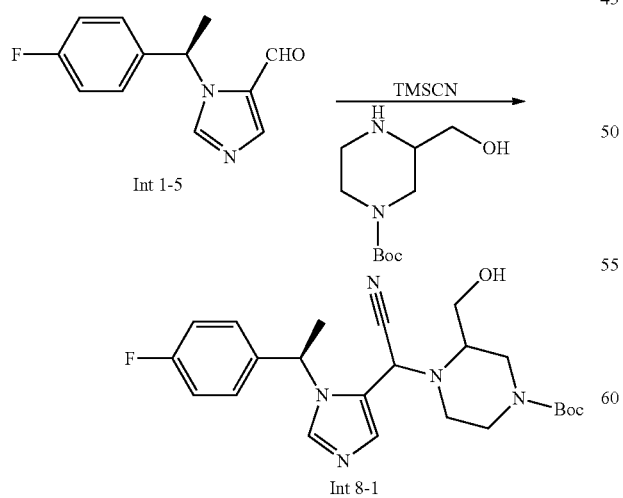

To a solution of Int 1-5 (300 mg, 1.37 mmol) in 10 mL of diethyl ether was added trimethylsilyl cyanide (151 mg, 1.52 mmol) and zinc iodide (122 mg, 0.38 mmol) at room temperature under nitrogen. The mixture was cooled to 0° C. and stirred for 5 minutes. A solution of tert-butyl 3-(hydroxymethyl)piperazine-1-carboxylate (300 mg, 1.22 mmol) was added followed by triethylamine (281 mg, 2.68 mmol) and the mixture was allowed to stir at 50° C. for about 15 hours. The mixture was cooled to room temperature and 10 mL of saturated aqueous solution of K$_2$CO$_3$ was added. The resulting aqueous solution was extracted with EtOAc (3×5 mL). The organic layer was dried over Na$_2$SO$_4$, filtered and concentrated in vacuo. The resulting residue was purified using flash chromatography (50% EtOAc/petroleum ether) to provide the desired product Int 8-1 (200 mg, 32%). $^1$H NMR (CDCl$_3$): δ 8.67 (s, 1H), 7.54 (s, 1H), 7.14-7.17 (m, 2H), 7.05-7.09 (m, 2H), 6.04-6.09 (m, 1H), 5.61 (s, 1H), 3.89-4.02 (m, 2H), 3.67-3.73 (m, 1H), 2.82-2.88 (m, 1H), 2.61-2.64 (m, 1H), 2.49-2.56 (m, 1H), 2.40-2.42 (m, 1H), 2.25-2.27 (m, 1H), 1.83-1.90 (m, 3H), 1.49 (s, 9H). MS (ESI): m/z (M+H)$^+$ 444.23.

Step B—Synthesis of Int 8-2

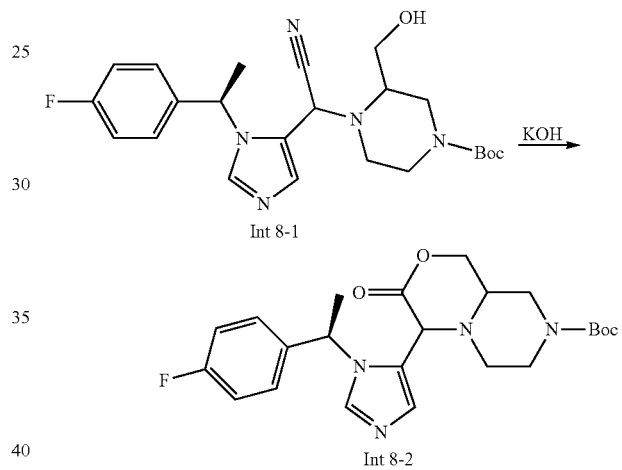

To a solution of Int 8-1 (2 g, 4.5 mmol) in MeOH/H$_2$O (30 mL/10 mL) was added KOH (3.02 g, 54 mmol). The mixture was allowed to stir at 85° C. for about 15 hours before the mixture was cooled to room temperature, adjusted to pH=6 and stirred at 60° C. for 1 hour. The reaction mixture was cooled and concentrated in vacuo to remove MeOH and the resulting aqueous mixture was extracted with EtOAc (3×20 mL). The combined organic phase was dried, filtered and concentrated in vacuo. The resulting residue was purified using flash chromatography (33% EtOAc/petroleum ether) to provide the desired product Int 8-2 (1.3 g, 65%). MS (ESI): m/z (M+H)$^+$ 445

Step C—Synthesis of Int 8-3

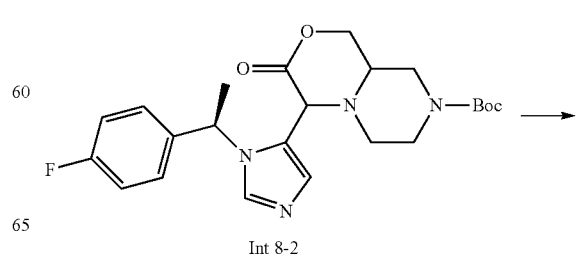

81

-continued

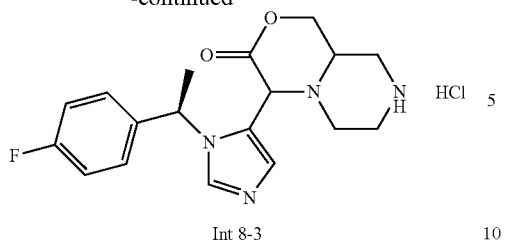

Int 8-3

Compound Int 8-2 (2 g, 4.5 mmol) was dissolved in HCl/EtOAc (20 mL) and the mixture was allowed to stir at room temperature for 1 hour. The formed precipitate was filtered and dried to provide the desired product Int 8-3 (622 mg, 41%). MS (ESI): m/z (M+H)+ 345

Step D—Synthesis of Compound 39

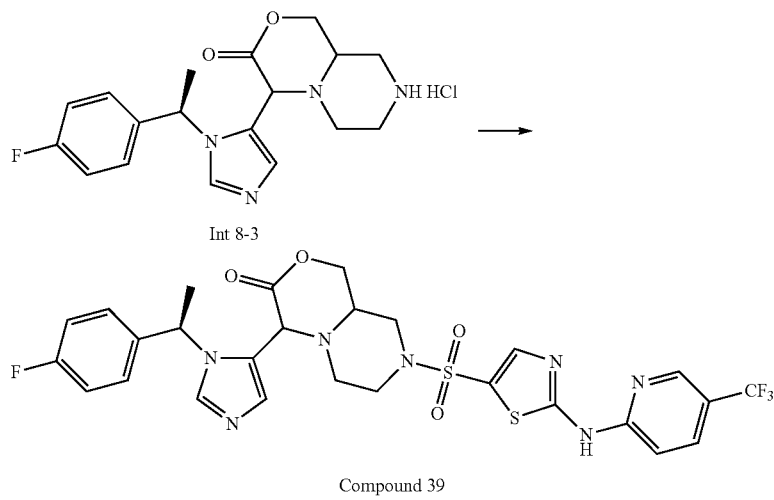

Int 8-3

Compound 39

To a solution of Int 8-3 (200 mg, 0.6 mmol) in DMF (3 mL) was added TEA (0.4 mL) and the mixture was allowed to stir at room temperature for 5 minutes. A solution of 2-(5-(trifluoromethyl)pyridin-2-ylamino)thiazole-5-sulfonyl chloride (246 mg, 0.72 mmol) in DMF (2 mL) was added and the mixture was allowed to stir at room temperature for 20 minutes. The mixture was concentrated in vacuo and purified using HPLC to provide Compound 39A and Compound 39B (90 mg, 25%).

Diastereomer A: $^1$H NMR (CD$_3$OD): δ 9.07 (s, 1H), 8.72 (s, 1H), 8.03 (dd, J$_1$=8.8 Hz, J$_2$=2.0 Hz, 1H), 7.84 (s, 1H), 7.68 (s, 1H), 7.21-7.28 (m, 3H), 6.87 (t, J=8.4 Hz, 2H), 5.63 (q, J=7.2 Hz, 1H), 4.71 (s, 1H), 4.53 (dd, J$_1$=3.6 Hz, J$_2$=11.6 Hz, 1H), 4.33 (t, J=11.2 Hz, 1H), 3.75 (d, J=11.2 Hz, 1H), 3.41 (d, J=11.6 Hz, 1H), 3.03-3.11 (m, 1H), 2.46 (d, J=12.0 Hz, 1H), 2.22-2.28 (m, 1H), 2.04 (t, J=10.8 Hz, 1H), 1.78 (d, J=5.2 Hz, 3H), 1.71-1.72 (m, 1H). MS (ESI): m/z (M+H)+ 652.13.

Diastereomer B: $^1$H NMR (CD$_3$OD): δ 9.14 (s, 1H), 8.69 (s, 1H), 8.02 (d, J=8.8 Hz, 1H), 7.87 (s, 1H), 7.64 (s, 1H), 7.18-7.25 (m, 3H), 7.09-7.13 (m, 2H), 6.00 (q, J=5.2 Hz, 1H), 4.51 (s, 1H), 4.41 (dd, J$_1$=10.8 Hz, J$_2$=2.0 Hz, 1H), 4.19 (t, J=10.8 Hz, 1H), 3.78 (d, J=10.4 Hz, 1H), 3.56-3.59 (m, 1H), 2.98-3.05 (m, 1H), 2.53-2.61 (m, 1H), 2.30 (t, J=10.8 Hz, 1H), 1.96-1.99 (m, 1H), 1.90 (d, J=6.8 Hz, 3H). MS (ESI): m/z (M+H)+ 652.13.

82

Example 9

Preparation of Compound 40

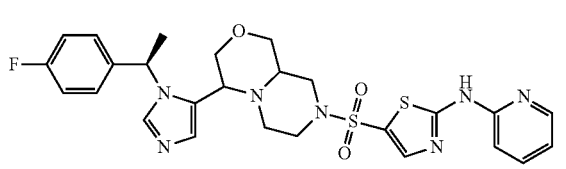

Step A Preparation of Int 9-1

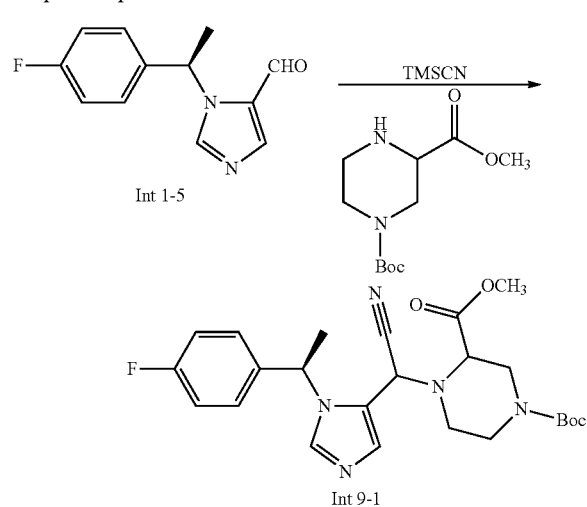

TMSCN (1.5 g, 15 mmol) and K$_2$PdCl$_4$ (326 mg, 1 mmol) was added to the solution of Int 1-5 (2.3 g, 10 mmol) and 1-tert-butyl 3-methyl piperazine-1,3-dicarboxylate (2.44 g, 10 mmol) in H$_2$O (20 mL), the resultant mixture was allowed to stir at r.t. for 48 h, then extracted with EtOAc (3×30 mL), the combined organic layer was concentrated in vacuo and purified using column chromatography (25% EtOAc/petroleum ether) to stir Int 9-1 (1.5 g, 30%). ¹H NMR (CDCl₃): δ 7.98 (s, 1H), 7.32 (s, 1H), 6.99~7.18 (m, 4H), 6.02~6.04 (m, 1H), 5.02 (s, 1H), 3.71 (s, 3H), 3.27~3.30 (m, 1H), 2.64~2.80 (m, 2H), 2.33~2.36 (m, 2H), 2.17~2.25 (m, 2H), 1.82 (s, 3H), 1.38 (s, 9H). MS (ESI): m/z (M+H)⁺ 472.1.

Step B—Synthesis of Int 9-2

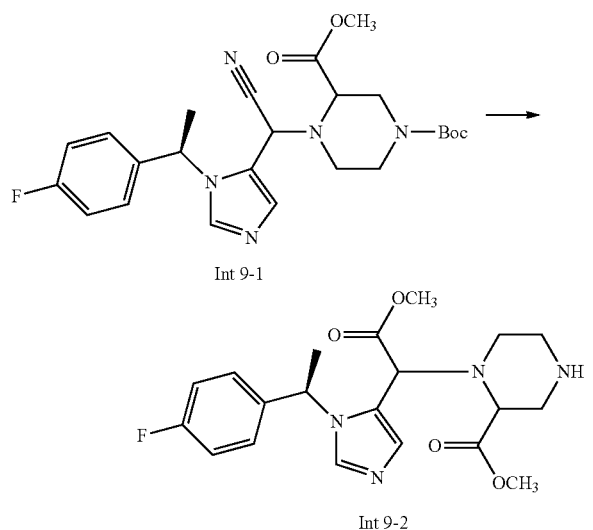

The mixture of Int 9-1 (5 g, 10.6 mmol) in HCl/MeOH (50 mL) was allowed to stir at 70° C. for about 15 hours. The mixture was cooled and concentrated in vacuo to provide the crude Int 9-2 which was used into the next step without further purification. MS (ESI): m/z (M+H)⁺ 405.

Step C—Synthesis of Int 9-3

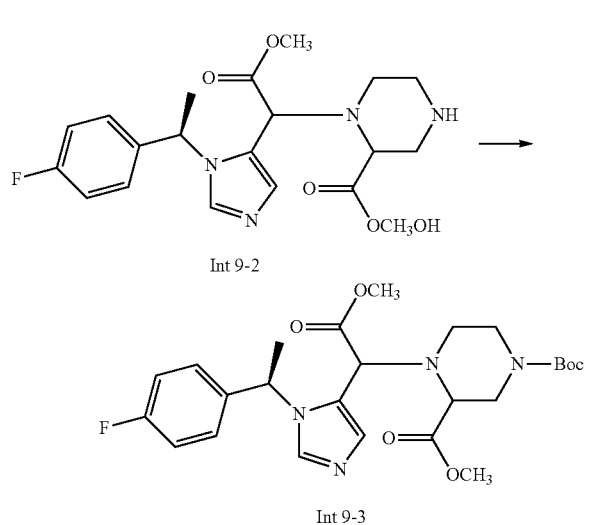

To a solution of Int 9-2 (5 g, 11.4 mmol) in MeOH (50 mL) was added TEA (3 mL) and (Boc)₂O under nitrogen atmosphere. The mixture was allowed to stir at room temperature for 3 hours then concentrated in vacuo and purified using column chromatography (petroleum ether:EtOAc: DCM=3:2:1) to provide the product Int 9-3 (1.7 g, 30%). MS (ESI): m/z (M+H)⁺ 505.

Step D—Synthesis of Int 9-4

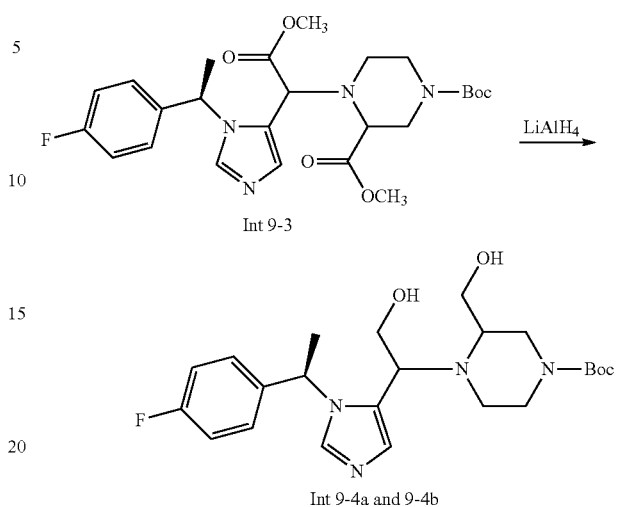

To a solution of compound Int 9-3 (1.78 g, 3.5 mmol) in THF (20 mL) was added LiAlH₄ (402 mg, 10.6 mmol) at 0° C. and the reaction mixture was allowed to stir at room temperature for 3 hours. Water (1 mL) was added to quench the reaction and the mixture was extracted with CH₂Cl₂ (3×10 mL). The combined organic washings were dried over Na₂SO₄ and concentrated in vacuo to provide the crude mixture (800 mg) which was purification by HPLC to provide two isomers Int 9-4a (200 mg, 13%) and Int 9-4b (200 mg, 13%). MS (ESI): m/z (M+H)⁺ 449.

Step E—Synthesis of Int 9-5a

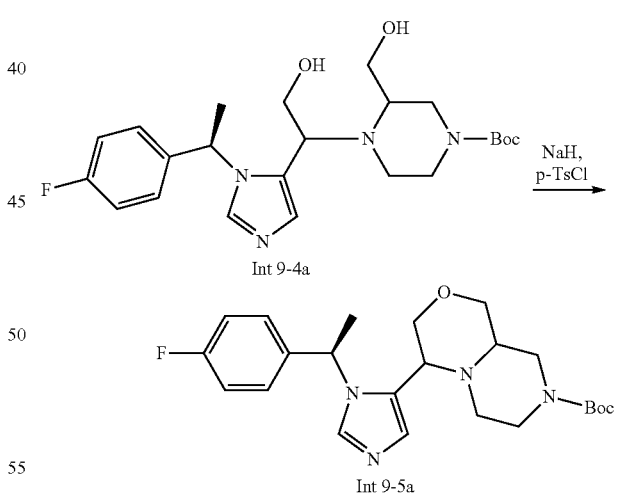

To a solution of Int 9-4a (80 mg, 0.18 mmol) in THF (2 mL) was added NaH (22 mg, 0.54 mmol) at 0° C. After stirred for 30 minutes, a solution of p-TsCl (24 mg, 0.13 mmol) in THF (1 mL) was added dropwise. The mixture was allowed to stir for about 15 hours at for 16 hours. Water (3 mL) was added to the solution and extracted with EtOAc (3×5 mL). The organic layer was dried over Na₂SO₄ and concentrated in vacuo to provide the product Int 9-4a (65 mg, 83%). MS (ESI): m/z (M+H)⁺ 431.2.

Step F—Synthesis of Int 9-6a

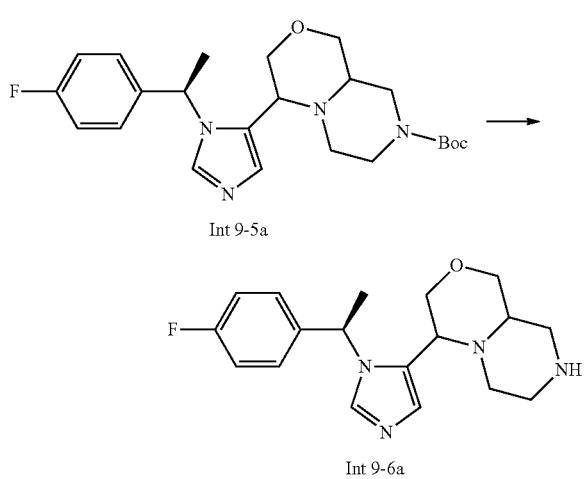

Compound Int 9-5a (65 mg, 0.15 mmol) was dissolved in HCl/EtOAc (6 mL) and the mixture was allowed to stir at room temperature for 40 minutes. The mixture was concentrated in vacuo to provide the crude compound Int 9-6a (40 mg, 80%). MS (ESI): m/z (M+H)$^+$ 331.2.

Step G—Synthesis of Compound 40

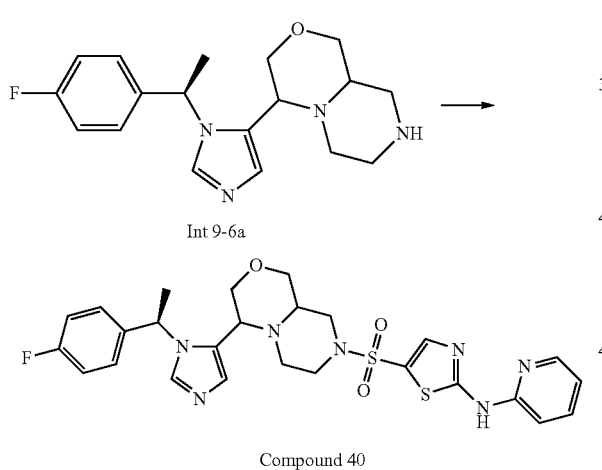

To a solution of Int 9-6a (40 mg, 0.11 mmol) in DMF (3 mL) was added TEA (0.5 mL) at 0° C. The mixture was allowed to stir for 5 minutes then 2-(pyridin-2-ylamino)thiazole-5-sulfonyl chloride (30 mg, 0.11 mmol) was added. The mixture was allowed to stir at room temperature for 20 minutes. The reaction mixture was directly purified using HPLC to provide Compound 40 (14 mg, 22%). $^1$H NMR (CD$_3$OD): δ 9.29 (s, 1H), 8.37 (d, J=4.4 Hz, 1H), 7.73-7.80 (m, 3H), 7.00-7.17 (m, 6H), 5.80-5.85 (q, J=6.4 Hz, 1H), 3.80-3.87 (m, 2H), 3.60 (d, J=9.2 Hz, 1H), 3.48 (d, J=12.0 Hz, 1H), 3.41 (d, J=6.0 Hz, 1H), 3.32-3.35 (m, 1H), 3.18-3.24 (m, 1H), 3.01 (d, J=11.6 Hz, 1H), 2.87 (t, J=10 Hz, 1H), 2.79 (t, J=10.4 Hz, 1H), 2.32 (q, J=11.6 Hz, 2H), 1.93 (d, J=6.8 Hz, 3H). MS (ESI): m/z (M+H)$^+$ 570.

Example 10

Preparation of Compound 41

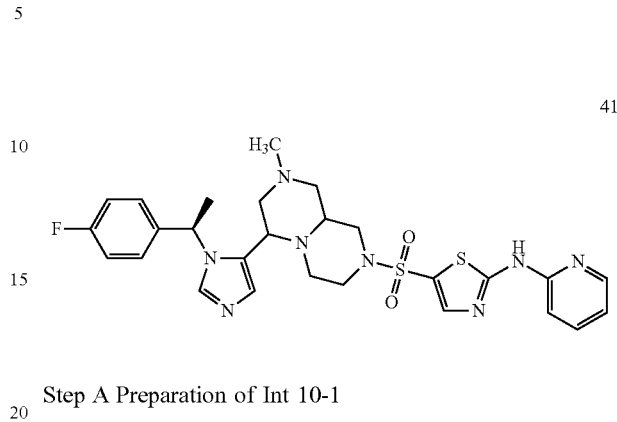

Step A Preparation of Int 10-1

To a solution of Int 9-1 (1.1 g, 2.3 mmol) in MeOH (5 mL) was added Ni (700 mg, 12 mmol) and the resulting mixture was allowed to stir at 50° C. under H$_2$ (50 psi) for 4 hours. The mixture was cooled and filtered through Celite and purified using preparative HPLC to provide compound Int 10-1 (700 mg, 68%). $^1$H NMR (CDCl$_3$): δ 8.64 (s, 1H), 7.81 (s, 1H), 7.28~7.32 (m, 4H), 5.67~5.70 (m, 2H), 3.72~3.78 (m, 3H), 2.67~2.98 (m, 7H), 1.30~1.33 (m, 3H). MS (ESI): m/z (M+H)$^+$ 444.1.

Step B Preparation of Int 10-2

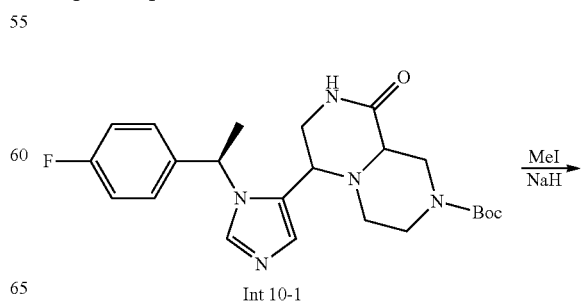

Step D Preparation of Int 10-4

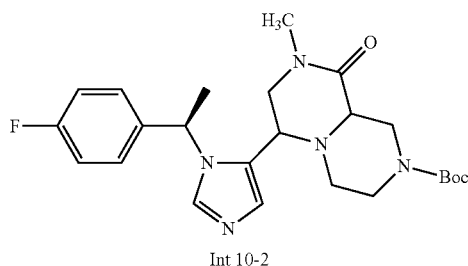

Int 10-2

NaH (40 mg, 1 mmol) was added to the solution of Int 10-1 (110 mg, 0.25 mmol) in THF (5 mL) and the resulting mixture was allowed to stir at room temperature for 0.5 hours before Met (37 mg, 0.26 mg) was added. The reaction was allowed to stir for about 15 hours then quenched with water (5 mL), extracted with EtOAc (3×5 mL). The combined organic washings were concentrated in vacuo and purified using prepreparative TLC to provide compound Int 10-2 (100 mg, 90%). $^1$H NMR (CDCl3) δ 7.58 (s, 1H), 7.50 (s, 1H), 6.96~6.99 (m, 4H), 5.27~5.32 (m, 1H), 3.08~3.27 (m, 4H), 2.69 (s, 3H), 2.16~2.33 (m, 6H), 1.67~1.69 (m, 3H), 1.29 (s, 9H). MS (ESI): m/z (M+H)$^+$ 458.1.

Step C Preparation of Int 10-3

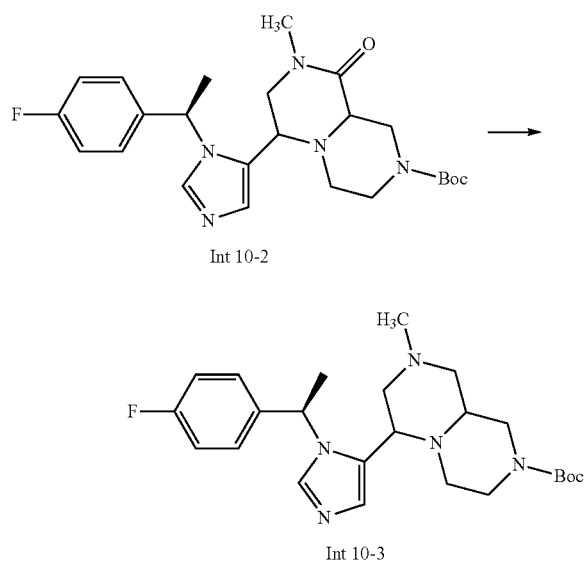 [SMILES: C[C@H](c1ccc(F)cc1)n1cncc1C1CN(C)C(=O)C2CN(C(=O)OC(C)(C)C)CCN21 ; C[C@H](c1ccc(F)cc1)n1cncc1C1CN(C)CC2CN(C(=O)OC(C)(C)C)CCN21]

LiAlH$_4$ (150 mg, 4 mmol) was added to the solution of Int 10-2 (360 mg, 1 mmol) in THF (5 mL) at 0° C. The reaction mixture was allowed to stir at room temperature for about 15 hours. The reaction was quenched with MeOH and filtered through Celite and the mixture was purified using prepreparative TLC to provide compound Int 10-3 (300 mg, 88%). $^1$H NMR (CD$_3$OD): δ 7.92 (s, 1H), 7.81 (s, 1H), 7.01~7.22 (m, 5H), 3.33~3.56 (m, 5H), 3.33 (s, 3H), 2.17~2.25 (m, 7H), 1.79~1.80 (m, 3H). MS (ESI): m/z (M+H)$^+$ 344.1.

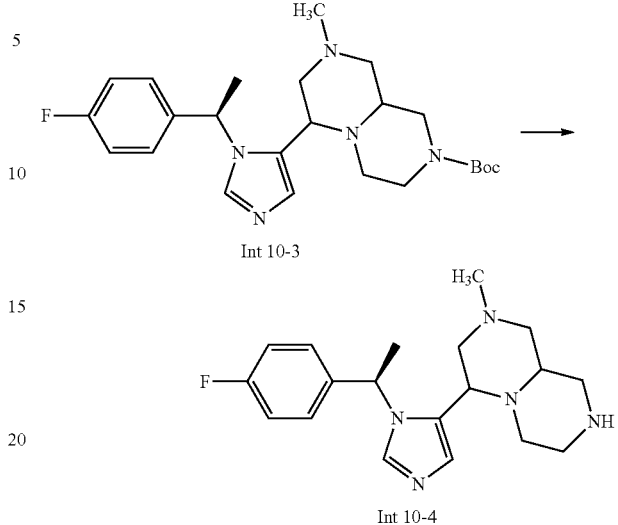

TFA (2 mL) was added to the solution of Int 10-3 (500 mg) in DCM (10 mL) and the resulting mixture was allowed to stir at room temperature for 2 h, then concentrated in vacuo to provide the crude Int 10-4 (360 mg, 92%) which was used without further purification. MS (ESI): m/z (M+H)$^+$ 444

Step E Preparation of Compound 41

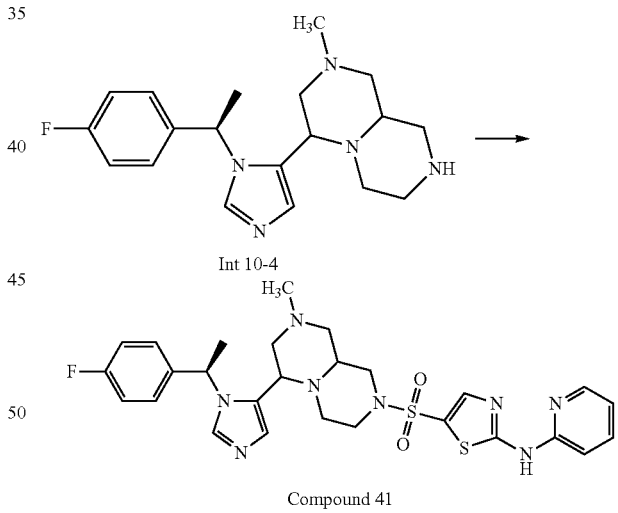

2-(pyridin-2-ylamino)thiazole-5-sulfonyl chloride (55 mg, 0.2 mmol) was added to a solution of Int 10-4 (60 mg, 0.18 mmol) and TEA (0.1 g, 1 mmol) in DCM (5 mL). The resulting mixture was allowed to stir for 12 h, then concentrated in vacuo and purified using preparative HPLC to provide compound 41 (20.6 mg, 19.8%). $^1$H NMR (CD$_3$OD): δ 9.3~39.36 (m, 1H), 8.33~8.39 (m, 1H), 7.63~7.79 (m, 3H), 7.31~7.34 (m, 1H), 6.75~7.13 (m, 5H), 5.75~5.78 (m, 1H), 3.38~3.82 (m, 5H), 2.76~3.11 (m, 7H), 2.43~2.64 (m, 2H), 1.81~1.93 (m, 3H), 1.08~1.25 (m, 1H). MS (ESI): m/z (M+H)$^+$ 583.1.

Example 11

Preparation of Compound 42

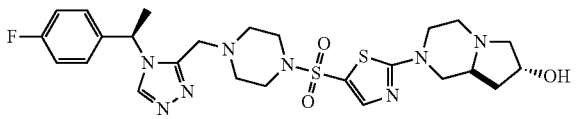

Step A Preparation of Int 11-1

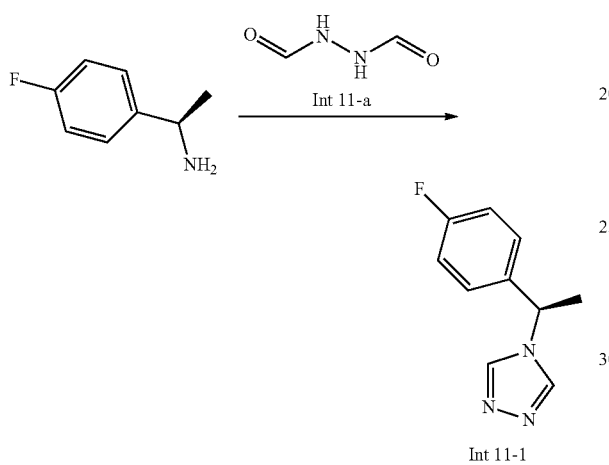

To a solution of compound (R)-4-fluoro-β-methylbenzylamine HCl (1.32 g, 7.57 mmol) and Int 11-a (2 g, 22.7 mmol) in pyridine (40 mL) was added TMSCl (12.7 g, 113 mmol) and TEA (5.3 g, 53 mmol). The mixture was allowed to stir at 80° C. for about 15 hours, cooled then treated with 200 mL of EtOAc. The mixture was filtered and the filtrate was concentrated in vacuo and chromatographed to provide 0.61 g (42%) of compound Int 11-1 as yellow oil. $^1$H NMR (CD3OD) δ 8.66 (s, 2H), 7.43-7.39 (m, 2H), 7.18-7.14 (m, 2H), 5.69 (q, J=6.8 Hz, 1H), 1.88 (d, J=6.8 Hz, 3H). MS-ESI (m/z): 192 (M+H)$^+$.

Step B—Synthesis of Int 11-2

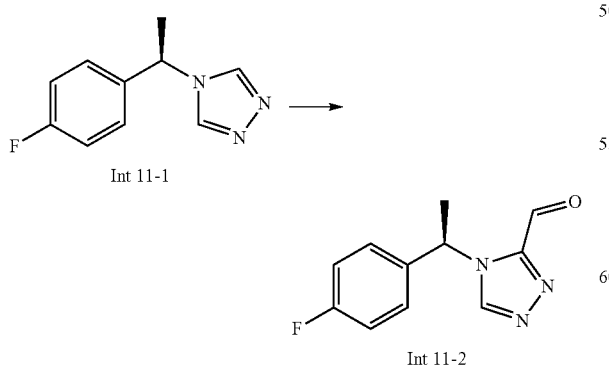

A mixture of POCl$_3$ (1.2 g, 7.85 mmol) in DMF (2 mL) was allowed to stir at 0° C. for 2 hours before compound Int 11-1 (300 mg, 1.57 mmol) in DMF (0.5 mL) was added. The reaction mixture was allowed to stir at 0° C. for another 2 hours, then allowed warmed to room temperature for about 15 hours. The reaction mixture was quenched with cold water, basified with saturated NaHCO$_3$ then extracted with EtOAc (3×10 mL). The organic layer was washed with brine, dried over sodium sulfate, filtered and in vacuo, then chromatographed on silica gel to provide 160 mg (50%) of compound Int 11-2 as a yellow oil. $^1$H NMR (CDCl3) δ 10.07 (s, 1H), 8.32 (s, 1H), 7.24-7.19 (m, 2H), 7.05-7.01 (m, 2H), 6.25 (q, J=6.8 Hz, 1H), 1.85 (d, J=6.8 Hz, 3H). MS-ESI (m/z): 220 (M+H)$^+$.

Step C—Synthesis of Int 11-3

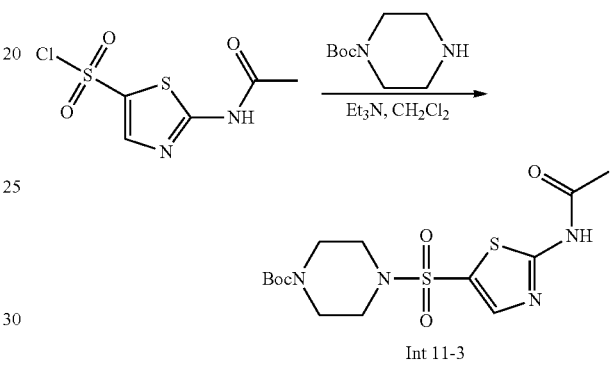

To a stirred solution of Compound 3-acetamido-5-thiazole sulfonyl chloride (21.0 g, 0.08 mol) in 200 mL of CH$_2$Cl$_2$ was added triethylamine (36.4 mL, 0.25 mol) followed by N-Boc piperazine (16.3 g, 0.08 mol) at room temperature. The mixture was allowed to stir for 2 hours until the reaction completed. The solvent was concentrated in vacuo and the resulting residue was purified using column chromatography on silica gel with petroleum ether/ethyl acetate=5:1 to provide 25 g (81%) of compound Int 11-3 as a white solid. MS (ESI) m/z (M+1): 391

Step D—Synthesis of Int 11-4

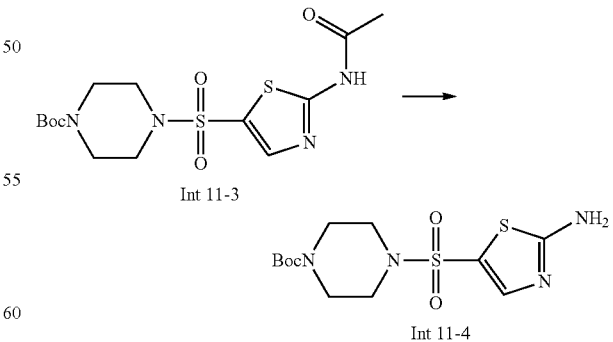

To a stirred solution of compound Int 11-3 (25 g, 0.064 mol) in 250 mL of ethanol was added 6M HCl (60 mL). The mixture was heated to 80° C. for 12 hours until the reaction completed. The reaction was cooled and concentrated in vacuo. The resulting residue was basified with sat. NaHCO₃ and treated with Boc₂O (13.9 g, 0.064 mol). The mixture was allowed to stir at room temperature for 2 hours before a white solid was formed. The mixture was filtered and the filter cake was washed with water and dried to provide 20 g of compound Int 11-4 as a white solid. ¹H-NMR (DMSO-d6) δ 7.85 (s, 2H), 3.40 (s, 4H), 2.89 (s, 4H), 2.25 (s, 3H), 1.33 (s, 9H). MS (ESI) m/z (M+1): 349

Step E—Synthesis of Int 11-5

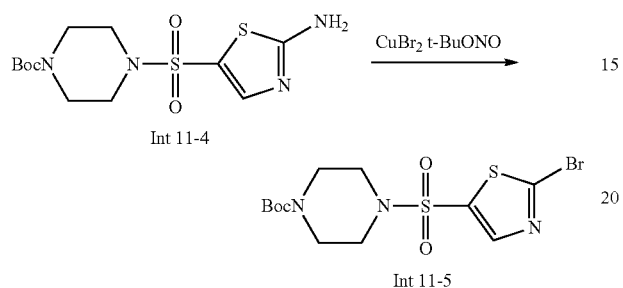

To a solution of CuBr₂ (55 g, 248 mmol) in CH₃CN (150 mL) was added t-BuONO (26 g, 248 mmol), and the mixture was then stirred at room temperature for 5 min. Compound Int 11-4 (45 g, 124 mmol) in CH₃CN (150 mL) was added dropwise to the reaction mixture in an ice bath. The mixture was then stirred at 50° C. for 0.5 hr, and then cooled to room temperature. The solution was poured into H₂O, then concentrated in vacuo ammonium hydroxide was added until the solution was clear. The aqueous layer was extracted with ethyl acetate (3×100 mL), the combined organic extracts were washed with brine, dried over Na₂SO₄ and concentrated in vacuo to provide resulting residue as green solid. The resulting residue was purified using chromatography on silical gel (petroleum ether:EtOAc=7:1) to provide 47 g (89%) of Int 11-5 as yellow solid.

Step F—Synthesis of Int 11-6

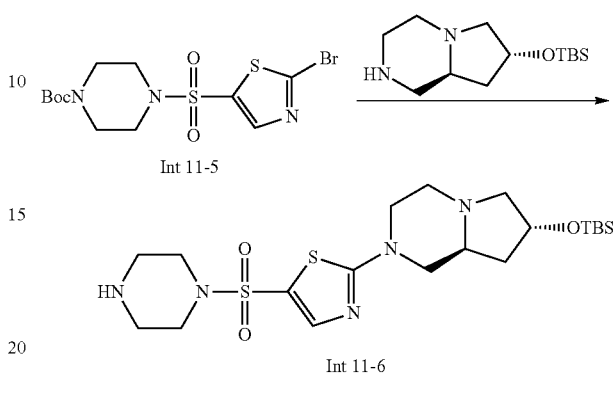

To a solution of compound Int 11-5 (2.0 g, 4.35 mmol) in MeCN (40 mL) was added K₂CO₃ (1.20 g, 8.70 mmol) and (7R,8aS)-octahydropyrrolo[1,2-a]piperazin-7-ol TBS ether. The mixture was refluxed for about 15 hours, then filtered and concentrated in vacuo. The resulting residue was purified using column chromatography on silica gel (EtOAc) to provide 2.88 g of the addition product which was dissolved 30 mL of in DCM and treated with 6 mL of TFA. The mixture was allowed to stir for 1 hour then basified with Na₂CO₃ and extracted with DCM×3. The combined organic washings were dried over Na₂SO₄ and concentrated in vacuo to provide desired compound Int 11-6 (2.2 g, 92%). MS-ESI (m/z): 488 (M+H)⁺

Step G Preparation of Compound 42

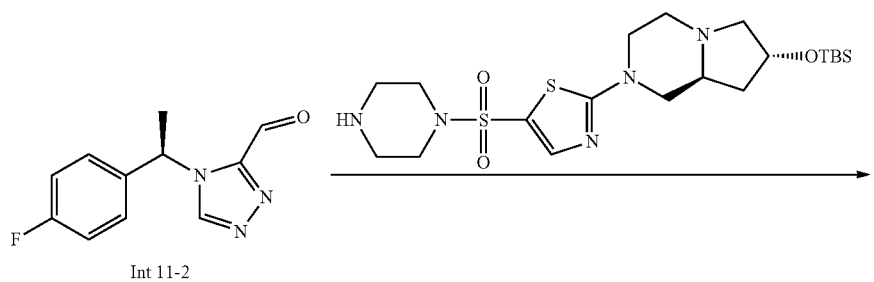

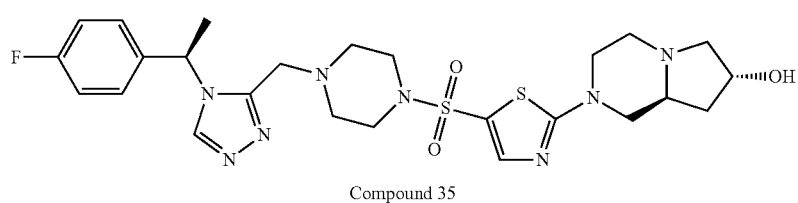

Compound 35

To a solution of compound Int 11-2 (180 mg, 0.821 mmol) in DCM (5 mL) was added compound Int 11-6 (400 mg, 0.821 mmol). The mixture was allowed to stir at room temperature for 2 hours then NaBH(OAc)$_3$ (348 mg, 1.642 mmol) was added. The mixture was allowed to stir at room temperature for another 1 hour. The reaction mixture was quenched with water and extracted with DCM (3×10 mL). The organic layer was dried over Na2SO4 and concentrated in vacuo then treated with HCl/EtOAc (5 mL) was allowed to stir at room temperature for 30 minutes and concentrated in vacuo. The crude was purified using HPLC to provide Compound 42 (31 mg, 23%). $^1$H NMR (CD$_3$OD) δ: 8.84 (s, 1H), 7.53 (s, 1H), 7.20-7.16 (m, 2H), 6.97-6.93 (m, 2H), 5.72-5.67 (q, J=6.4, 1H), 4.44-4.42 (m, 1H), 4.20-4.16 (m, 1H), 3.98-3.94 (m, 1H), 3.86-3.82 (m, 1H), 3.54-3.47 (m, 3H), 3.39-3.36 (m, 1H), 3.18-3.12 (m, 1H), 3.09-2.93 (m, 1H), 2.84 (m, 2H), 2.69-2.65 (m, 3H), 2.49-2.34 (m, 2H), 1.82-1.81 (d, J=7.2, 5H). MS-ESI (m/z): 577 (M+H)$^+$ Example 12

Preparation of Compound 43

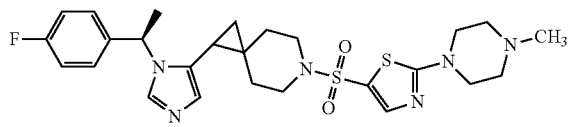

43

Step A Preparation of Int 12-1

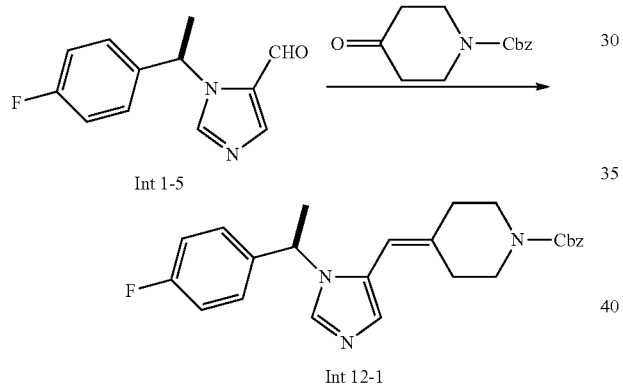

To a suspension of Zn dust (8.22 mmol) in THF (60 mL) under N$_2$ was added TiCl$_4$ (13.74 mmol) in portions via syringe slowly. The result suspension was heated to reflux for 1.5 hours. A solution of N-Cbz-piperidin-4-one (1.37 mmol) in THF (10 mL) was added to the mixture in one portion via syringe and the whole was refluxed for 15 minutes. A solution of compound Int 1-5 (1.37 mmol) in THF (10 mL) was drop wise in over 15 minutes after which the mixture was refluxed for 2 hours. The whole was cooled to and concentrated in vacuo under reduced pressure. The resulting residue was treated with water (50 mL) and aqueous ammonia (150 mL); the result suspension was then stirred at room temperature for 3 hours. The resulting mixture was filtered, and the filter cake was washed with EtOAc (3×20 mL). The filtrate was extracted with EtOAc (2×40 mL). The organics were washed with water and brine then dried over Na$_2$SO$_4$. The solvent was removed to provide resulting residue which was purified using column chromatography on silica gel [CH$_2$Cl$_2$/MeOH (60:1)] to provide desired compound Int 12-1 as a yellow oil. MS-ESI (m/z): 421 (M+H)$^+$ Step B—Synthesis of Int 12-2

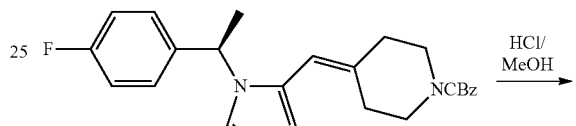

A mixture of compound Int 12-1 (420 mg, 1 mmol) in HCl/MeOH (10 mL) was allowed to stir at reflux for 2 hours then concentrated in vacuo and used in the next step without further purification. MS-ESI (m/z): 286 (M+1)$^+$ Step C—Synthesis of Int 12-3

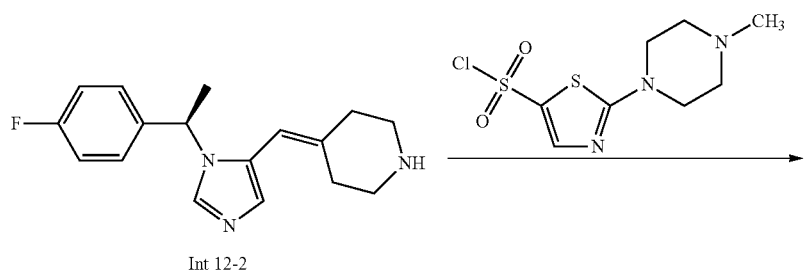

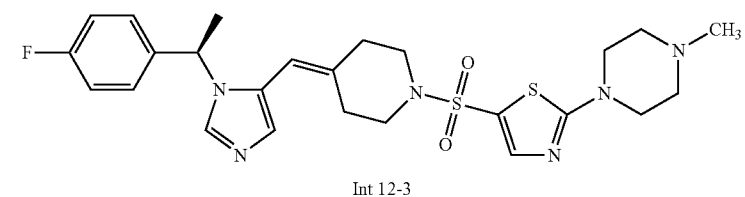

To a solution of compound Int 12-2 (285 mg, 1 mmol) and Et₃N (300 mg, 3 mmol) in DMF (5 mL) was added Int 3-8 (300 mg, 1.06 mmol) in portions. The reaction mixture was allowed to stir at room temperature for 30 min, and then extracted with EtOAc/H₂O. The organic layer was dried over MgSO₄ and concentrated in vacuo to provide the resulting residue which was chromatographed on silica gel to provide 350 mg (61%) of compound Int 12-3 as a yellow solid. $R_f$=0.5 (EtOAc:MeOH=20:1). MS-ESI (m/z): 531 (M+1)⁺.

Step D—Synthesis of Compounds 43a and 43b

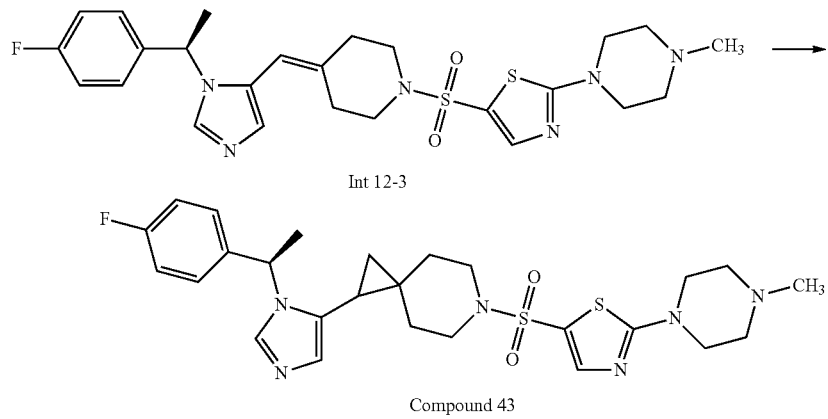

Int 12-3

Compound 43

A mixture of trimethylsulfonium iodide (670 mg, 3.28 mmol) and NaH (130 mg, 3.28 mmol) in DMSO (3 mL) was allowed to stir at 60° C. for 2 hours. Compound Int 12-3 (350 mg, 0.66 mmol) in DMSO (1 mL) was added dropwise and the reaction mixture was allowed to stir at 60° C. for 10 h, cooled to room temperature, quenched with water, and extracted with EtOAc. The organic washings were washed with brine, dried over sodium sulfate, filtered and in vacuo. The resulting residue was purified using preparative HPLC to provide Compound 43 as a mixture of 2 diastereomers (55 g of each diastereomer, 30%).

Compound 43a: ¹H NMR (CD₃OD) δ: 9.20 (s, 1H), 7.61 (s, 1H), 7.47 (s, 1H), 7.23-7.18 (m, 2H), 7.04-7.00 (m, 2H), 5.97 (d, J=7.6 Hz, 1H), 5.66 (q, J=6.8 Hz, 1H), 3.96-3.92 (m, 5H), 3.64-3.61 (m, 4H), 3.35-3.27 (m, 5H), 3.18-3.15 (m, 1H), 2.66-2.60 (m, 1H), 2.47-2.24 (m, 5H), 1.89 (d, J=6.8 Hz, 3H). MS-ESI (m/z): 545 (M+1)⁺.

Compound 43b: ¹H NMR (CD₃OD) δ: 9.19 (s, 1H), 7.58 (s, 1H), 7.46 (s, 1H), 7.20-7.17 (m, 2H), 7.02-6.98 (m, 2H), 5.97 (d, J=7.6 Hz, 1H), 5.66 (q, J=6.8 Hz, 1H), 3.96-3.78 (m, 4H), 3.64-3.61 (m, 1H), 3.36-3.27 (m, 7H), 3.18-3.16 (m, 1H), 2.95 (s, 2H), 2.66-2.19 (m, 6H), 1.89 (d, J=6.8 Hz, 3H). MS-ESI (m/z): 545 (M+1)⁺.

Example 13

Preparation of Compound 44

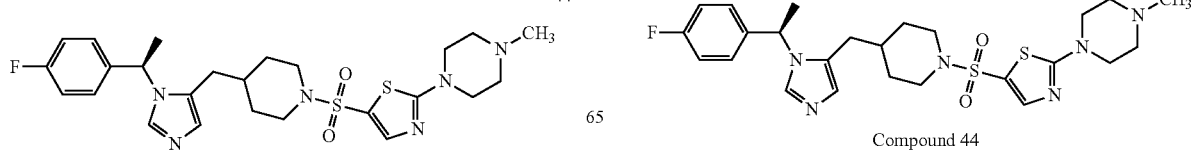

44

Step A—Synthesis of Int 12-1

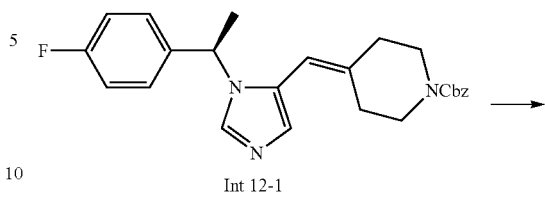

Int 12-1

-continued

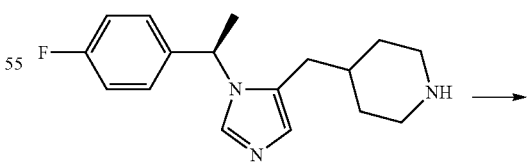

Int 13-1

To a solution of compound Int 12-1 (0.58 mmol) in methanol (30 mL) was added Pd(OH)₂ (100 mg). The result suspension was allowed to stir at room temperature under 1 atm pressure of H₂ for 3 hours. The whole was filtered through Celite and the filtrate was concentrated in vacuo to provide compound Int 13-1 as yellow oil which was used directly in the next step without further purification. MS-ESI (m/z): 288 (M+1)⁺

Step B—Synthesis of Compound 44

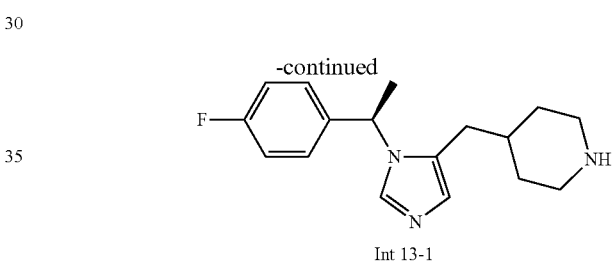

Int 13-1

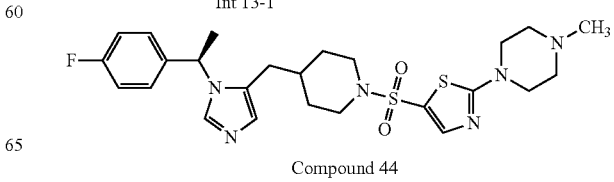

Compound 44

To a stirred solution of compound Int 13-1 (103 mg, 0.36 mmol) and Et₃N (0.72 mmol) in DMF (5 mL) was added Int 3-8 (108 mg, 0.36 mmol). The reaction mixture was allowed to stir at room temperature for 17 hours then extracted with EtOAc/H₂O. The organic layer was separated and dried over MgSO₄, filtered and concentrated in vacuo to provide the resulting residue which was chromatographed on silica gel to provide 350 mg (61%) of compound 44 as a yellow solid. ¹H NMR (CD₃OD) δ: 9.16 (s, 1H), 7.57 (s, 1H), 7.43 (d, J=12.4 Hz, 1H), 7.29~7.22 (m, 2H), 7.14 (q, J=9.6 Hz, 2H), 5.71 (q, J=6.8 Hz, 1H), 4.41~3.44 (m, 10H), 2.96 (s, 3H), 2.51 (d, J=5.6 Hz, 2H), 2.25~2.14 (m, 2H), 1.90 (d, J=7.2 Hz, 3H), 1.62 (t, J=7.6 Hz, 2H), 3.20 (d, J=12.0 Hz, 3H). MS-ESI (m/z): 533 (M+1)⁺.

Example 14

Preparation of Compound 45

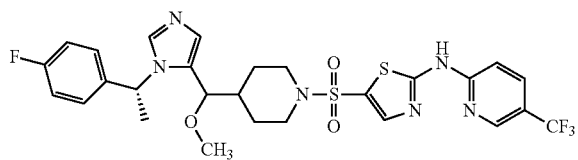

Step A Preparation of Int 14-1

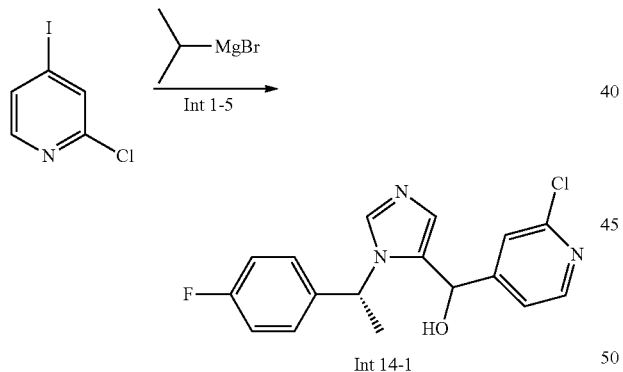

To a solution of 2-chloro-4-iodopyridine (4 g, 16.5 mmol) in anhydrous THF (40 mL) was added ⁱPrMgCl solution (2M, 10 mL) during 30 minutes at −50° C. under a N₂ atmosphere. The mixture was allowed to stir at −50° C. for 1 hour before adding Int 1-5 (3 g, 13.8 mmol) solution drop wise. Then the mixture was allowed to stir at −50° C. for 0.5 hours and at room temperature for 1 hour. The reaction mixture was quenched by saturated NH₄Cl solution (aqueous, 50 mL) and extracted with EtOAc (3×30 mL). The combined organic washings were washed with brine, dried over Na₂SO₄ and concentrated in vacuo. The crude compound Int 14-1 was used directly for the next step without further purification (4 g, 88%).

Step B Preparation of Int 14-2

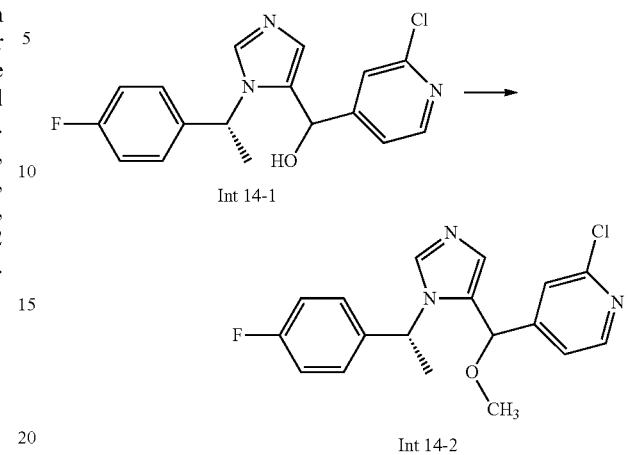

To a solution of compound Int 14-1 (2.4 g, 7.25 mmol) in anhydrous THF (30 mL) was added NaH (435 mg, 10.88 mmol) in one portion at 0° C. under a N₂ atmosphere. The mixture was allowed to stir at 0° C. for 1 hour and then the CH₃I was added dropwise at 0° C. The reaction mixture was quenched by saturated NH₄Cl solution (aqueous, 30 mL) and extracted with EtOAc (3×20 mL). The combined organic layers were washed with brine, dried over Na₂SO₄ and concentrated in vacuo. The resulting residue of compound Int 14-2 was used directly for the next step without further purification (2 g, 80%).

Step C Preparation of Int 14-3

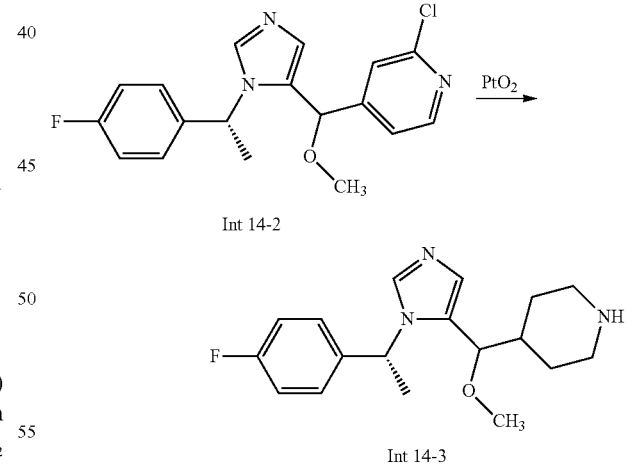

To a solution of compound Int 14-2 (1.6 g, 4.64 mmol) in a mixed solvent (HOAc/water=3:1, 40 mL) was added PtO₂ (0.6 g). The mixture was allowed to stir at room temperature for 8 hrs under H₂ atmosphere (50 psi). The mixture was filtered through Celite and concentrated in vacuo. Resulting residue Int 14-3 (1.4 g, 100%) was used directly in the next step without purification.

Step D—Synthesis of Compound 45

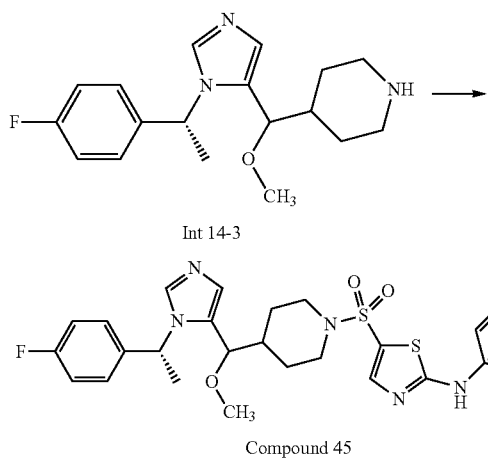

Int 14-3

Compound 45

Step A Preparation of Int 15-1

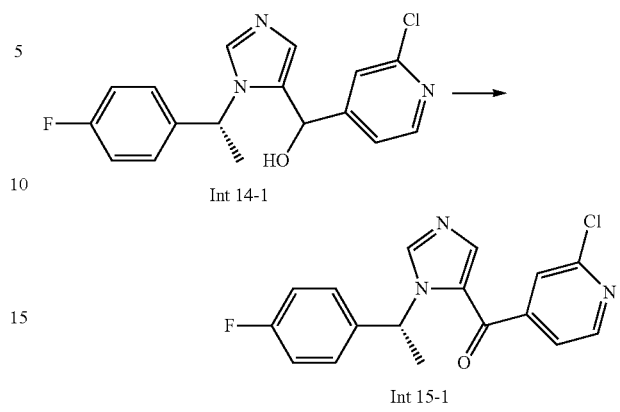

Int 14-1

Int 15-1

To a solution of compound Int 14-1 (3.01 mmol) in dioxane (30 mL) was added $MnO_2$ (30.1 mmol). The whole was heated to reflux for 3 hours. The reaction mixture was cooled, and filtered through Celite and the filtrate was concentrated in vacuo to provide compound Int 15-1 as yellow solid which was used in the next step without purification.

Step B—Synthesis of Int 15-2

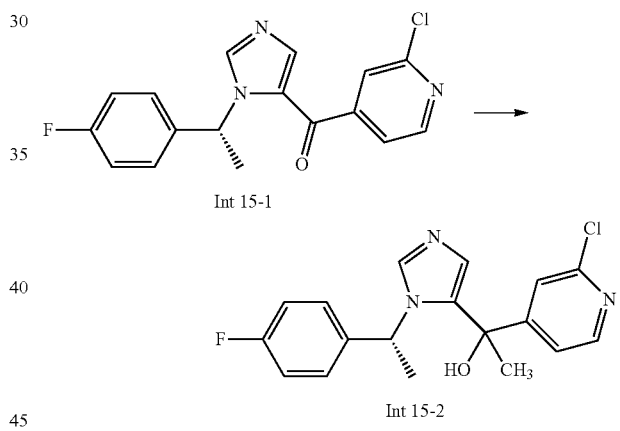

Int 15-1

Int 15-2

To a solution of compound Int 15-1 (3.03 mmol) in THF (30 mL) was cooled to 0° C. and methylmagnesium bromide (9.10 mmol, 3.0M in THF) was added drop wise. The ice bath was removed and the solution was allowed to stir to room temperature for 1 hour. The reaction mixture was cooled to 0° C., quenched with saturated $NH_4Cl$, extracted with EtOAc, then washed with brine. The organic layer was dried over $Na_2SO_4$ and concentrated in vacuo to provide compound Int 15-2.

Step C—Synthesis of Int 15-3

Int 15-2

To a solution of compound Int 14-3 (200 mg, 0.63 mmol) in DMF (3 mL) was added $Et_3N$ (0.5 mL) and 2-(5-trifluoromethylpyridin-2-ylamino)-thiazole-5-sulfonyl chloride (175 mg, 0.63 mmol). The mixture was allowed to stir for 1 hour at room temperature. The resulting residue solution of DMF was filtered and purified using preparative HPLC to provide Compound 45 (30 mg, 10%) as white solid. The two diastereomers were subsequently separated by chiral HPLC eluting with $CO_2$/MeOH.

Compound 45A: $^1$H NMR ($CD_3OD$) δ: 9.34 (s, 1H), 8.71 (s, 1H), 8.00 (d, J=8.8 Hz, 1H), 7.76 (s, 1H), 7.60 (s, 1H), 7.18-7.22 (m, 3H), 6.95-7.05 (m, 2H), 5.86 (q, J=6.6 Hz, 1H), 4.10 (d, J=6 Hz, 1H), 3.73 (d, J=11.6 Hz, 1H), 3.54 (d, J=10.4 Hz, 1H), 3.06 (s, 3H), 2.13 (t, J=11.2 Hz, 1H), 2.03 (d, J=10.8 Hz, 1H), 1.88 (d, J=7.2 Hz, 3H), 1.78 (t, J=6.4 Hz, 1H), 1.20-1.50 (m, 3H), 1.00-1.10 (m, 1H). MS-ESI (m/z): 625 $(M+1)^+$.

Compound 45B: $^1$H NMR ($CD_3OD$) δ: 9.27 (s, 1H), 8.69 (s, 1H), 8.01 (d, J=8.8 Hz, 1H), 7.78 (s, 1H), 7.57 (s, 1H), 7.25-7.30 (m, 2H), 7.15-7.20 (m, 1H), 7.00-7.10 (m, 2H), 5.85 (q, J=6.6 Hz, 1H), 4.24 (d, J=6 Hz, 1H), 3.73 (d, J=11.6 Hz, 1H), 3.64 (d, J=10.4 Hz, 1H), 3.09 (s, 3H), 2.18-2.25 (m, 2H), 1.91 (br, 1H), 1.87 (d, J=7.2 Hz, 3H), 1.20-1.50 (m, 4H). MS-ESI (m/z): 625 $(M+1)^+$.

Example 15

Preparation of Compound 46

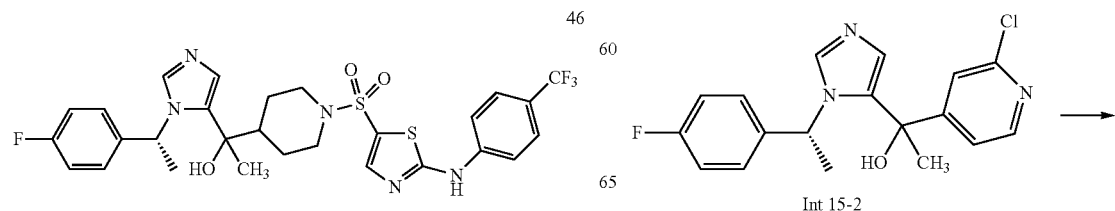

46

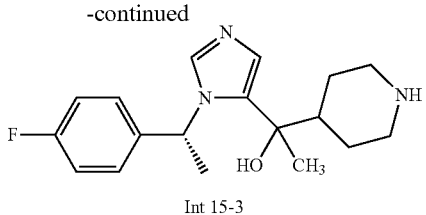

Int 15-3

To a solution of compound Int 15-2 (1.44 mmol) in 1:1 acetic acid/MeOH (10 mL) was added concentrated in vacuo HCl (imp then PtO₂ (200 mg). The mixture was charged with H₂ (50 psi) and stirred at 50° C. for 8 hours. The reaction mixture was cooled, filtered and concentrated in vacuo to provide desired compound Int 15-3 which was used directly in the next step without purification.

Step D Preparation of Compound 46

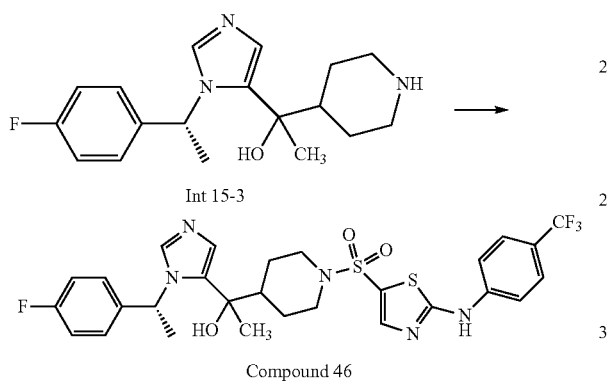

To a stirred solution of compound Int 15-3 (0.32 mmol) and Et₃N (0.64 mmol) in DMF (5 mL) was added the sulfonyl chloride (0.32 mmol). The mixture was allowed to stir at room temperature for 2 hrs. The mixture was filtered and the filtrate was purified using preparative HPLC to provide two diastereomers of Compound 46.

Compound 46A: $^1$H NMR (CD₃OD) δ: 8.71 (s, 1H), 8.49 (s, 1H), 8.03~8.01 (m, 1H), 7.78 (s, 1H), 7.30~7.19 (m, 4H), 7.01~6.94 (m, 2H), 6.44~6.42 (m, 1H), 3.71 (d, J=12 Hz, 1H), 3.67 (d, J=10.4 Hz, 1H), 2.20 (t, J=10.8 Hz, 1H), 2.18~1.75 (m, 6H), 1.67~1.44 (m, 3H). MS-ESI (m/z): 679 (M+1)⁺.

Compound 46B: $^1$H NMR (CD₃OD) δ: 9.25 (s, 0.3H), 8.89 (s, 0.6H), 8.70 (d, J=0.8 Hz, 1H), 8.02 (dd, J₁=8.8 Hz, J₂=2.0 Hz, 1H), 7.84 (s, 1H), 7.80~7.72 (m, 1H), 7.40~7.30 (m, 2H), 7.19 (d, J=8.8 Hz, 1H), 7.18~7.02 (m, 2H), 6.62~6.57 (m, 1H), 3.89 (d, J=7.6 Hz, 0.7H), 3.80~3.73 (m, 1.3H), 2.50~2.05 (m, 3H), 1.99~1.63 (m, 7H). MS-ESI (m/z): 679 (M+1)⁺.

Example 16

Preparation of Compound 47

47

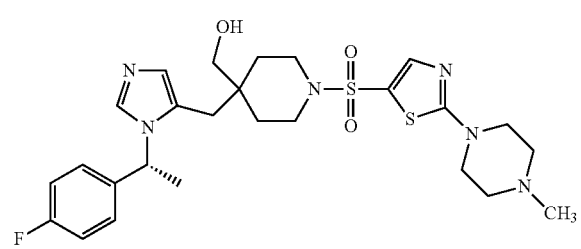

Step A—Synthesis of Int 16-1

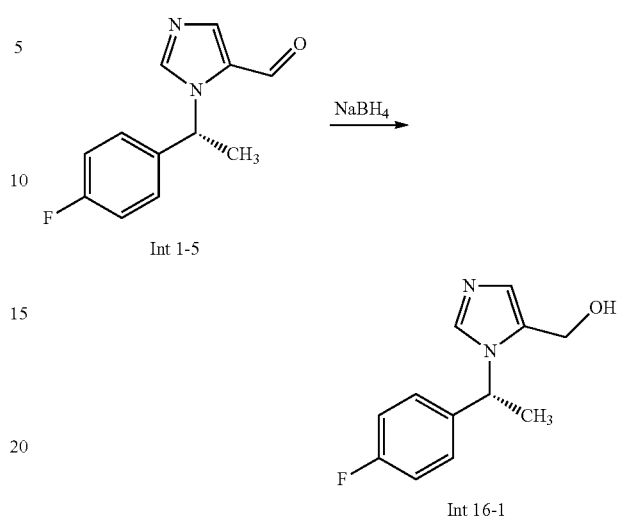

A mixture of compound Int 1-5 (5 g, 22.9 mmol) and NaBH₄ (2.6 g, 68.8 mmol) in EtOH (50 mL) was allowed to stir at room temperature for 4 hours then poured into saturated NH₄Cl. The mixture was concentrated in vacuo and extracted with EtOAc (3×20 mL). The organic layer was washed with brine, dried over MgSO₄ and concentrated in vacuo. The resulting residue was purified using flash column chromatography on silica gel eluting with 10% MeOH/EtOAc to provide compound Int 16-1 (5 g, 99%) as yellow oil. $R_f$=0.3 (EtOAc:MeOH=10:1). MS-ESI (m/z): 203 (M−17), 221 (M+1)⁺.

Step B Preparation of Int 16-2

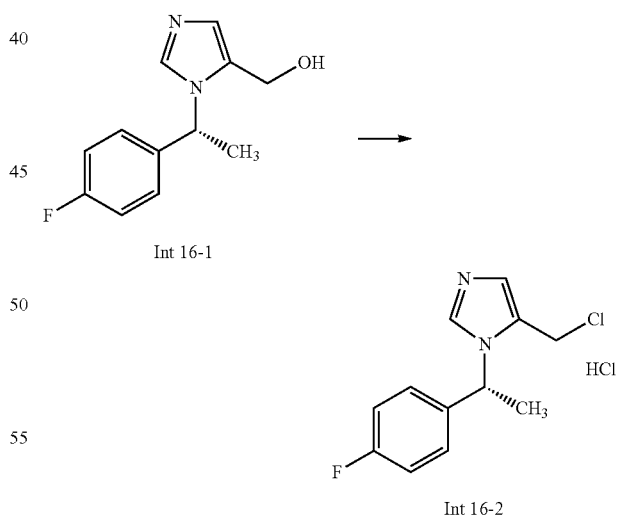

To a solution of compound Int 16-1 (5 g, 22.7 mmol) in toluene (50 mL) was added thionyl chloride (300 mg, 1.06 mmol) drop wise at room temperature. The reaction mixture was allowed to stir at 90° C. for about 15 hours. The reaction mixture was cooled and concentrated in vacuo. The resulting residue of compound Int 16-2 (5 g, 80%) was used directly without further purification. MS-ESI (m/z): 275 (M+1)⁺.

Step C Preparation of Int 16-3

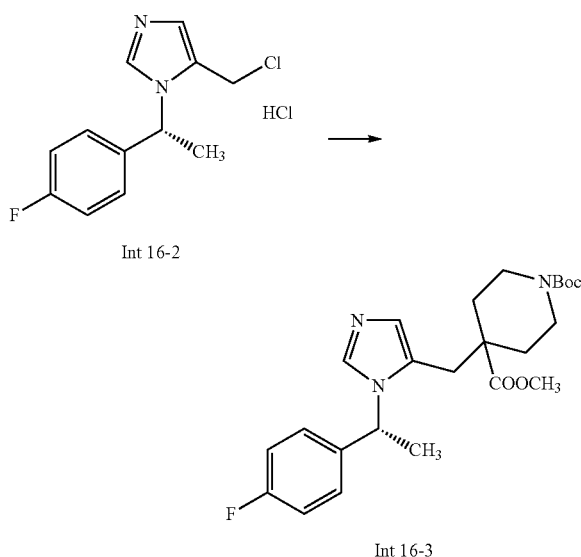

Int 16-2

Int 16-3

To a solution of compound Int 16-2 (2.5 g, 9.12 mmol) and N-Boc-piperidine-4-carboxylic acid methyl ester (2.4 g, 9.12 mmol) in anhydrous THF (50 mL) was added the LDA solution at −78° C. under $N_2$. The mixture was allowed to stir at −78° C. for 2 hours then quenched by the addition of saturated $NH_4Cl$. The resulting mixture was extracted with EtOAc (3×20 mL). The organic washings were washed with brine, dried over $MgSO_4$ and concentrated in vacuo. The resulting residue was purified using flash column chromatography on silica gel eluting with 50% petroleum ether/EtOAc to provide compound Int 16-3 as a yellow oil (1.0 g, 25%). MS-ESI (m/z): 446 (M+1)$^+$.

Step D Preparation of Int 16-4

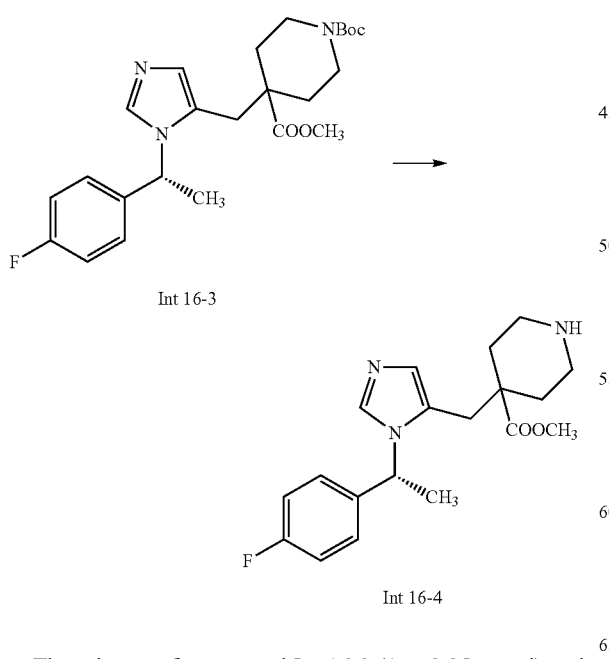

Int 16-3

Int 16-4

The mixture of compound Int 16-3 (1 g, 2.25 mmol) and TFA (20 mL) was allowed to stir at room temperature for 1 hour. The reaction mixture was concentrated in vacuo. The resulting residue of compound Int 16-4 (0.8 g, 100%) was used directly without further purification. MS-ESI (m/z): 346 (M+1)$^+$.

Step E Preparation of Int 16-5

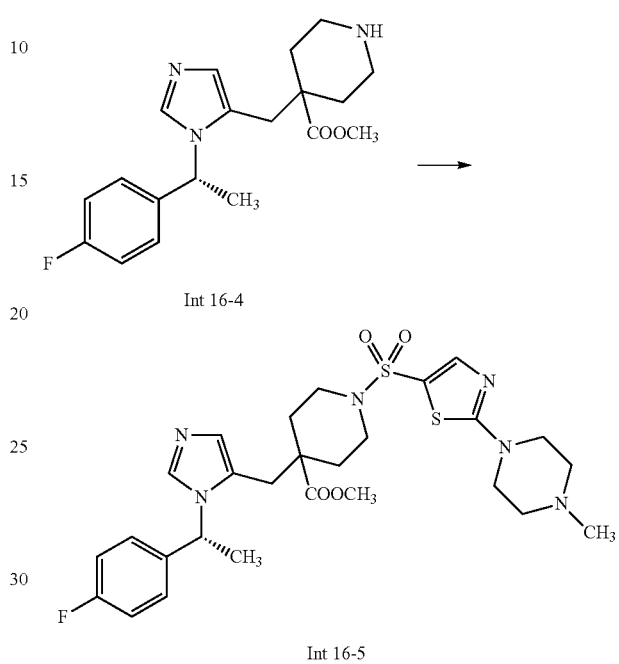

Int 16-4

Int 16-5

To a solution of compound Int 16-4 (0.8 g, 2.32 mmol) in DMF (10 mL) was added $Et_3N$ (1 mL) and Int 3-8 (0.65 g, 2.32 mmol). The mixture was allowed to stir for 1 hour at room temperature. The mixture was filtered and concentrated in vacuo. The resulting residue was purified using flash column chromatography on silica gel eluting with DCM:MeOH (10:1) to provide Int 16-5 (0.65 g, 48%) as white solid. 1H NMR (CD$_3$OD) δ 9.17 (s, 1H), 7.58 (s, 1H), 7.32 (s, 1H), 7.20-7.25 (m, 2H), 7.10-7.15 (m, 2H), 5.66 (q, J=7.6 Hz, 1H), 4.00-4.40 (br, 2H), 3.62 (s, 3H), 3.40-3.55 (m, 5H), 3.29 (s, 3H), 2.95 (s, 3H), 2.91 (s, 1H), 2.80 (d, J=8.0 Hz, 1H), 2.50-2.65 (m, 2H), 2.10-2.30 (m, 2H), 1.90 (d, J=6.8 Hz, 3H), 1.60-1.70 (m, 1H), 1.50-1.60 (m, 1H).

Step F Preparation of Compound 47

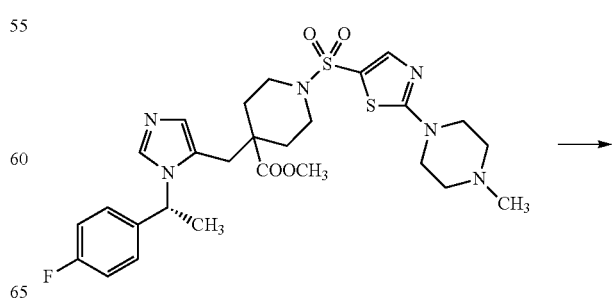

Int 16-5

-continued

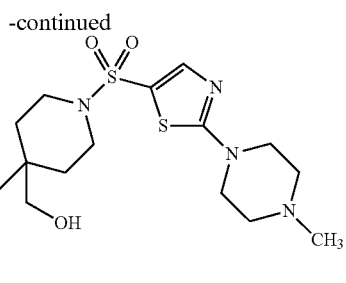

Compound 47

To a solution of Int 16-5 (650 mg, 1.10 mmol) in anhydrous THF (20 mL) was added LAH (126 mg, 3.30 mmol) in portions at 0° C. The mixture was allowed to stir at 0° C. for 2 hours, then quenched by the drop wise addition of water. The mixture was filtered and the filtrate was extracted with EtOAc (3×10 mL). The resulting residue was purified using preparative HPLC to provide Compound 47 (300 mg, 48%). $^1$H NMR (CD$_3$OD) δ: 9.10 (s, 1H), 7.60 (s, 1H), 7.43 (s, 1H), 7.20-7.30 (m, 2H), 7.10-7.15 (m, 2H), 6.06 (q, J=7.6 Hz, 1H), 4.00-4.50 (br, 2H), 3.40-3.80 (br, 4H), 3.35 (d, J=7.2 Hz, 2H), 3.26 (s, 1H), 3.19 (d, J=7.2 Hz, 2H), 2.95 (s, 3H), 2.80-2.95 (m, 2H), 2.70 (d, J=15.6 Hz, 1H), 2.55 (d, J=15.6 Hz, 1H), 1.89 (d, J=6.8 Hz, 3H), 1.70-1.80 (br, 1H), 1.50-1.65 (br, 3H). MS-ESI (m/z): 563 (M+1)$^+$.

Example 17

Preparation of Compound 48

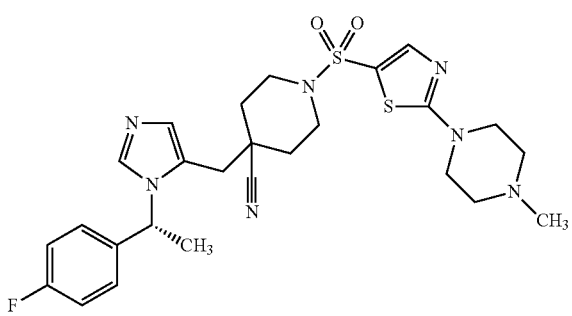

48

Step A Preparation of Int 17-1

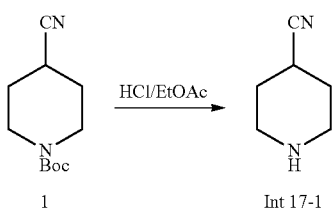 [SMILES: CC(C)(C)OC(=O)N1CCC(C#N)CC1 ; N#CC1CCNCC1]

A solution of Boc-4-cyanopiperidine (4.00 g, 19.0 mmol) in 20 mL of HCl/EtOAc (4M) was allowed to stir at room temperature for 30 min. The mixture was concentrated in vacuo to provide 2.10 g of compound Int 17-1 as a white solid. Yield: 100%. $^1$H-NMR (DMSO-d6) δ 9.32 (br, 1H), 3.18~3.08 (m, 3H), 2.97~2.92 (m, 2H), 2.08~2.04 (m, 2H), 1.95~1.85 (m, 2H).

Step B Preparation of Int 17-2

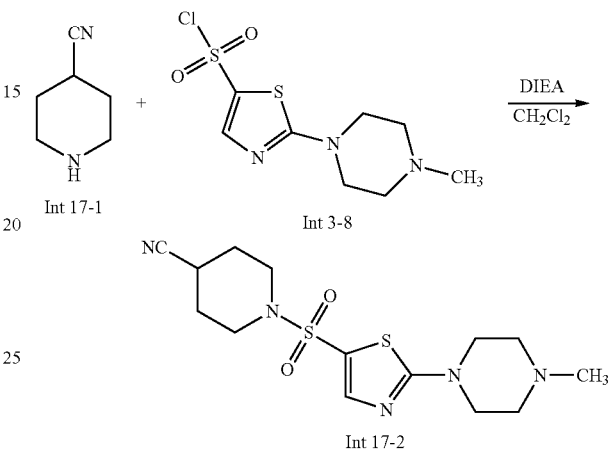

To a stirred solution of compound Int 17-1 (2.10 g, 19.0 mmol) and DIEA (4.91 g, 38.0 mmol) in 20 mL of CH$_2$Cl$_2$ was added compound Int 3-8 (8.04 g, 28.5 mmol). The mixture was allowed to stir at room temperature for 3 hours then concentrated in vacuo. The mixture was redissolved in ethyl acetate and the organic layer was washed with 2N NaOH, water, brine, dried over sodium sulfate, filtered and in vacuo. The resulting residue was recrystallized from petroleum ether/ethyl acetate=100:1 to provide 3.78 g (56%) of compound Int 17-2 as a yellow solid. $^1$H-NMR (DMSO-d6) δ 7.64 (s, 1H), 3.48~3.46 (m, 4H), 3.18~3.15 (m, 2H), 2.97~2.94 (m, 1H), 2.81~2.76 (m, 2H), 2.39~2.36 (m, 4H), 2.19 (s, 3H), 1.97~1.94 (m, 2H), 1.80~1.73 (m, 2H). MS (ESI) m/z (M+1): 356.

Step C Preparation of Compound 48

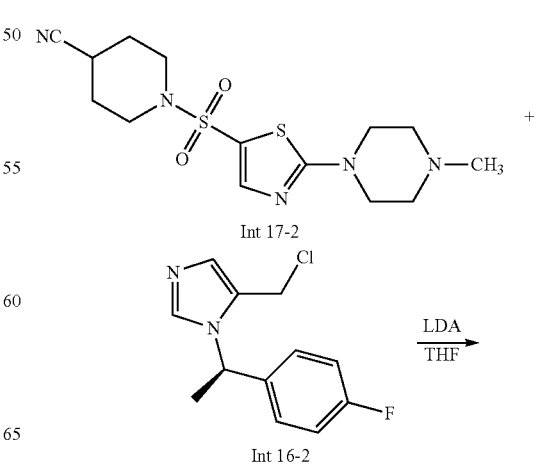

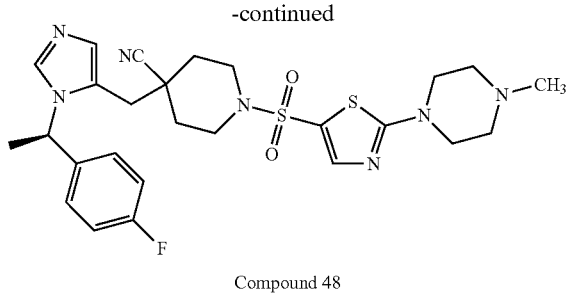

Compound 48

To a stirred solution of compound Int 17-2 (1.0 g, 2.81 mmol) and compound Int 16-2 (670 mg, 2.81 mmol) in THF (10 mL) was added LDA (5.6 mL, 5.60 mmol) at −78° C. The reaction was allowed to stir at −78° C. for 2 hours then quenched with saturated NH$_4$Cl. The aqueous layer was extracted with 3 times with ethyl acetate. The combined organic washings were washed with brine, dried over Na$_2$SO$_4$ and concentrated in vacuo to provide resulting residue as yellow oil which was purified using flash column chromatography on silica gel using ethyl acetate as the eluent to provide 235 mg of compound 48 as yellow oil. $^1$H-NMR (CD$_3$OD) δ 7.60 (s, 1H), 7.43 (s, 1H), 7.28~7.24 (m, 2H), 7.16~7.11 (m, 2H), 5.68 (q, J=6.8 Hz, 1H), 3.88~3.77 (m, 4H), 3.54~3.35 (m, 2H), 3.42~3.38 (m, 4H), 2.89 (s, 3H), 2.89~2.77 (m, 2H), 2.57~2.48 (m, 2H), 2.30~2.18 (m, 2H), 1.84 (d, J=7.2 Hz, 3H), 1.69~1.58 (m, 2H). MS (ESI) m/z (M+1): 558

Example 18

Preparation of Compound 5 pyrazin-7-ol (500 mg, 3.5 mmol). The resulting reaction was heated to reflux and allowed to stir at this temperature for 2 hours. The reaction mixture was then cooled, filtered, and concentrated in vacuo. The resulting residue was purified using HPLC to provide Compound 5 (900 mg, 45%) as a white solid. $^1$H NMR (CDCl$_3$) δ 7.71 (s, 1H), 7.57 (s, 1H), 7.26-6.90 (m, 5H), 5.52 (q, J=6.8 Hz, 1H), 4.57-4.54 (m, 1H), 4.13-4.10 (m, 1H), 3.94-3.91 (m, 1H), 3.59-3.55 (m, 1H), 3.35-3.30 (m, 2H), 3.24-3.20 (m, 1H), 3.11-3.08 (m, 1H), 2.95-2.89 (m, 5H), 2.58-2.34 (m, 5H), 2.26~2.23 (m, 1H), 1.86-1.72 (m, 2H), 1.70 (d, J=6.8 Hz, 3H). MS-ESI (ESI) m/z (M+1): 576

Example 19

Determination of IC$_{50}$ Vs CYP3A by Measurement of Inhibition of Lopinavir Metabolism This assay was performed in a standard 96-well plate design. IC$_{50}$ values were calculated from the percent inhibition observed for each test compound at 6 concentrations (for example, 0.098, 0.391, 1.56, 6.25, 25 and 100 nM). The incubation substrate mix contains 1.5 μM lopinavir, 0.01 mg/mL protein human liver microsomes (BD Gentest), 1 mM NAPDH, 3.3 mM MgCl$_2$ and 100 mM potassium phosphate buffer (pH 7.4). The production of the sum of three hydroxylated metabolites (M2: 6-hydroxy lopinavir, M3: 4-hydroxy lopinavir, M4: 4-hydroxy lopinavir (epimer of M3), Kumar et al., 1999) was determined after incubation for 8 min at 37° C. Quantitation of the metabolite peak area ratio against an internal standard (tolbutamide) was determined by LC/MS/MS analysis following acetonitrile treatment of the incubations.

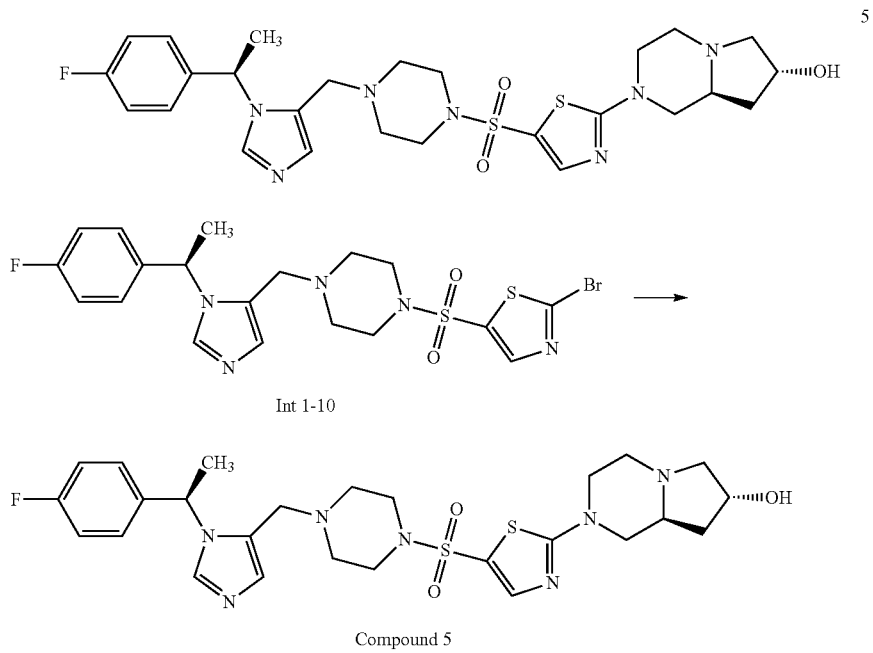

To a stirred solution of compound Int 1-10 (1800 mg, 3.5 mmol) in 10 mL of acetonitrile was added K$_2$CO$_3$ (1.5 g, 10.6 mmol) followed by (7R,8aS)-octahydropyrrolo[1,2-a]

Samples were analyzed in the MRM mode with a SCIEX API-4000 mass spectrometer (Applied Biosystems, Foster City, Calif.), with a Shimadzu LC-20 AD pump (Shimadzu corporation, Kyoto, JP) and a CTC PAL autosampler (Agilent Technologies, Switzerland). A Phenomenex, Luna, 5 µm, 100 A, 2.00×30 mm HPLC column was used for the separation. The mobile phases were: (A) 0.1% formic acid in water and (B) 0.1% formic acid in acetonitrile. The binary gradient was as follows.

| AutoSampler: CTC PAL | |
|---|---|
| Loop Volume 1 (user entered) | 100 µL |
| Loop Volume 2 (user entered) | 100 µL |
| Actual Injection Volume | 10.0 µL |

| Binary Gradient Total Flow: 700 µL/min | | |
|---|---|---|
| Time (min) | A (%) | B (%) |
| 0.01 | 95 | 5 |
| 0.50 | 2 | 98 |
| 0.70 | 2 | 98 |
| 0.71 | 95 | 5 |
| 1.00 | System Controller | Stop |

The mass spectrum parameters were as follows:

| MS Parameters: | |
|---|---|
| CUR Curtain gas (psi): | 20 |
| GS1 Ion source gas1 (psi): | 55 |
| GS2 Ion source gas2 (psi): | 60 |
| IS IonSpray voltage (V): | 5500 |
| TEM Temperature (° C.): | 600 |
| ihe Interface heater (on/off): | ON |
| CAD Collision Activated Dissociation (psi): | 10 |
| EP Entrance Potential (V): | 10 |
| CXP Collision Cell Exit Potential (V): | 12 |

The LC/MS/MS parameters for the analytes were as follows.

| LC/MS/MS Analysis | | | | | |
|---|---|---|---|---|---|
| | Ion Transition | | DP | CE | RT Retention |
| Compound | Q1 Mass (m/z) | Q3 Mass (m/z) | Declustering Potential (V) | Collision Energy (V) | Time (min) |
| M2-4 | 645.2 | 447.2 | 30 | 25 | 0.51 |
| Lopinavir | 629.2 | 183.1 | 80 | 63 | 0.56 |
| IS (Tolbutamide) | 271.1 | 155.3 | 52 | 25 | 0.49 |

The peak area ratio of the analyte to the internal standard was used to quantify the metabolite. The values of peak area ratios in the presence of test compound were compared to those of maximum or minimum controls and were expressed as % inhibition by interpolating between the maximum and minimum peak area ratios. Incubations with no inhibitor were defined as the maxima and with 5 µM ketoconazole were defined as the minima.

The following equation was used to calculate the % inhibition:

$$[1-[(X-\text{Low control})/(\text{High control}-\text{Low control})]]*100$$

For the $IC_{50}$ calculation, SigmaPlot was used to plot the mean % inhibition versus the test compound concentrations and for non-linear regression analysis of the data. Depending on the range of data points defining the inhibition curve, the data may have been fit to the 4-parameter logistic equation.

Example 20

Determination of $IC_{50}$ in a Cocktail Assay for CYPs 1A2, 2C9, 2C19, 2D6 and 3A4

This assay was performed in a standard 96-well plate design. $IC_{50}$ values were calculated from the percent inhibition observed for each test compound at 6 concentrations (for example, 0.0032, 0.016, 0.08, 0.4, 2 and 10 µM). The incubation substrate mix contains 10 µM phenacetin (1A2), 5 µM diclofenac (2C9), 30 µM mephenytoin (2C19), 5 µM dextromethorphan (2D6) and 2 µM midazolam (3A4), 0.1 mg/mL protein human liver microsomes (BD Gentest), 1 mM NAPDH, 3.3 mM $MgCl_2$ and 100 mM potassium phosphate buffer (pH 7.4). The production of the metabolite of each probe substrate was determined after incubation for 10 min at 37° C. Quantitation of the metabolite peak area ratio against an internal standard (tolbutamide) was determined by LC/MS/MS analysis following acetonitrile treatment of the incubations.

| Probe Substrate | Reaction (isoform) | Metabolite Detected |
|---|---|---|
| Phenacetin | O-deethylation (CYP1A2) | Acetaminophen |
| Diclofenac | 4'-hydroxylation (CYP2C9) | 4'-Hydroxydiclofenac |
| Mephenytoin | 4'-hydroxylation (CYP2C19) | 4'-Hydroxymephenytoin |
| Dextromethorphan | O-demethylation (CYP2D6) | Dextrorphan |
| Midazolam | 1'-hydroxylation (CYP3A4) | 1'-Hydroxymidazolam |

Samples were analyzed in the MRM mode with a SCIEX API-4000 mass spectrometer (Applied Biosystems, Foster City, Calif.), with a Shimadzu LC-20 AD pump (Shimadzu corporation, Kyoto, JP) and a CTC PAL autosampler (Agilent Technologies, Switzerland). A Phenomenex, Luna, 5 µm, 100 A, 2.00×30 mm HPLC column was used for the separation. The mobile phases were: (A) 0.1% formic acid in water and (B) 0.1% formic acid in acetonitrile. The binary gradient was as follows.

| AutoSampler: CTC PAL | |
|---|---|
| Loop Volume 1 (user entered) | 100 µL |
| Loop Volume 2 (user entered) | 100 µL |
| Actual Injection Volume | 10.0 µL |

| Binary Gradient Total Flow: 700 µL/min | | |
|---|---|---|
| Time (min) | A (%) | B (%) |
| 0.01 | 98 | 2 |
| 0.40 | 30 | 70 |
| 0.80 | 2 | 98 |
| 1.00 | System Controller | Stop |

The mass spectrum parameters were as follows:

| MS Parameters: | |
|---|---|
| CUR Curtain gas (psi): | 20 |
| GS1 Ion source gas1 (psi): | 50 |
| GS2 Ion source gas2 (psi): | 60 |

| MS Parameters: | |
| --- | --- |
| IS IonSpray voltage (V): | 5500 |
| TEM Temperature (° C.): | 600 |
| ihe Interface heater (on/off): | ON |
| CAD Collision Activated Dissociation (psi): | 10 |
| EP Entrance Potential (V): | 10 |
| CXP Collision Cell Exit Potential (V) | 12 |

The LC/MS/MS parameters for the analytes were as follows.

| | LC/MS/MS Analysis | | | | |
| --- | --- | --- | --- | --- | --- |
| | Ion Transition | | DP | CE | RT |
| Compound | Q1 Mass (m/z) | Q3 Mass (m/z) | Declustering Potential (V) | Collission Energy (V) | Retention Time (min) |
| Acetominophen | 152.2 | 110 | 40 | 23 | 0.36 |
| 4'-Hydroxydiclofenac | 312 | 231 | 32 | 29 | 0.72 |
| 4'-Hydroxymephenytoin | 235.3 | 150.3 | 45 | 25 | 0.49 |
| Dextrorphan | 258.2 | 157.2 | 40 | 55 | 0.42 |
| 1'-hydroxymidazolam | 342.2 | 203.2 | 40 | 30 | 0.53 |
| IS | 271.1 | 155.3 | 69 | 25 | 0.71 |

The peak area ratio of the analyte to the internal standard was used to quantify the metabolite. The values of peak area ratios in the presence of test compound were compared to those of maximum or minimum controls and were expressed as % inhibition by interpolating between the maximum and minimum peak area ratios. Incubations with no inhibitor were defined as the maxima.

The following equation was used to calculate the % inhibition:

[1−[(X−Low control)/(High control−Low control)]]
*100

For the $IC_{50}$ calculation, SigmaPlot was used to plot the mean % inhibition versus the test compound concentrations and for non-linear regression analysis of the data. Depending on the range of data points defining the inhibition curve, the data may have been fit to the 4-parameter logistic equation.

Example 21

Determination of $IC_{50}$ Vs CYP11B1/CYP11B2 by Measurement of Cortisol/Aldosterone Synthesis This assay was performed in a standard 384-well plate design using cultured V79 cells stably expressing human CYP11B1 or human CYP11B2. Test compounds at 10 concentrations (for example, 10000, 3333.3, 1111.1, 370.4, 123.5, 41.2, 13.7, 4.6, 1.5 and 0.5 nM) were added in 384-well plate after the cell-seeding procedure. The incubation substrate contains 1500 nM RSS for CYP11B1 assay/750 nM DOC for CYP11B2 assay. The Cortisol/Aldosterone production of cell culture supernatant was determined by Cortisol/Aldosterone HTRF kit after for about 15 hours incubation at RT (protect from light). IC50 values were calculated from the percent inhibition observed for each test compound at 10 concentrations.

The assay plate was read using Envision (Perkin Elmer, Waltham, Mass.) at 665 nm and 590 nm (using Filter Barcode of 217#, 205#; Mirror Barcode of 446#).

The Envision setting parameters were as follows:

| Envision Parameters: | |
| --- | --- |
| Light source: | Laser |
| Top mirror (Barcode): | 446# |
| Bottom mirror (Barcode): | None |
| Emission Filter (Barcode): | 217# |
| $2^{nd}$ emission Filter (Barcode): | 205# |
| Measurement height (mm): | 6.5 |
| Delay (μs): | 50 |

| -continued | |
| --- | --- |
| Envision Parameters: | |
| Window time (μs): | 400 |
| Number of sequential windows: | 1 |
| Time between flashes | 16600 |
| Number of flashes | 10 |
| Number of flashes for $2^{nd}$ detector | 10 |

Data are analyzed using Assay Data Analyzer. All ratio data (665 nm/590 nm) are back calculated according to the standard curve, resulting in Cortisol/Aldosterone concentrations. IC50 values are reported as the Inflection Point (IP) of a four parameter fit of the titration data.

The following equation was used to calculate the % inhibition:

% Activity=100×{1−(Sample_back calculated Cortisol/Aldosterone concentration−LC_back calculated Cortisol/Aldosterone concentration)/(HC_back calculated Cortisol/Aldosterone concentration−LC_back calculated Cortisol/Aldosterone concentration)}

Curve Fitting: Four Parameter Logistic:

$$y = n + \frac{m-n}{1+\left(\frac{i}{x}\right)^p}$$

Example 22

The table below provides data for compounds of Formula (I) obtained using the assays described in Examples 18 and 19, above.

| Cmpd No. | 3A4(LPV) | CYP1A2 | CYP2C9 | CYP2C19 | CYP2D6 | CYP11B1 | CYP11B2 |
|---|---|---|---|---|---|---|---|
| 1 | 1.4 | >10000 | 2299 | 2534 | 2782 | 1765 | 1716 |
| 2 | 1 | >10000 | 3219 | 1829 | 8011 | 215 | 77 |
| 3 | 2.7 | >10000 | 1470 | >10000 | 2700 | >10000 | >10000 |
| 4 | <0.1 | >10000 | 1843 | 721 | 5248 | 225 | 445 |
| 5 | 3.8 | >10000 | 4460 | 3853 | >10000 | 2004 | 4771 |
| 6 | 1.4 | >10000 | 1937 | >10000 | >10000 | 1558 | 3878 |
| 7 | 1.7 | >10000 | 3393 | >10000 | >10000 | 4089 | 16330 |
| 8 | 1.8 | >10000 | 3497 | >10000 | >10000 | >10000 | 4005 |
| 9 | 2.8 | >10000 | 4118 | >10000 | >10000 | 2045 | 3922 |
| 10 | <0.98 | >10000 | 2684 | >10000 | >10000 | 1913 | >10000 |
| 11 | <0.98 | >10000 | 2148 | 8018 | >10000 | 1105 | 3394 |
| 12 | 1.0 | >10000 | 1748 | >10000 | 2851 | 1464 | 1694 |
| 13 | 1.4 | >10000 | 7407 | >10000 | 9618 | 1561 | 8584 |
| 14 | 1.4 | >10000 | 9759 | >10000 | 1539 | 1055 | 1152 |
| 15 | 1.2 | >10000 | 2461 | >10000 | 3562 | 1708 | 3625 |
| 16 | 5.2 | 1495 | 9121 | 8038 | >10000 | >10000 | 4601 |
| 17 | 1.7 | 2186 | 2450 | 2254 | 3382 | >10000 | 9354 |
| 18 | 1.1 | >10000 | 2295 | 2164 | 5003 | 2594 | 4584 |
| 19 | 1.7 | >10000 | 1412 | 7953 | 7009 | 1850 | 1927 |
| 20 | 4.1 | 2769 | 4500 | 4109 | >10000 | 1015 | 2236 |
| 21 | 1.9 | >10000 | 1158 | 10000 | 6176 | 3918 | >10000 |
| 22 | 1.3 | 8657 | 5695 | 2291 | 3655 | 1162 | 1353 |
| 23 | 1.6 | >10000 | 5009 | >10000 | 4650 | 1221 | 4573 |
| 24 | 1.9 | >10000 | 1352 | >10000 | 3199 | 4265 | >10000 |
| 25 | 1.9 | >10000 | 9728 | >10000 | 8349 | 6929 | >10000 |
| 26 | 1.5 | >10000 | 4274 | 7209 | >10000 | 3041 | 9224 |
| 27 | 2.6 | >10000 | 1766 | 6478 | 3848 | 1575 | 2269 |
| 28 | 4.4 | >10000 | 6612 | 3682 | 6495 | 3553 | 4643 |
| 29 | 2.9 | >10000 | >10000 | >10000 | >10000 | 1442 | 4366 |
| 30 | 3.6 | >10000 | >10000 | >10000 | 4920 | 4515 | 2903 |
| 31 | 4.4 | >10000 | >10000 | >10000 | >10000 | >10000 | >10000 |
| 32 | 1.2 | >10000 | 1560 | 3444 | 1298 | 1579 | 1029 |
| 33 | 2.3 | >10000 | >10000 | 7515 | 4803 | 4750 | 1605 |
| 34 | 1.0 | >10000 | 2951 | >10000 | >10000 | 1032 | 2979 |
| 35 | 3.8 | >10000 | >10000 | >10000 | 8893 | 2184 | 4998 |
| 36 | 4.3 | >10000 | >10000 | >10000 | 4077 | 1350 | 3834 |
| 37 | 4.1 | 5808 | 6102 | >10000 | >10000 | 3815 | 193 |
| 38 | 2.5 | >10000 | 1220 | 4185 | 7130 | 2137 | 1309 |
| 39 | 8.0 | 3730 | 4700 | 2650 | 2180 | 2475 | 2466 |
| 40 | 0.8 | >10000 | 357 | 3045 | 2888 | 1148 | 3900 |
| 41 | 2.1 | >10000 | 2256 | 4949 | 2298 | nd | nd |
| 42 | 32 | >10000 | >10000 | >10000 | >10000 | 7800 | >10000 |
| 43a | 6.0 | >10000 | >10000 | >10000 | 2900 | nd | nd |
| 43b | 2.0 | >10000 | >10000 | 9200 | 3600 | nd | nd |
| 44 | 1.1 | >10000 | 3565 | 8386 | 2408 | nd | nd |
| 45a | <0.98 | >10000 | 336 | 1132 | 5684 | nd | nd |
| 45b | <0.98 | >10000 | 1452 | 4494 | 7854 | nd | nd |
| 46a | <0.98 | >10000 | >10000 | >10000 | >10000 | nd | nd |
| 46b | <0.98 | >10000 | >10000 | >10000 | >10000 | nd | nd |
| 47 | 13 | >10000 | >10000 | >10000 | 5844 | nd | nd |
| 48 | 9.4 | >10000 | >10000 | 8065 | 2846 | nd | nd | nd = no data

Example 24

In Vivo Effects of the Compounds of the Invention on the Pharmacokinetics of a Therapeutic Compound Metabolized by CYP3A4 in Sprague-Dawley Rats The ability of the compounds of the present invention to enhance the exposure of two known HIV protease inhibitors that are metabolized by CYP3A4, Lopinavir (LPV) and Atazanavir (ATV), was evaluated in rats. Fasted male Sprague-Dawley rats were co-dosed with 10 mg/kg PO dose of a compound of Formula (I) and 10 mg/kg of either LPV or ATV. The mean AUC values are listed in the Table below and are compared to dosing with and without the PKE.

| Compound of Formula (I) | LPV $AUC_{0-inf}$ (uM*h) | Ratio (+/−) PKE | ATV $AUC_{0-inf}$ (uM*h) | Ratio (+/−) PKE |
|---|---|---|---|---|
| none | 2.2 | n/a | 1.2 | n/a |
| 2 | 22 | 10 | 3.4 | 2.8 |
| 4 | 14.3 | 6.5 | 2.4 | 2 |
| 5 | 26 | 11.8 | 2.4 | 2 |
| 44 | 14.2 | 6.5 | — | — |

Co-administration of compounds 2, 4, 5 or 44 resulted in an increase in mean LPV exposure of 6-10×. The mean increase in exposure when these compounds were co-dosed with ATV was 2-2.8×. These results show that the compounds of the present invention are efficient and potent enhancer of the pharmacokinetics of both Lopinavir and Atazanavir in vivo.

Example 25

In Vivo Effects of the Compounds of the Present Invention on the Pharmacokinetics of Therapeutic Compound Metabolized by CYP3A4 in Male Cynomolgus Monkeys The ability of the compounds of the present invention to enhance the exposure of two different marketed HIV protease inhibitors, Lopinavir (LPV) and Atazanavir (ATV), was evaluated in non-human primates. Fasted male cynomolgus monkeys were co-dosed with 3 mg/kg PO dose of selected compounds of Formula (I) and 3 mg/kg of either LPV or ATV. The mean AUC values are listed in the Table below.

| Compound of Formula (I) | LPV $AUC_{0-inf}$ (uM*h) | Ratio (+/−) PKE | ATV $AUC_{0-inf}$ (uM*h) | Ratio (+/−) PKE |
|---|---|---|---|---|
| none | 0.01 | n/a | 0.005 | n/a |
| 2 | 12.2 | 1220 | 1.0 | 200 |
| 4 | 7.9 | 790 | 1.9 | 380 |
| 5 | 6.2 | 620 | 2.4 | 480 |
| 44 | 5.6 | 560 | nd | nd |

Co-administration of compounds 2, 4, 5 or 44 resulted in an increase in mean LPV exposure of 620-1220×. The mean increase in exposure when these compounds were co-dosed with ATV was 200-480×. These results show that the compounds of the present invention are efficient and potent enhancers of the pharmacokinetics of both Lopinavir and Atazanavir in cynomolgus monkeys.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula (I):

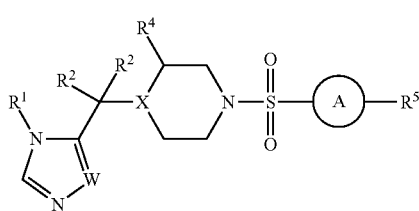

(I)

or a pharmaceutically acceptable salt thereof, wherein:
A is a 5 or 6-membered heteroarylene group;
W is N or —CH—;
X is N or —C($R^3$)—;
$R^1$ is selected from —($C_1$-$C_6$ alkylene)-aryl, —($C_1$-$C_6$ alkylene)-(5 or 6-membered heteroaryl), —($C_1$-$C_6$ alkylene)-O-aryl, —($C_1$-$C_6$ alkylene)-O-(5 or 6-membered heteroaryl) and $C_3$-$C_6$ cycloalkyl, wherein any aryl, heteroaryl or $C_3$-$C_6$ cycloalkyl group can be optionally substituted with up to four $R^7$ groups, which can be the same or different, and wherein said $C_3$-$C_6$ cycloalkyl group can be fused to a benzene ring and said fused benzene ring can be optionally substituted with up to four $R^7$ groups, which can be the same or different;
each occurrence of $R^2$ is independently selected from H, $C_1$-$C_6$ alkyl, —OH, —O—($C_1$-$C_6$ alkyl) and —($C_1$-$C_6$ alkylene)-O—($C_1$-$C_6$ alkyl);
$R^3$ is selected from H, $C_1$-$C_6$ alkyl, $C_1$-$C_6$ hydroxyalkyl and —CN, or $R^3$ and an $R^2$ group, together with the carbon atoms to which they are attached, can combine to form a cyclopropyl ring;
$R^4$ is H, or $R^4$ and an $R^2$ group, can join to form a group selected from —$CH_2$—$CH_2$—$CH_2$—, —C(O)—O—$CH_2$—, —$CH_2$—O—$CH_2$— and —$CH_2$—N($R^8$)—$CH_2$—;
$R^5$ is —NH($R^6$), 5 or 6-membered monocyclic heterocycloalkyl or 9 or 10-membered bicyclic heterocycloalkyl, wherein said 5 or 6-membered monocyclic heterocycloalkyl group can optionally form a spirocycle with a $C_3$-$C_6$ cycloalkyl group or another 5 or 6-membered monocyclic heterocycloalkyl group, and wherein said 5 or 6-membered monocyclic heterocycloalkyl group and said 9 or 10-membered bicyclic heterocycloalkyl group can be optionally substituted on one or more ring carbon atoms with up to four $R^7$ groups, which can be the same or different, and wherein a ring carbon atom of a 5 or 6-membered monocyclic heterocycloalkyl group may be functionalized as a carbonyl group
$R^6$ is $C_1$-$C_6$ alkyl or 5 or 6-membered heteroaryl, wherein said $C_1$-$C_6$ alkyl group is optionally substituted with 1 or 2 groups, each independently being $NH_2$ or halo, and wherein said 5 or 6-membered heteroaryl group can be optionally substituted with up to four $R^7$ groups;
each occurrence of $R^7$ is independently selected from $C_1$-$C_6$ alkyl, 5 or 6-membered heterocycloalkyl, $C_1$-$C_6$ hydroxyalkyl, $C_1$-$C_6$ haloalkyl, halo, —CN, —N($R^8$)$_2$, —$CH_2$N($R^8$)$_2$, —$OR^8$, —C(O)$OR^8$, —$SR^8$, —S(O)$_2R^8$ and —C(O)N($R^8$)$_2$, wherein said 5 or 6-membered heterocycloalkyl group can be optionally substituted with a group selected from $C_1$-$C_6$ alkyl, halo, $C_1$-$C_6$ hydroxyalkyl, $C_1$-$C_6$ haloalkyl, halo, —CN, —N($R^8$)$_2$ and —$OR^8$; and
each occurrence of $R^8$ is independently H or $C_1$-$C_6$ alkyl.

2. The compound of claim 1, wherein A is thiazolyl, pyridyl or pyrazinyl.

3. The compound of claim 1, having the formula (Ia):

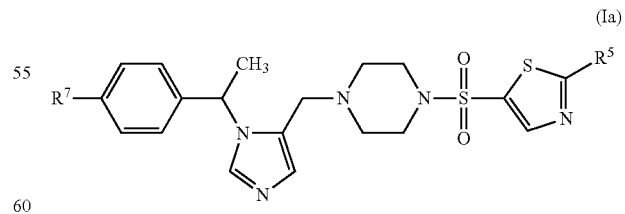

(Ia)

or a pharmaceutically acceptable salt thereof, wherein:
$R^5$ is 5 or 6-membered monocyclic heterocycloalkyl, 9 or 10-membered bicyclic heterocycloalkyl, wherein said 5 or 6-membered monocyclic heterocycloalkyl group can optionally form a spirocycle with a $C_3$-$C_6$ cycloalkyl group or another 5 or 6-membered monocyclic heterocycloalkyl group, and wherein said 5 or 6-membered monocyclic heterocycloalkyl group, said 9 or 10-membered bicyclic heterocycloalkyl and said spirocycle can be optionally substituted on one ring carbon atom with $C_1$-$C_6$ alkyl or halo; and each occurrence of $R^7$ is independently selected from H, $C_1$-$C_6$ alkyl or halo.

4. The compound of claim 1, wherein $R^5$ is 5 or 6-membered monocyclic heterocycloalkyl, which can optionally form a spirocycle and/or be optionally substituted as described in claim 1.

5. The compound of claim 1, wherein $R^5$ is 9 or 10-membered bicyclic heterocycloalkyl, which can be optionally substituted as described in claim 1.

6. The compound of claim 1, wherein $R^5$ is selected from:

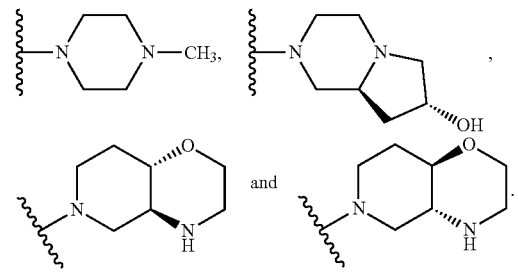

7. The compound of claim 3, wherein $R^7$ is halo.
8. The compound of claim 7, wherein $R^7$ is F.
9. The compound of claim 1, having the structure:

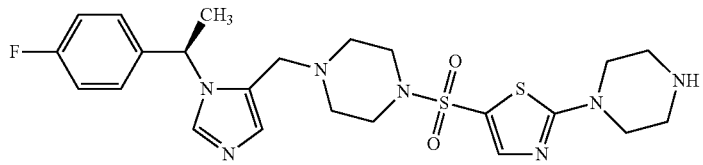

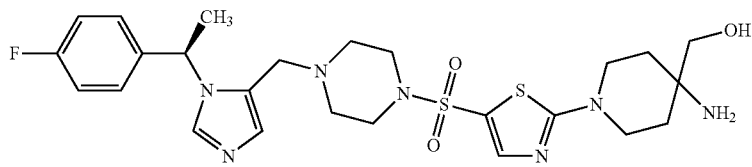

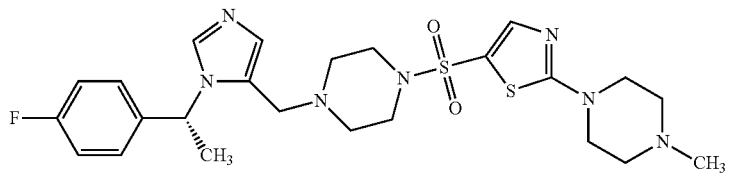

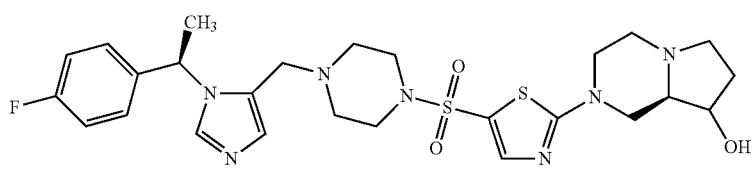

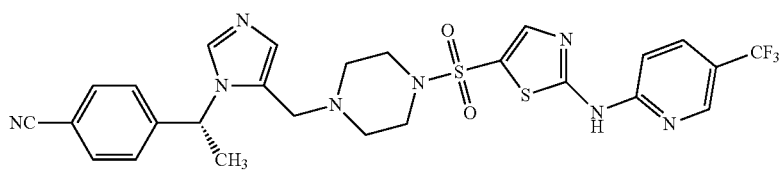

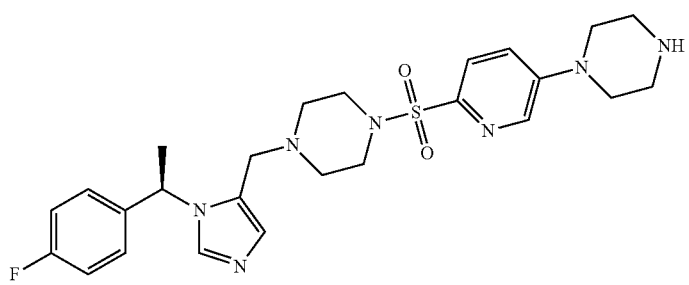

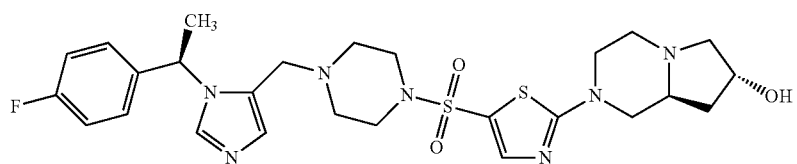
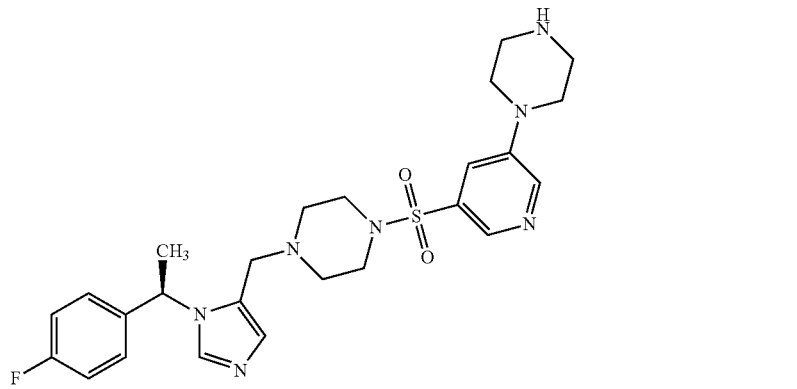
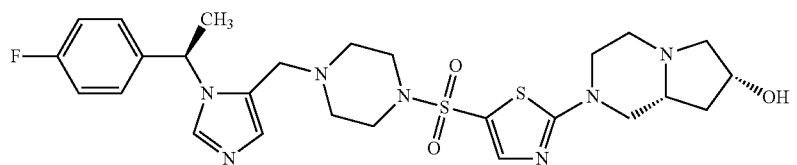
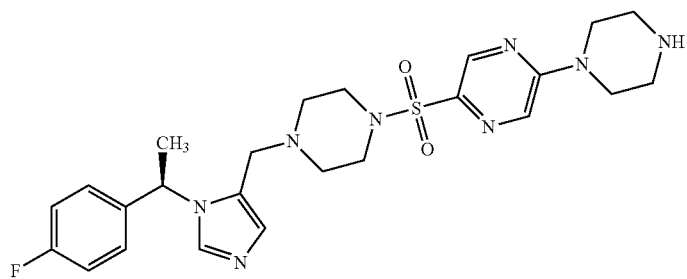
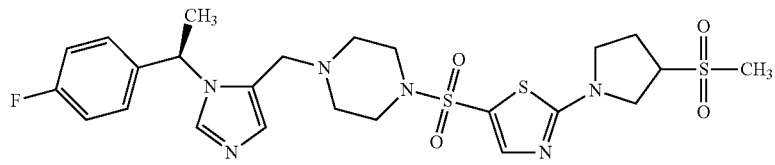
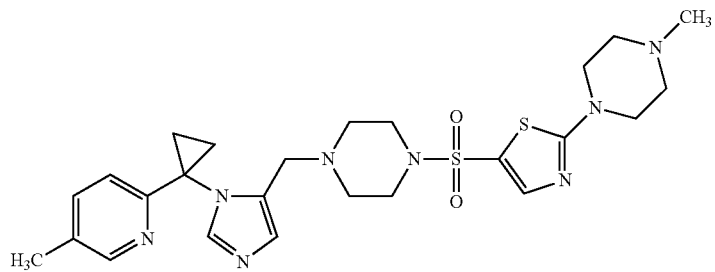
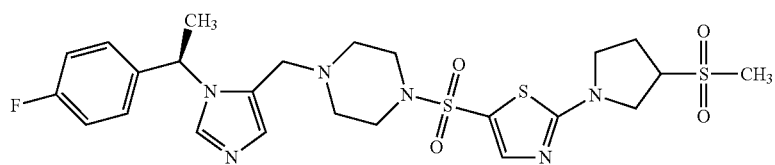

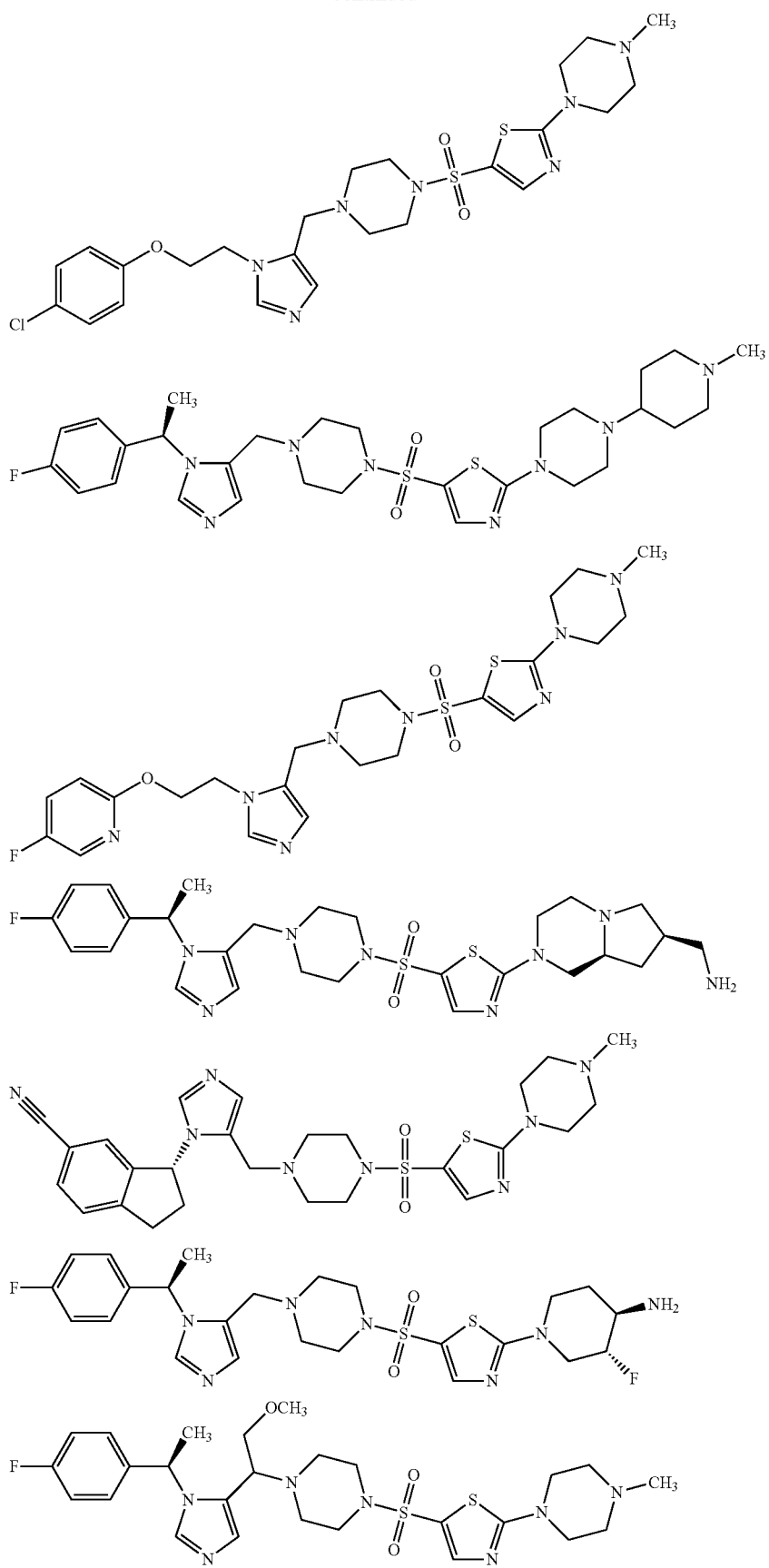

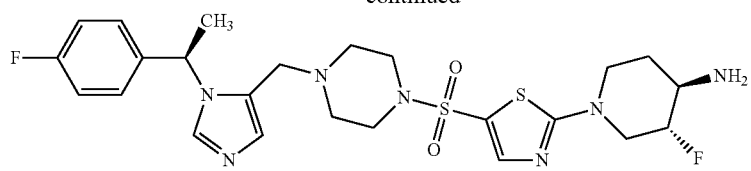
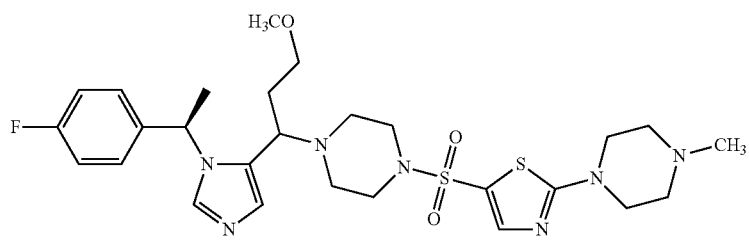
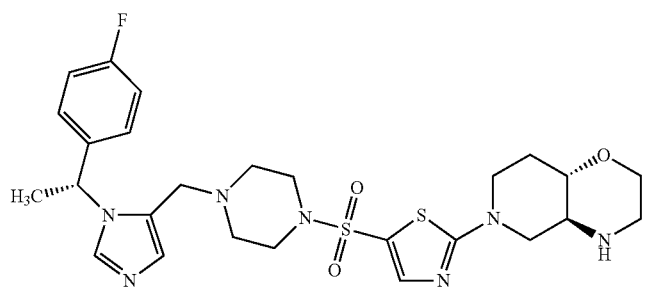
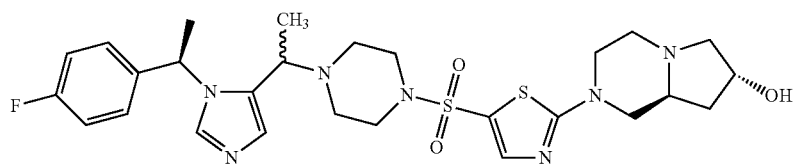
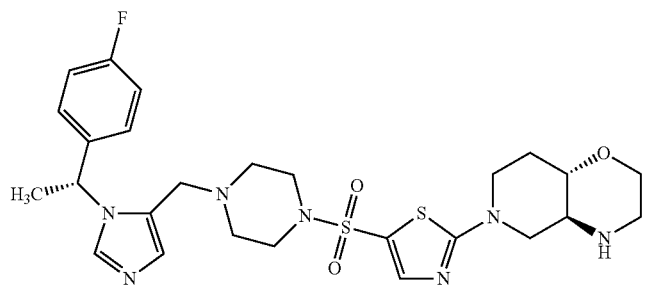
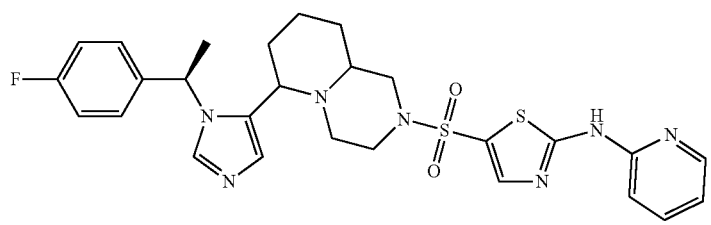
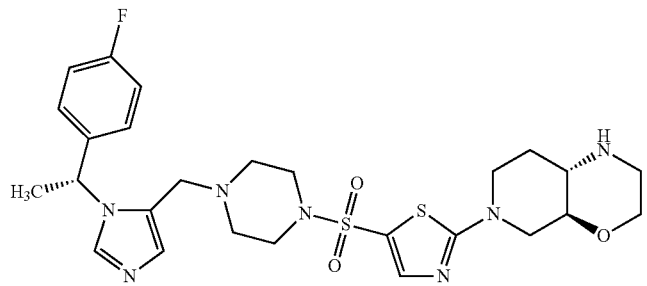

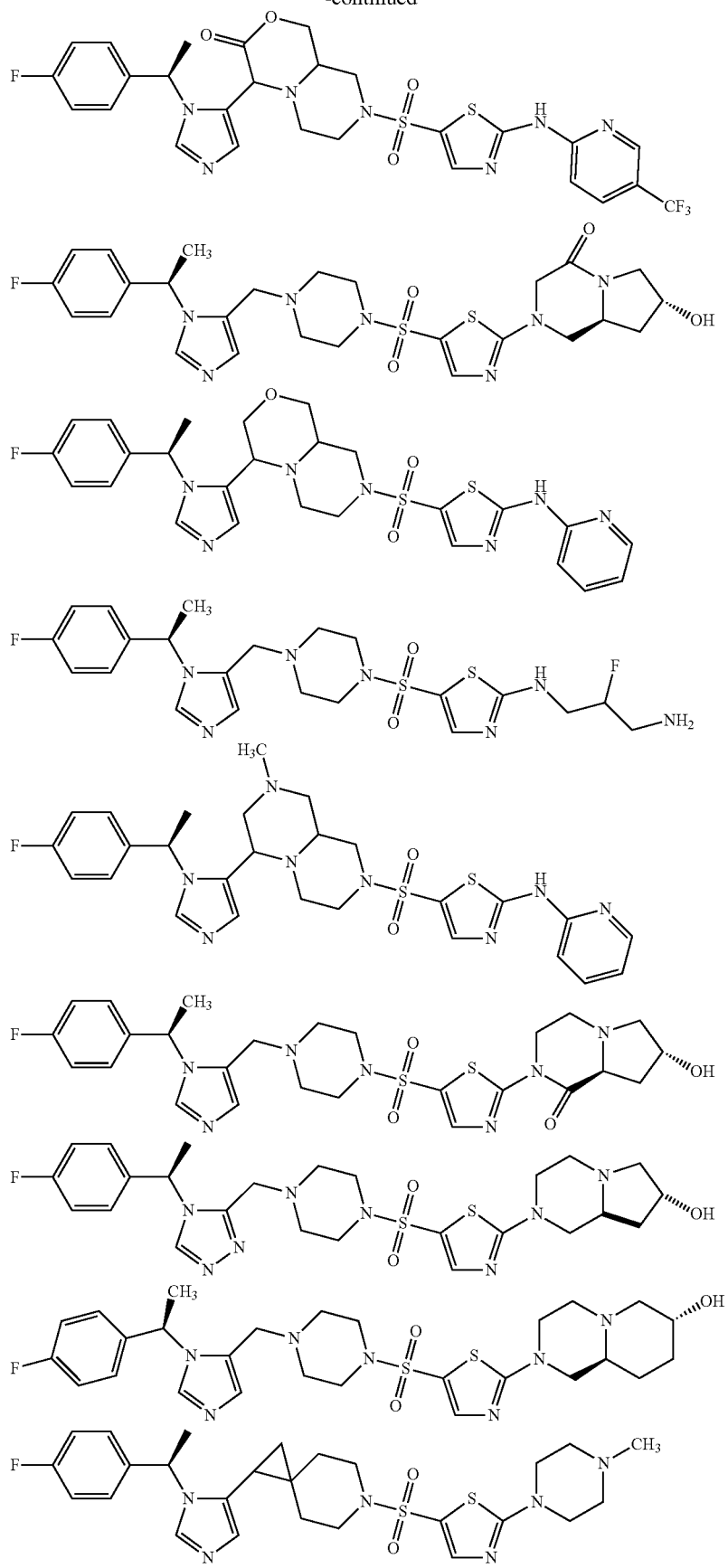

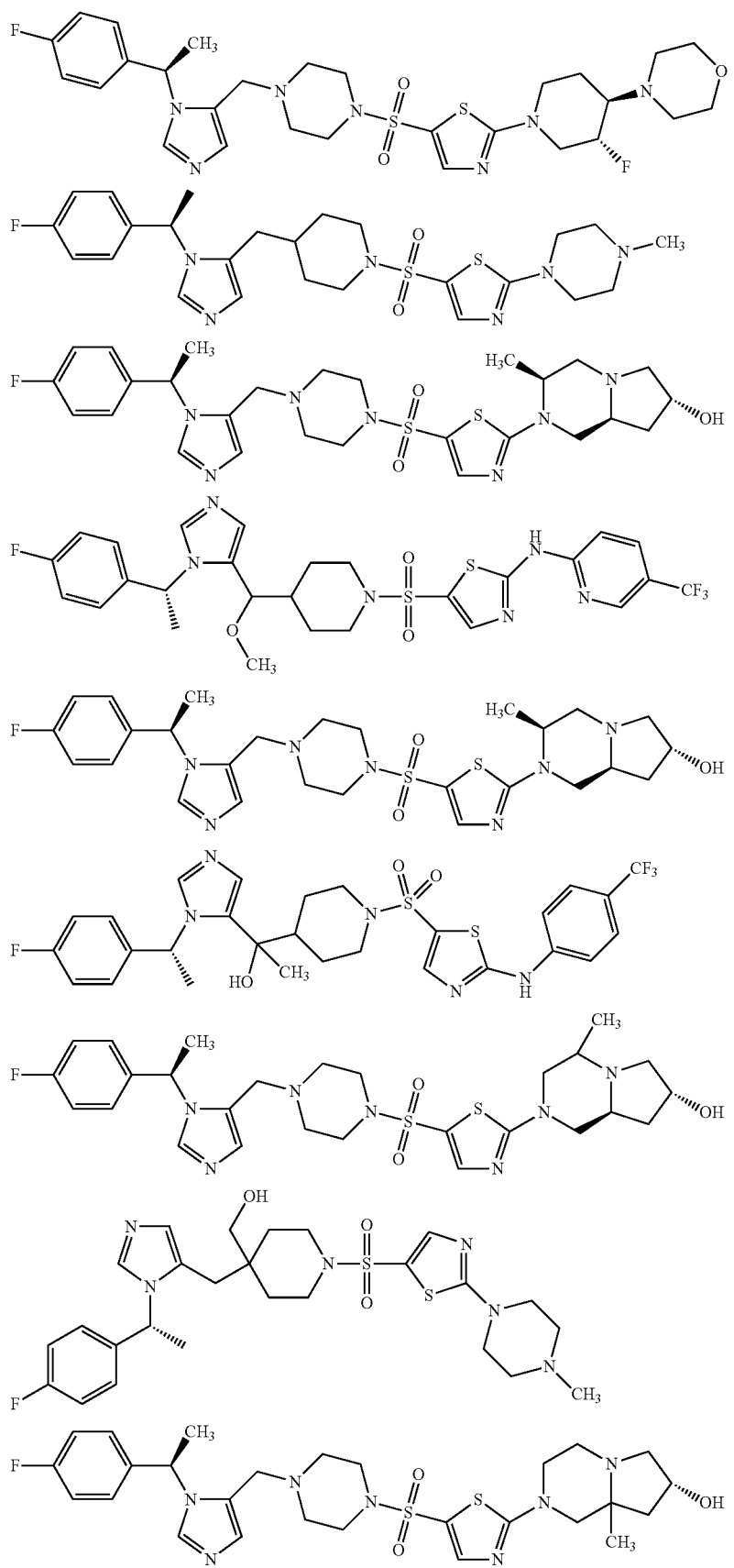

-continued

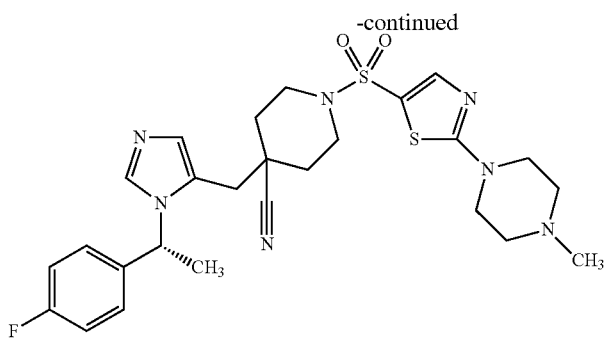

or a pharmaceutically acceptable salt thereof.

10. A pharmaceutical composition comprising an effective amount of a compound of claim 1 and a pharmaceutically acceptable carrier.

11. The pharmaceutical composition of claim 10, further comprising an anti-HIV drug.

12. The pharmaceutical composition of claim 11, wherein said anti-HIV drug is selected from an HIV protease inhibitor, an HIV integrase inhibitor, a nucleoside reverse transcriptase inhibitor and a non-nucleoside reverse-transcriptase inhibitor.

13. The pharmaceutical composition of claim 12, wherein said anti-HIV drug is selected from raltegravir, lamivudine, abacavir, darunavir, ritonavir, dolutegravir, atazanavir, elvitegravir and lopinavir.

14. The pharmaceutical composition of claim 13, further comprising a second anti-HIV drug, which is selected from an HIV protease inhibitor, an HIV integrase inhibitor, a nucleoside reverse transcriptase inhibitor and a non-nucleoside reverse-transcriptase inhibitor.

15. A method for improving the pharmacokinetics of a therapeutic compound that is metabolized by a CYP3A enzyme in subject, said method comprising administering to said subject in need of such treatment a combination of: (a) said therapeutic compound that is metabolized by a CYP3A enzyme and (b) a compound of claim 1, or a pharmaceutically acceptable salt thereof.

16. The method of claim 15, wherein said therapeutic compound is an anti-HIV drug.

17. The method of claim 16, wherein said anti-HIV drug is selected from an HIV protease inhibitor, an HIV integrase inhibitor, a nucleoside reverse transcriptase inhibitor and a non-nucleoside reverse-transcriptase inhibitor.

18. The method of claim 17, wherein said anti-HIV drug is selected from raltegravir, lamivudine, abacavir, ritonavir, dolutegravir, atazanavir, darunavir, elvitegravir and lopinavir.

19. The method of claim 18, wherein said anti-HIV drug is raltegravir.

20. The method of claim 15, wherein the therapeutic compound of (a) is metabolized by CYP3A4.

* * * * *